(12) United States Patent
Leonard et al.

(10) Patent No.: US 10,201,591 B2
(45) Date of Patent: Feb. 12, 2019

(54) **TSLP INDUCES NEUTROPHIL MEDIATED KILLING OF METHICILLIN-RESISTANT *STAPHYLOCOCCUS AUREUS***

(71) Applicants: The United States of America, as represented by the Secretary, Department of Health and Human Services, Washington, DC (US); The Board of Trustees of the Leland Stanford Junior University, Stanford, CA (US)

(72) Inventors: Warren Jaye Leonard, Bethesda, MD (US); Erin Elizabeth West, Washington Grove, MD (US); Rosanne Spolski, Silver Spring, MD (US); K. Christopher Garcia, Menlo Park, CA (US)

(73) Assignees: The United States of America, as represented by the Secretary, Department of Health and Human Services, Washington, DC (US); The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/345,213

(22) Filed: Nov. 7, 2016

(65) Prior Publication Data
US 2017/0128535 A1    May 11, 2017

Related U.S. Application Data

(60) Provisional application No. 62/251,558, filed on Nov. 5, 2015.

(51) Int. Cl.
| | |
|---|---|
| *A61K 38/04* | (2006.01) |
| *A61K 38/16* | (2006.01) |
| *A61K 38/19* | (2006.01) |
| *A61K 9/00* | (2006.01) |

(52) U.S. Cl.
CPC ............ *A61K 38/19* (2013.01); *A61K 9/0014* (2013.01); *A61K 9/0019* (2013.01)

(58) Field of Classification Search
None
See application file for complete search history.

(56) References Cited

PUBLICATIONS

Tokuriki et al. Current Opin. In Struct. Biol. 2009. 19:596-604.*
Bhattacharya et al. 2017. PLOS ONE, pp. 1-22.*
Wang et al 2001. J. Biol Chem. 276:49213-49220.*
Al-Shami et al., "A Role for TSLP in the development of inflammation in an asthma model" *J. Exp. Med.*, 202 (6), 829-839 (2005).
Bjerkan et al., "The short of TSLP is constitutively translated in human keratinocytes and has characteristics of an antimicrobial peptide" *Mucosal Immunology*, 8 (1), 49-56 (Jan. 2015).
GenBank Accession No. AF338732.1, "Homo sapiens thymic stromal lymphopoietin protein TSLP mRNA, complete cds," (dated Jun. 25, 2001).
GenBank Accession No. NM_021367.2, "Mus musculus thymic stromal lymphopoietin (Tslp), transcript variant 1, mRNA," (dated Sep. 18, 2017).
GenBank Accession No. NP_067342.1, "thymic stromal lymphopoietin precursor [Mus musculus]," (dated Sep. 18, 2017).
GenBank Accession No. Q969D9.1, "RecName: Full=Thymic stromal lymphopoietin; Flags: Precursor," (dated Jun. 7, 2017).
Kaplan et al., "Failure to Induce IFN-β Production during *Staphlococcus aureus* Infection Contributes to Pathogenicity," *J. Immunol.*, 189, 4537-4545 (2012).
Mestas et al., "Of Mice and Not Men: Differences between Mouse and Human Immunology," *J. Immunol.*, 172, 2731-2738 (2004).
Ribeiro-Gomes et al., "Site-Dependent Recruitment of Inflammatory Cells Determines the Effective Dose of *Leishmania major*," *Infect. Immun.*, 82 (7), 2713-2727 (2014).
Sonesson et al., "Thymic Stromal Lymphopoietin exerts antimicrobial activities" *Exp Dermatol.* 20 (12), 1004-1010 (Dec. 2011).

* cited by examiner

*Primary Examiner* — Shulamith H Shafer
(74) *Attorney, Agent, or Firm* — Leydig, Voit & Mayer, Ltd.

(57) ABSTRACT

The invention provides a method of promoting the host defense of a patient to a bacterial infection comprising administering to a patient suffering or at risk of a bacterial infection, a pharmaceutical composition comprising an effective amount of the pleiotropic cytokine, thymic stromal lymphopoietin (TSLP) protein or polypeptide in an amount and at a location sufficient to promote the host defense of the patient to the bacterial infection. In a preferred embodiment, the bacterial infection is the infection of the patient with MRSA.
The invention also provides a method of treating blood product, which comprises introducing a TSLP protein or polypeptide into such blood product, wherein the blood product is extracorporeal and comprises at least one neutrophil.

Figure 1A:
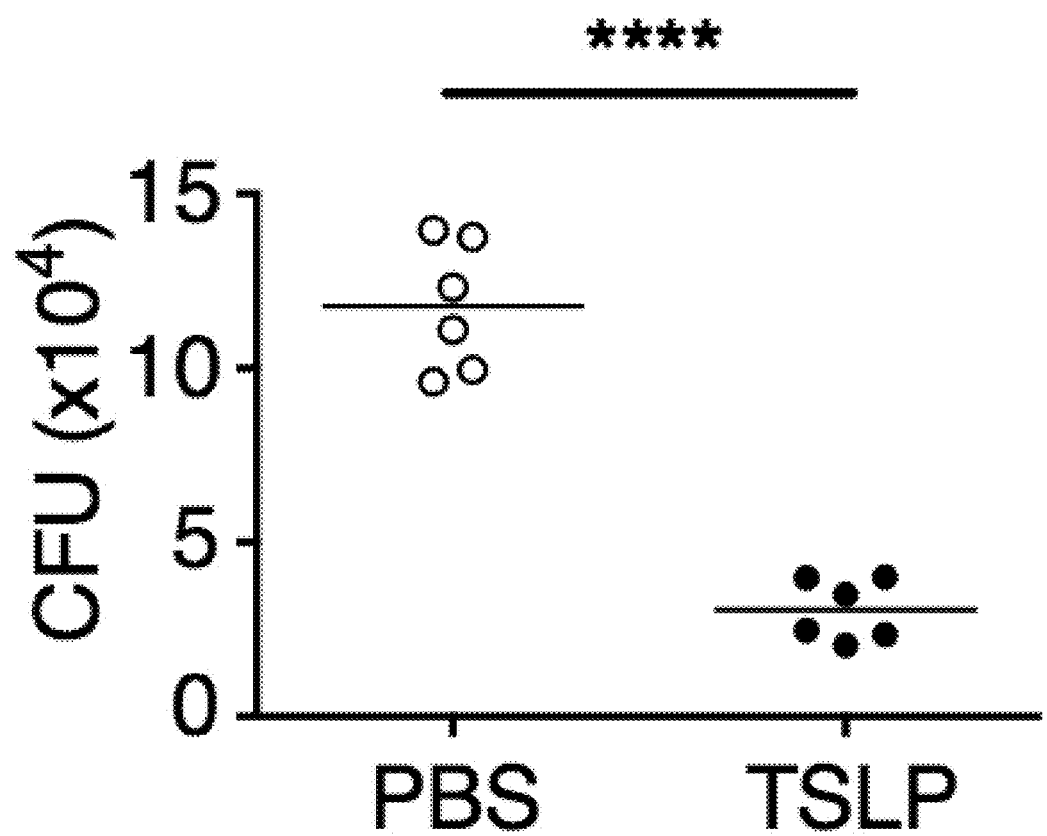
Figure 1B:
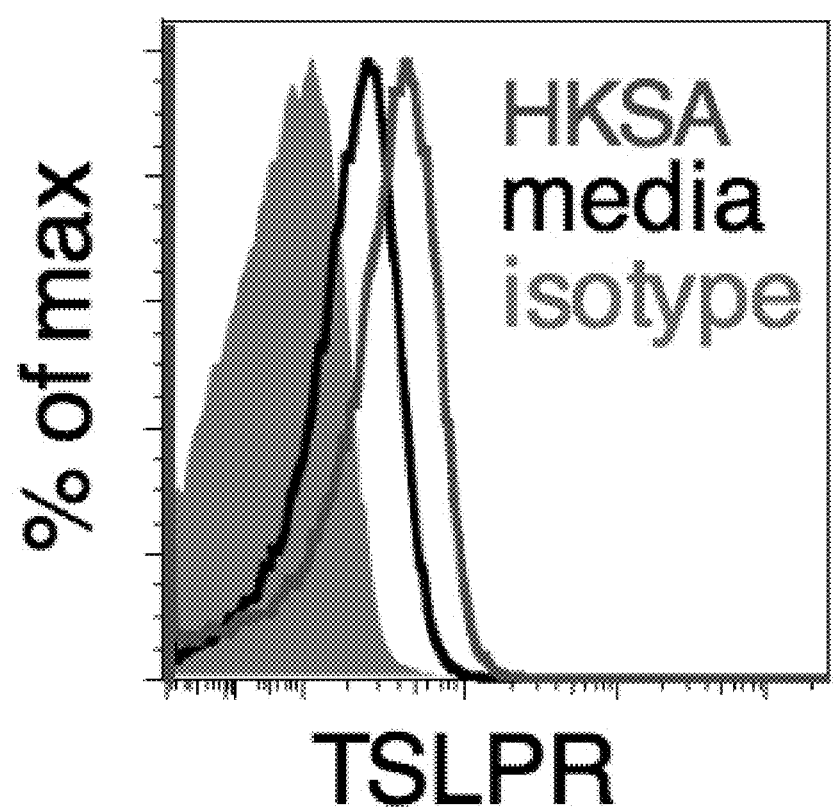
Figure 1C:
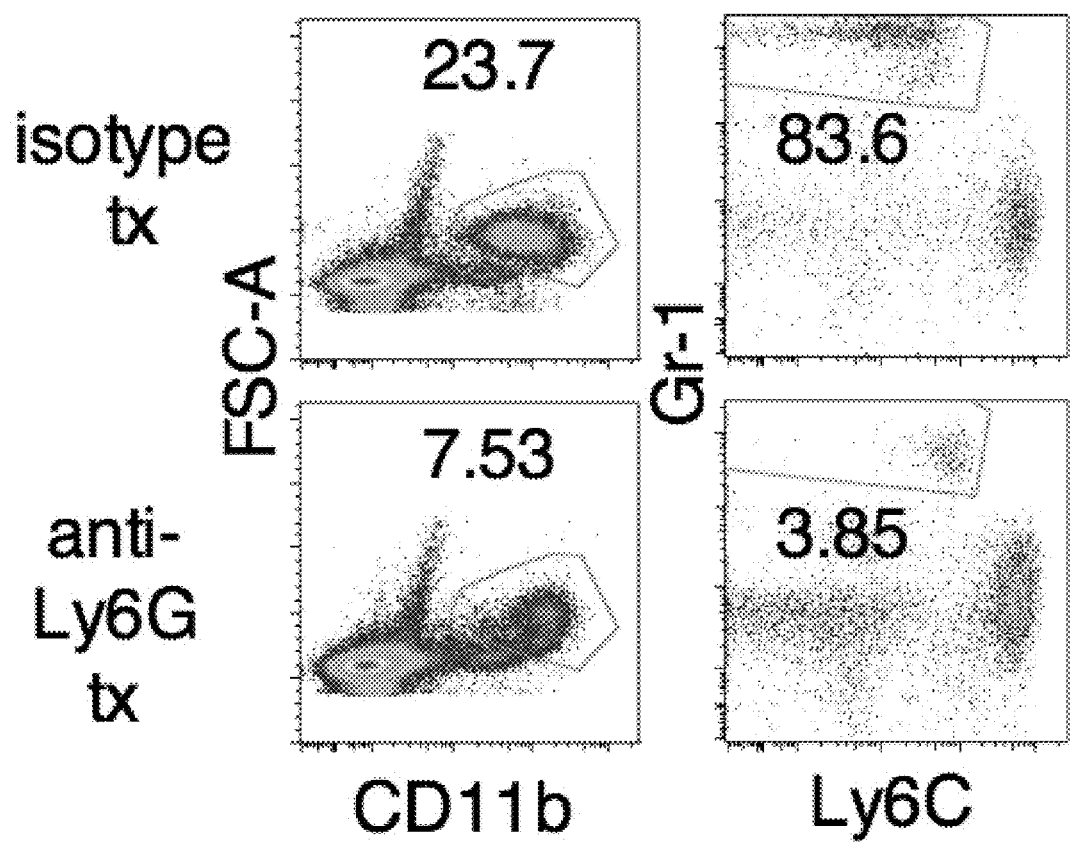

15 Claims, 71 Drawing Sheets
(10 of 71 Drawing Sheet(s) Filed in Color)
Specification includes a Sequence Listing.

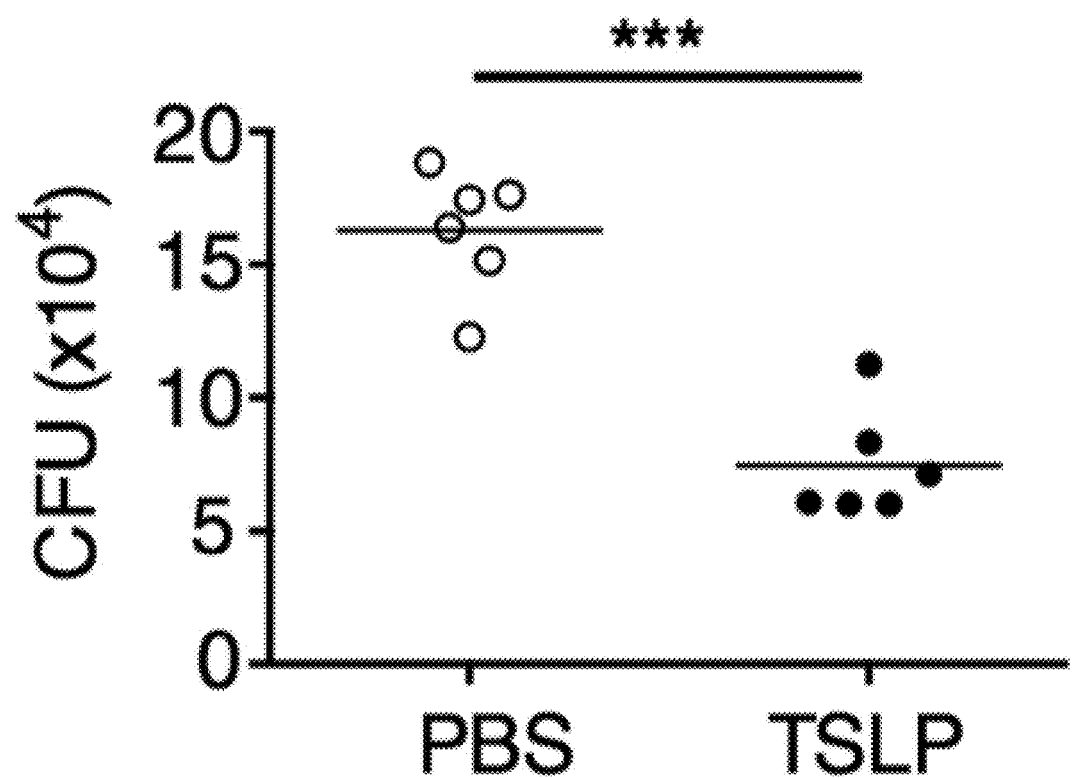

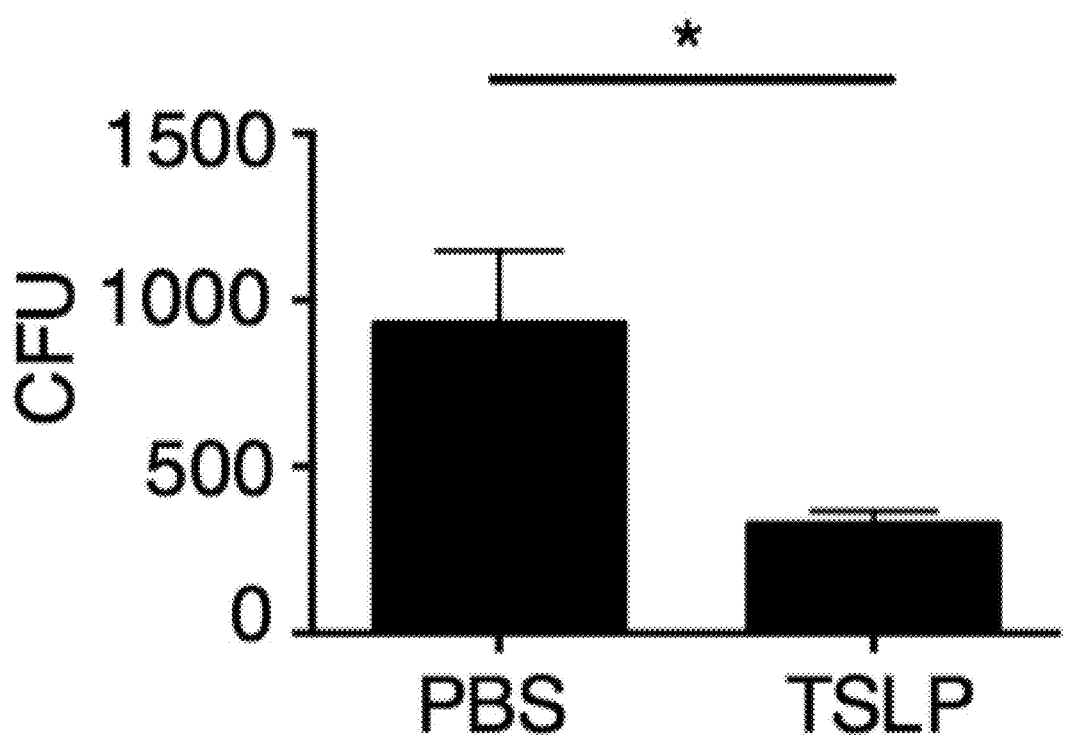

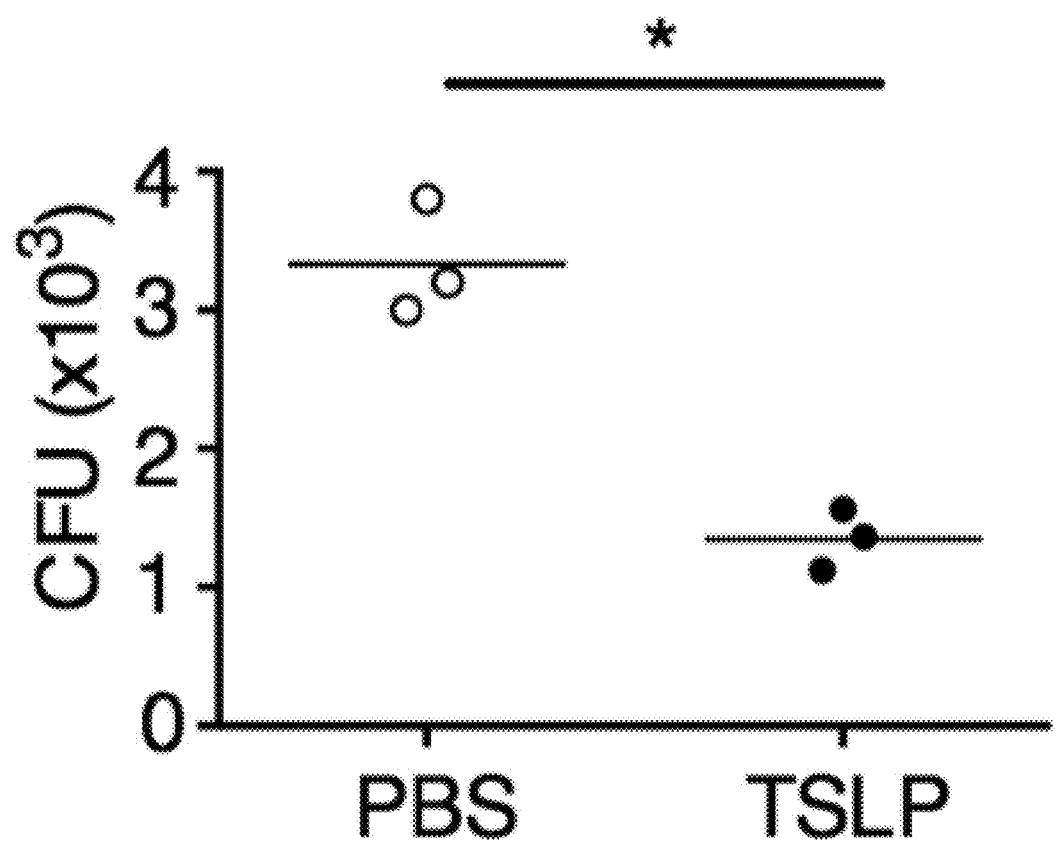

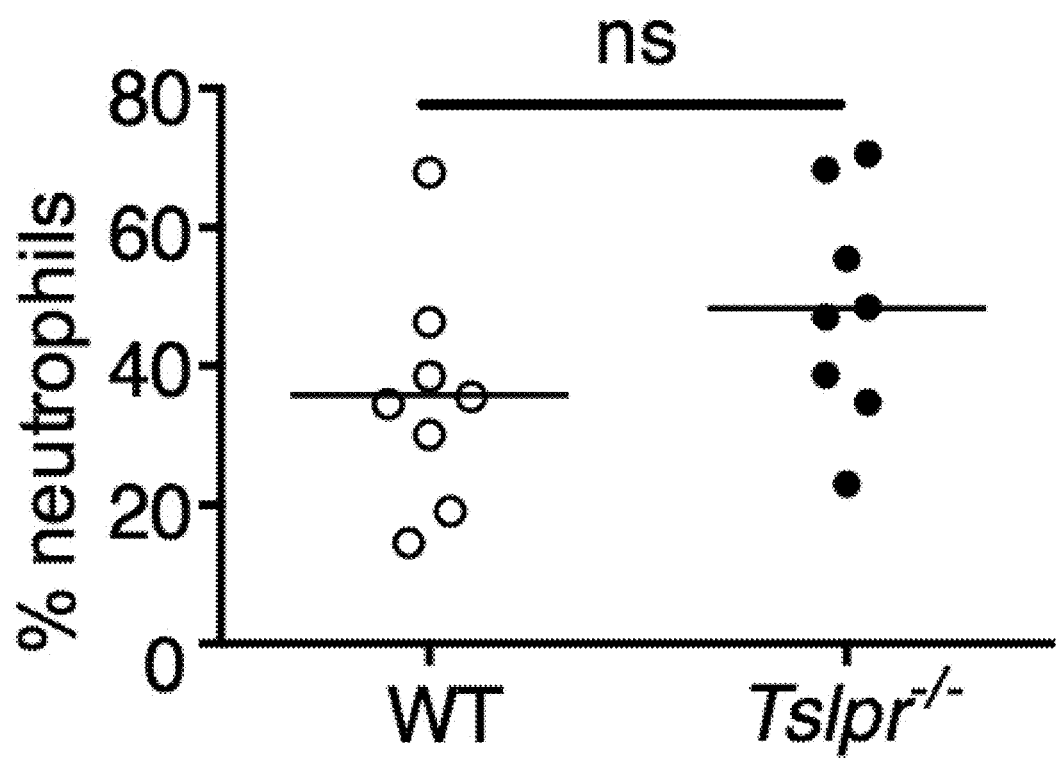

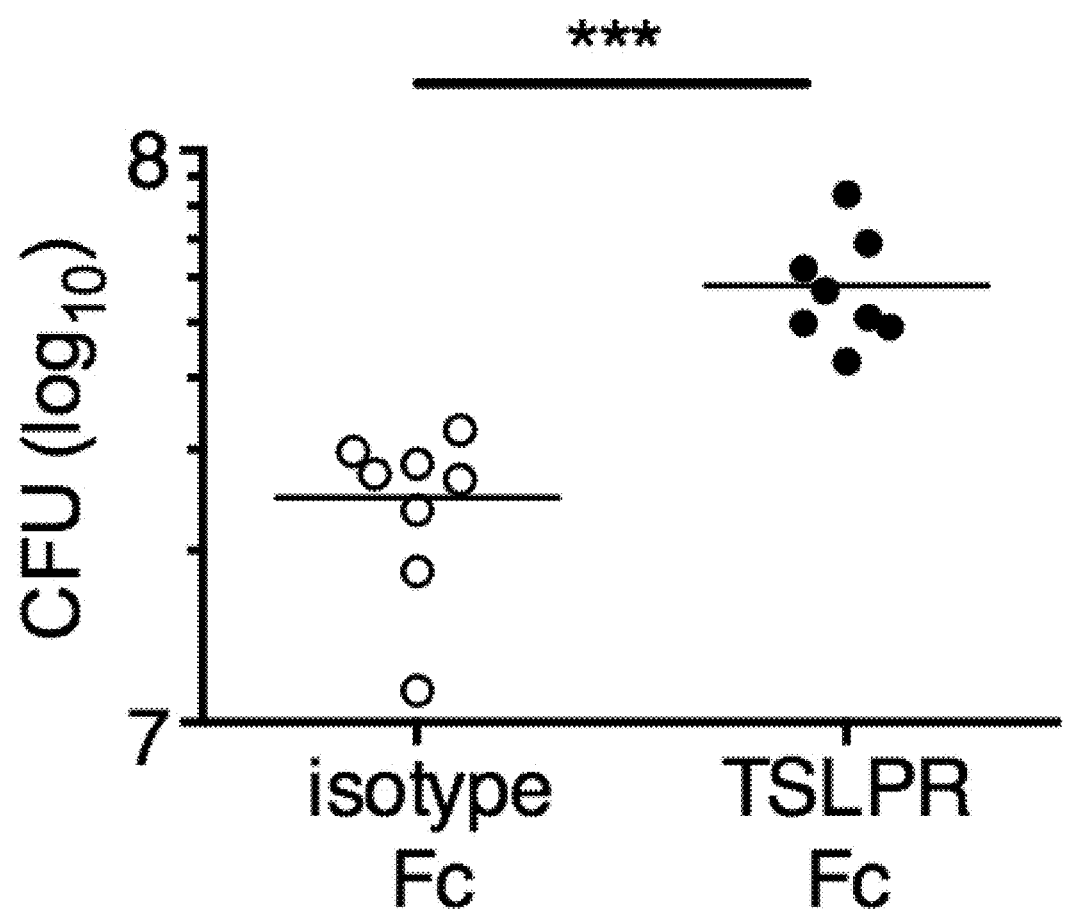

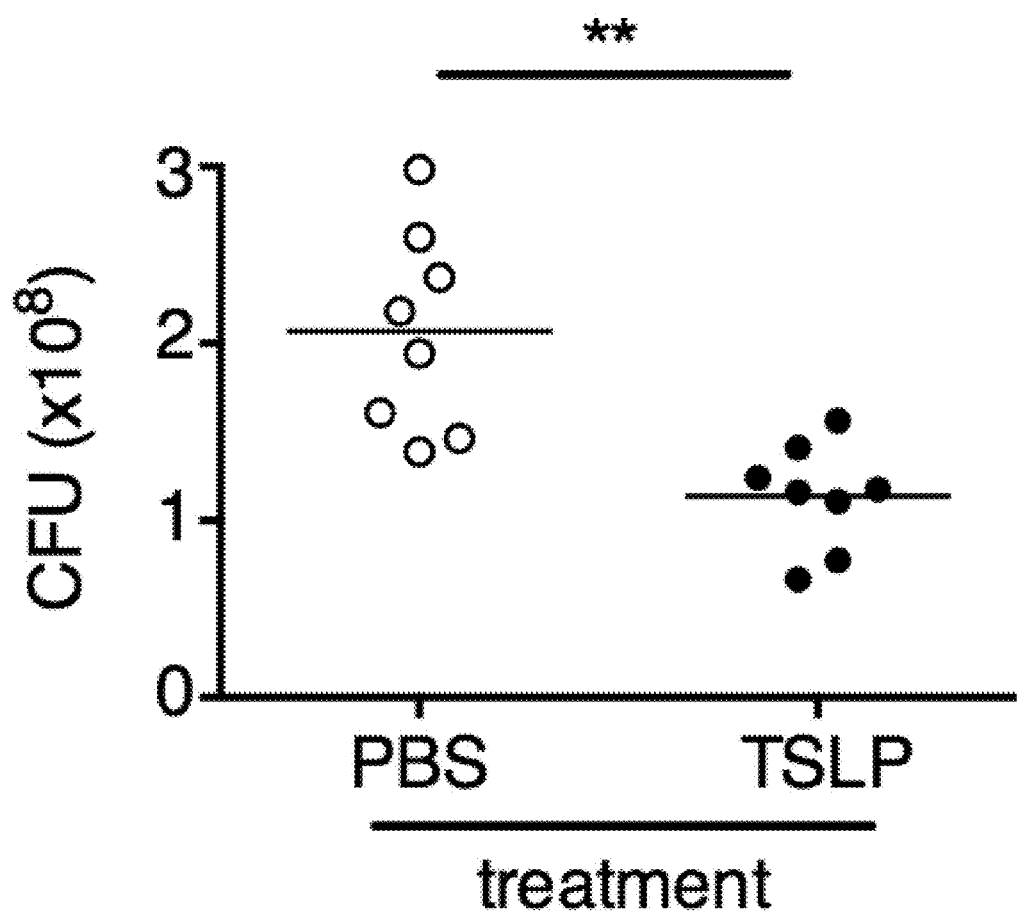

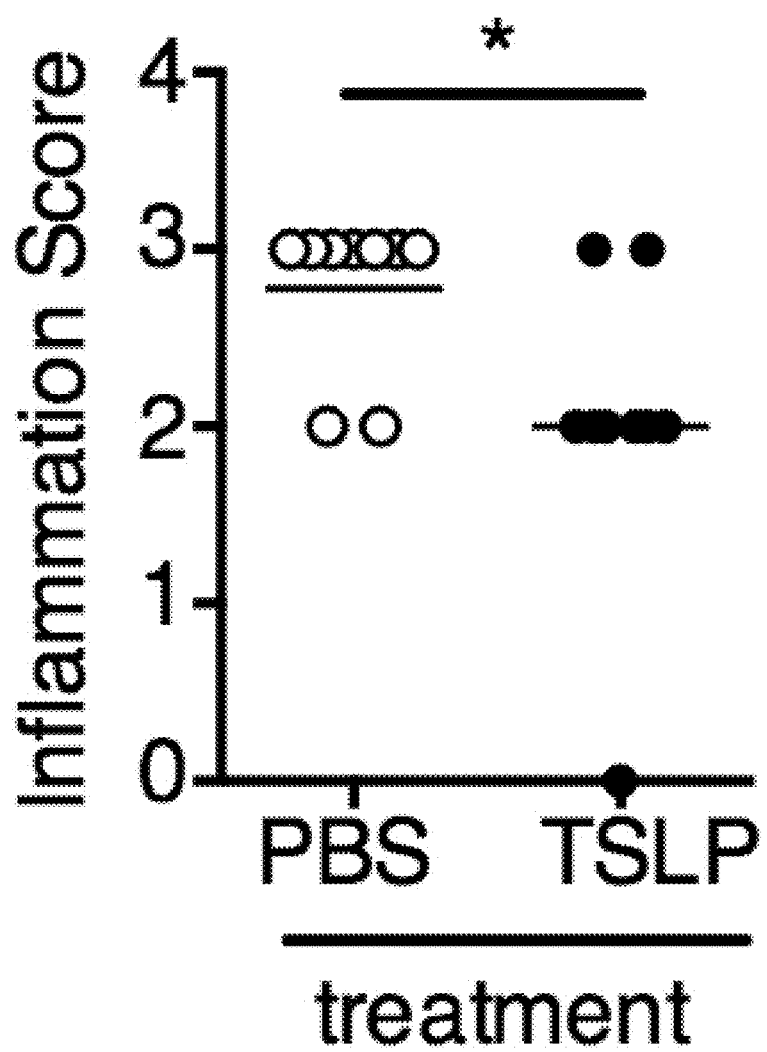

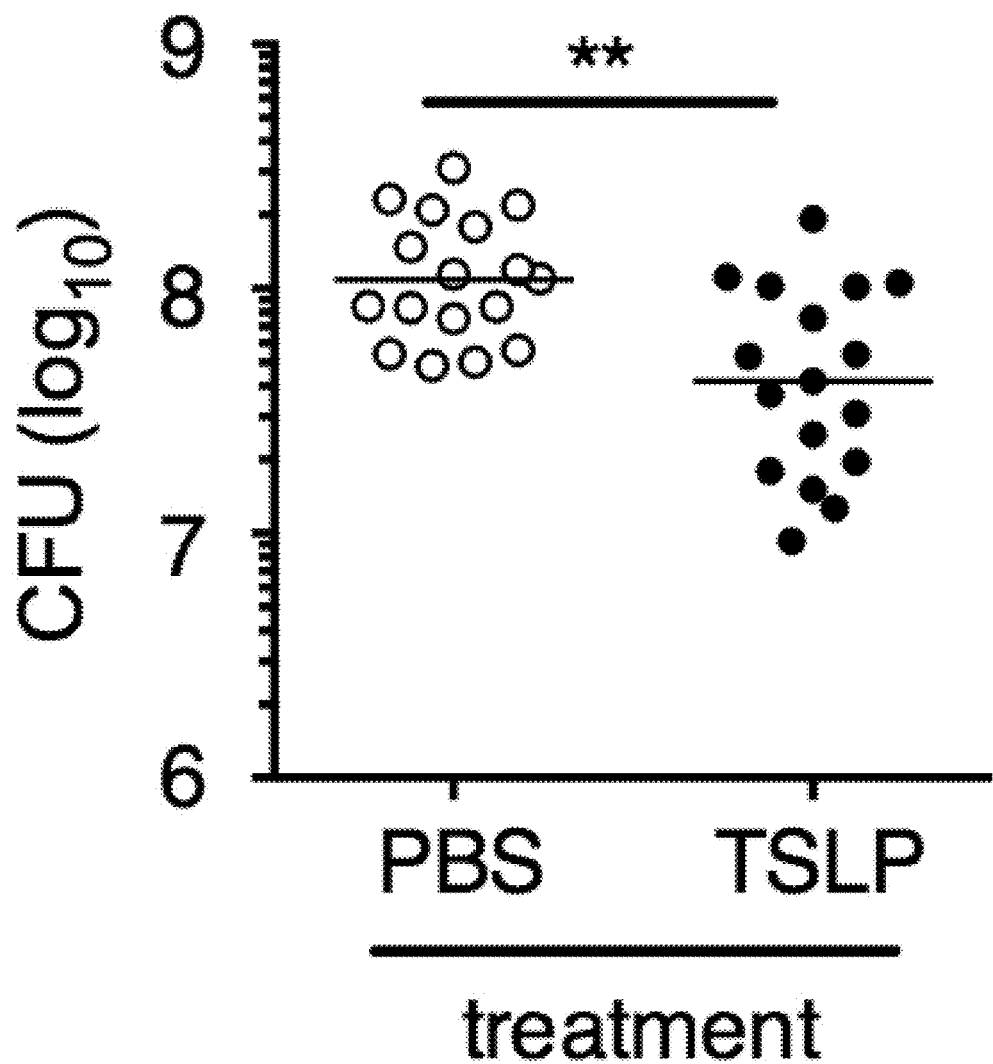

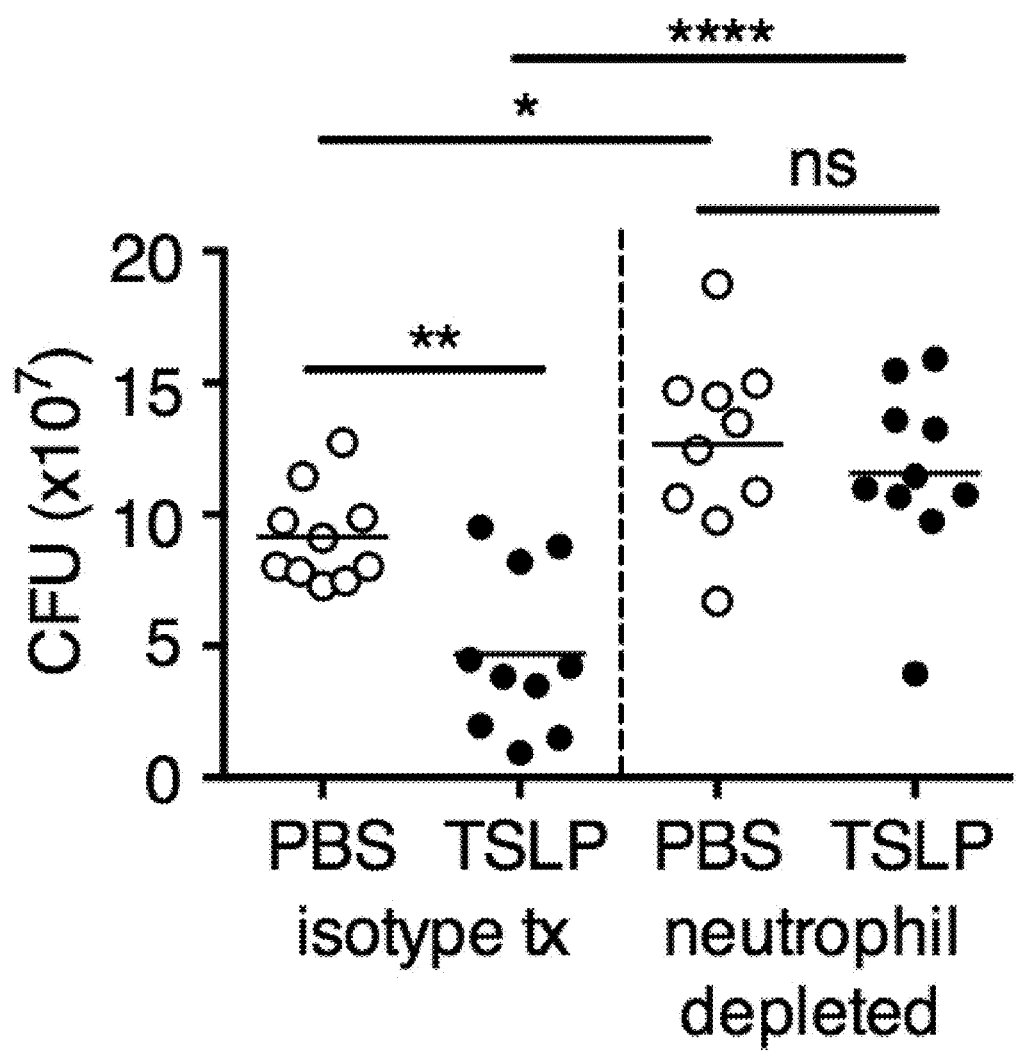

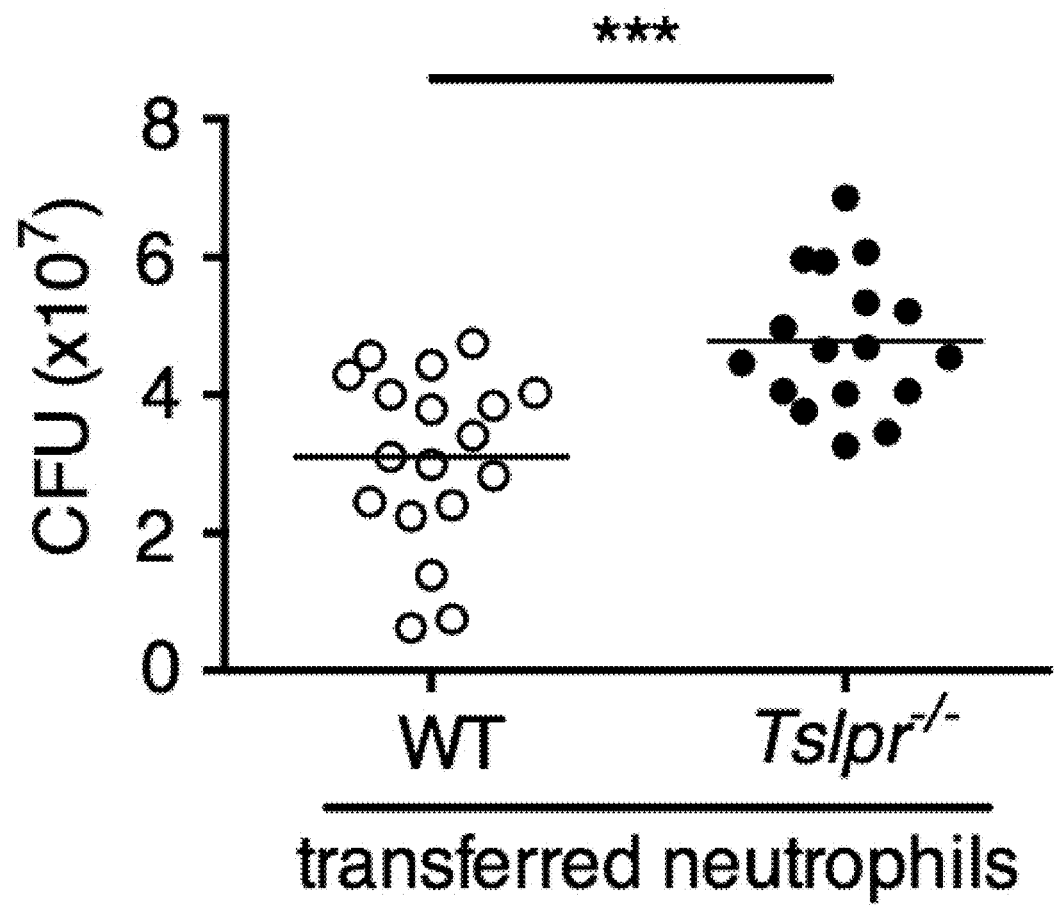

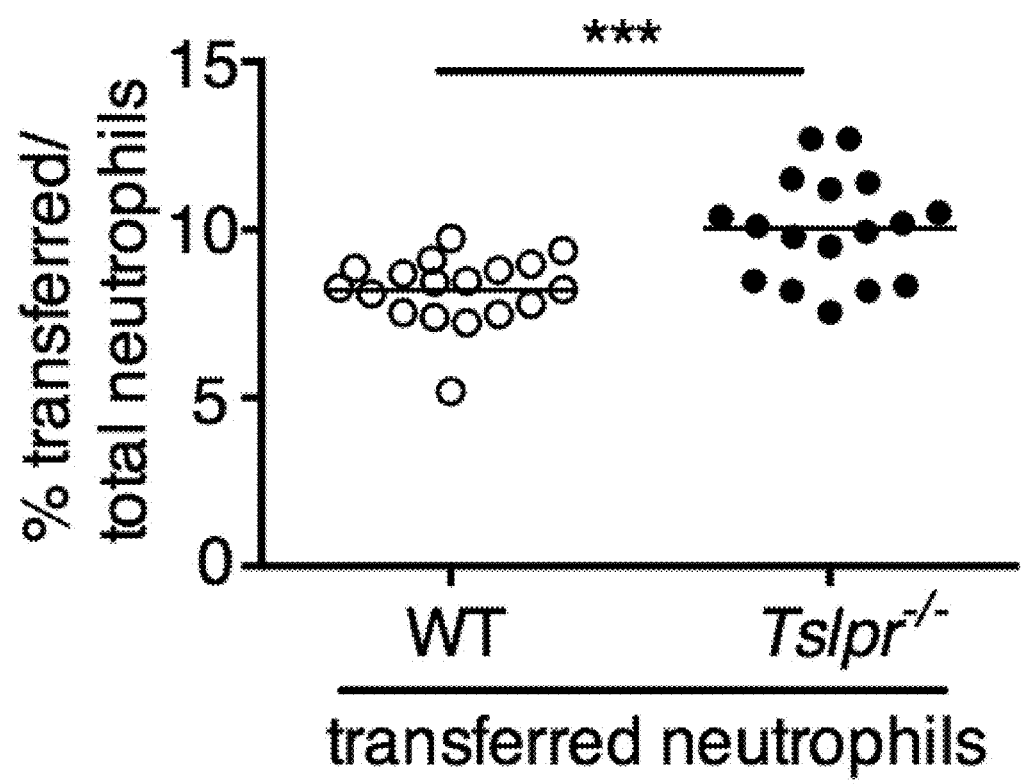

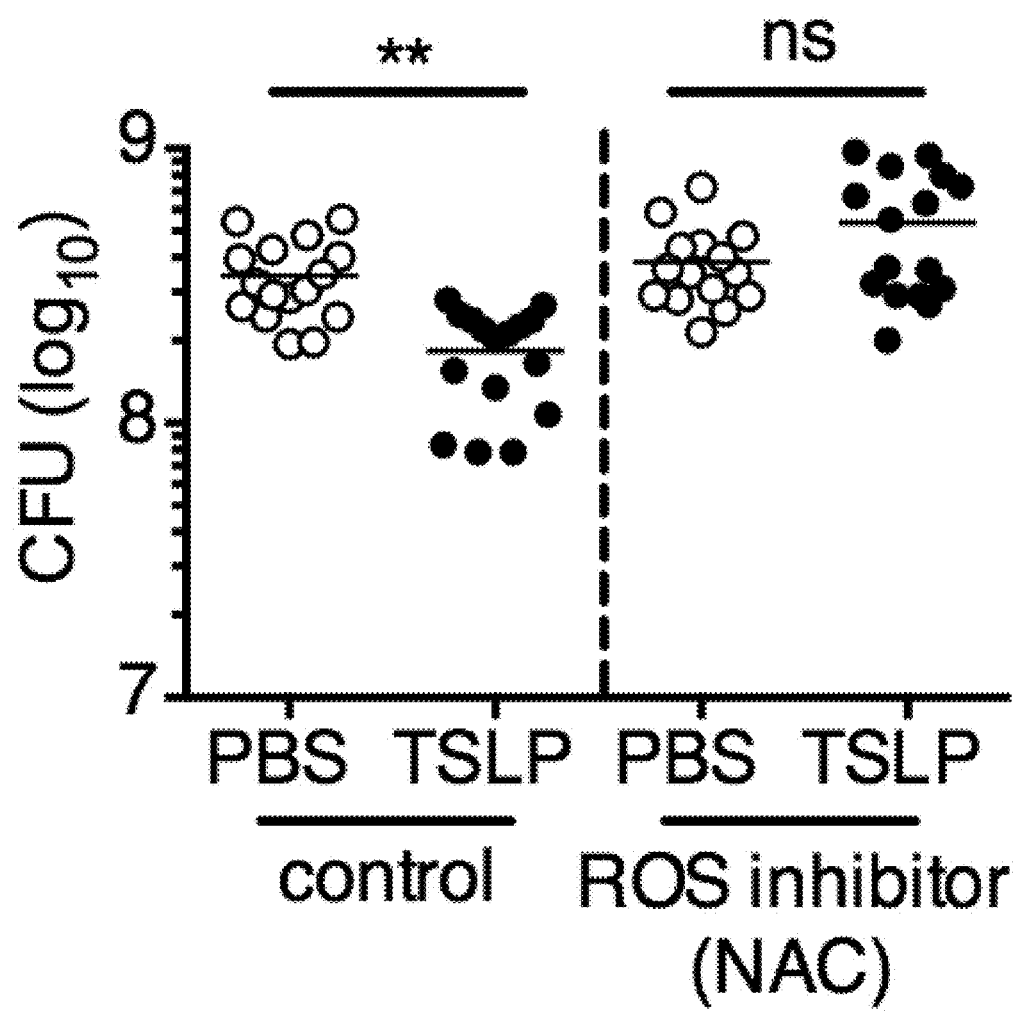

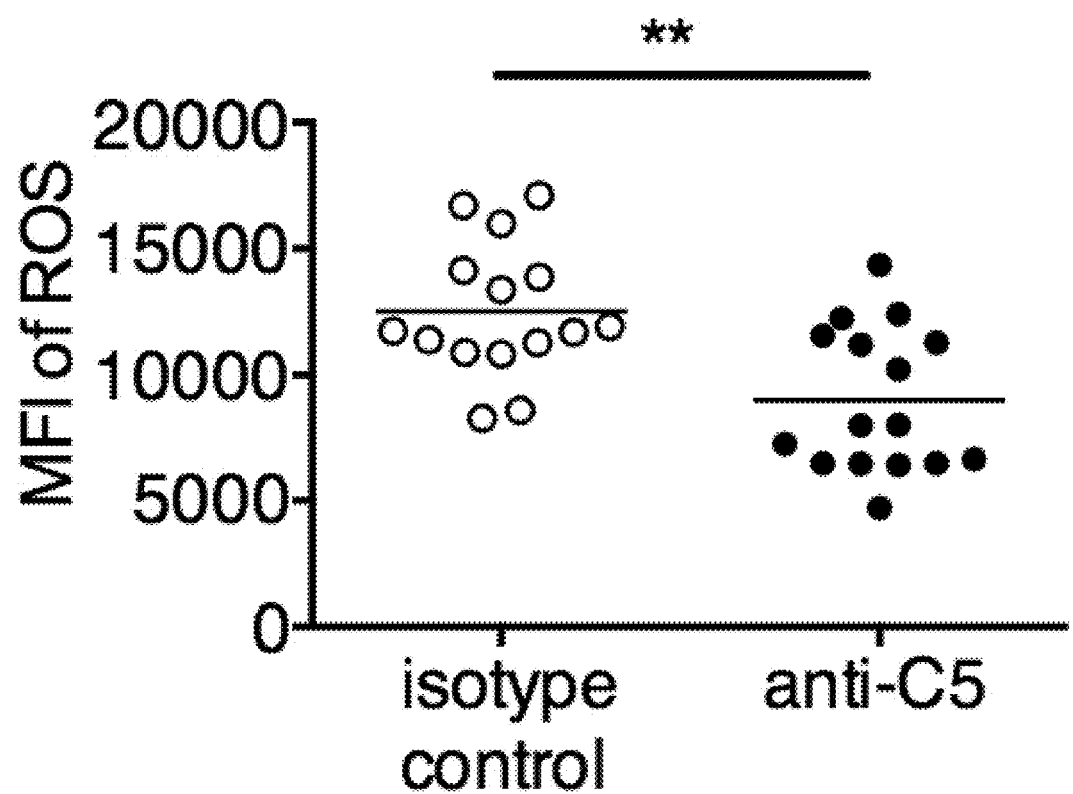

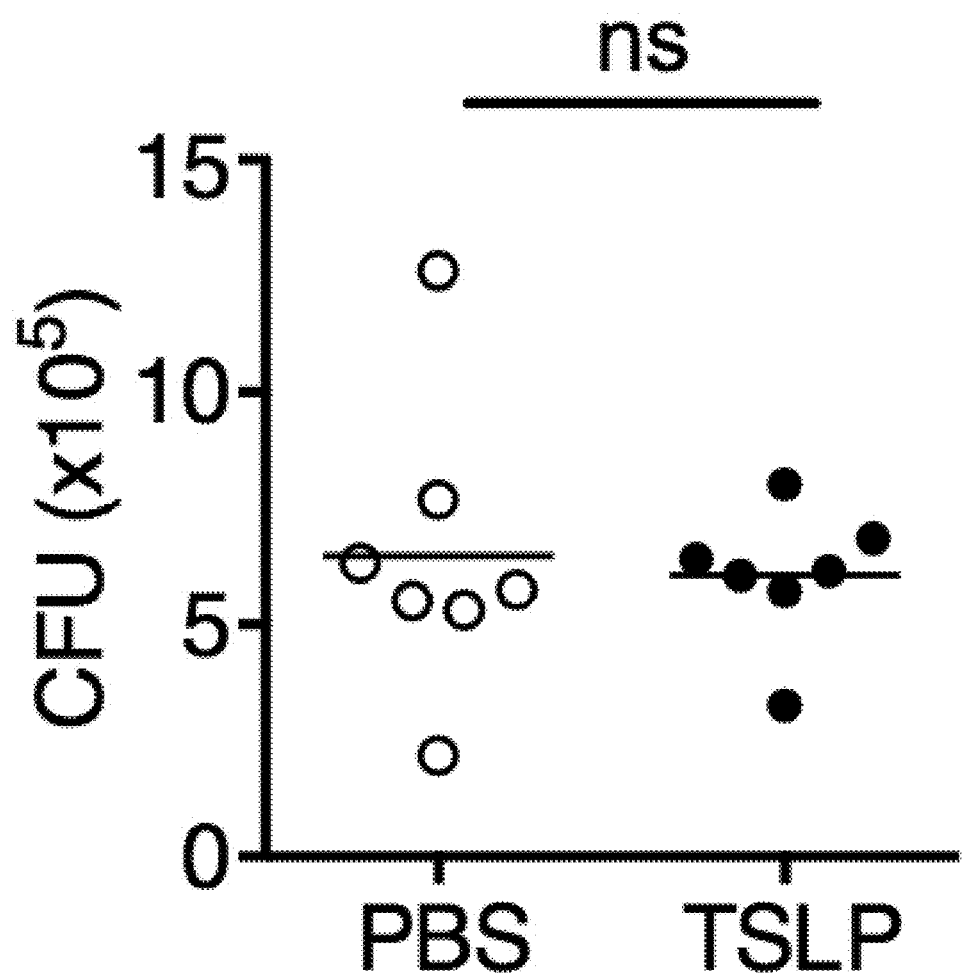

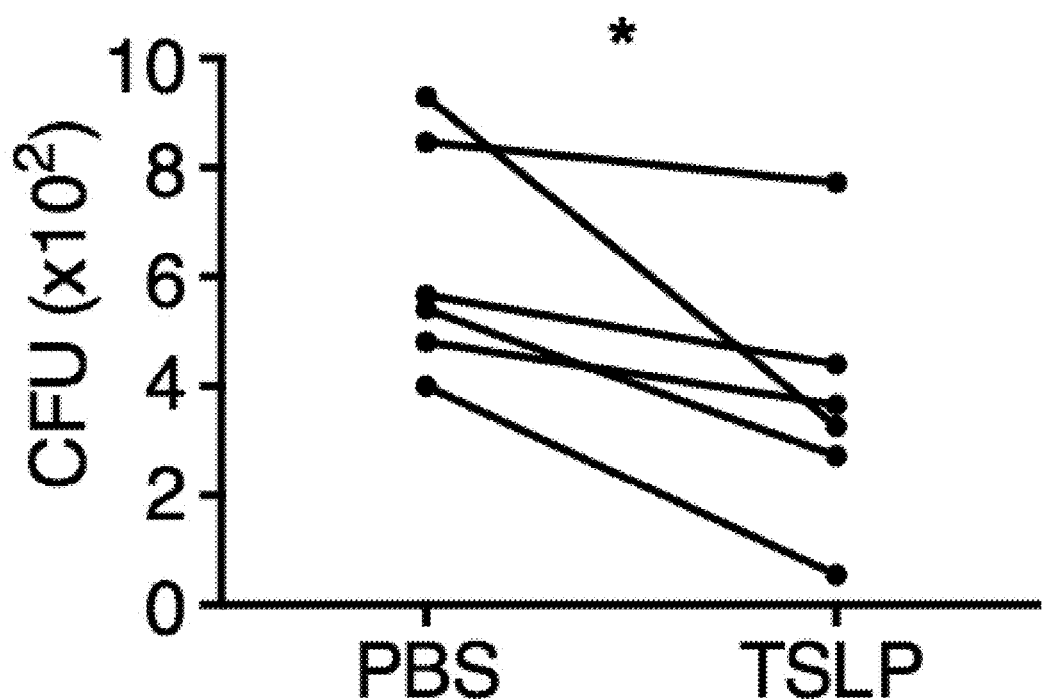

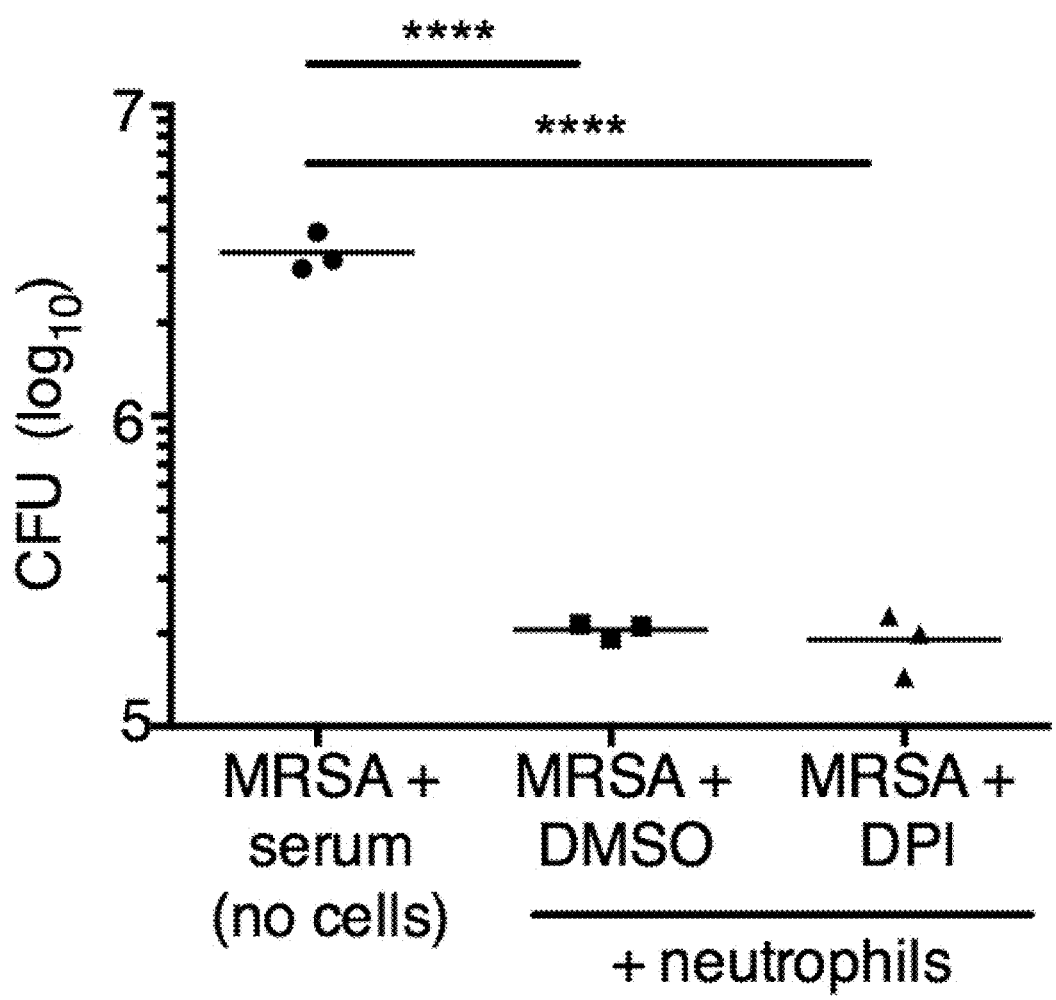

TSLP INDUCES NEUTROPHIL MEDIATED KILLING OF METHICILLIN-RESISTANT *STAPHYLOCOCCUS AUREUS*

CROSS-REFERENCE TO RELATED APPLICATIONS

This patent application claims the benefit of U.S. Provisional Patent Application 62/251,558, filed Nov. 5, 2015, the entire contents of which are incorporated herein by reference.

STATEMENT REGARDING FEDERALLY SPONSORED RESEARCH OR DEVELOPMENT

This invention was made with Government support under project number HL-005409 by the National Institutes of Health. The Government has certain rights in the invention.

STATEMENT PURSUANT TO 37 C.F.R. § 1.84 RELATED TO COLOR DRAWINGS

The patent or application file contains at least one drawing executed in color. Copies of this patent or patent application publication with color drawing(s) will be provided by the Office upon request and payment of the necessary fee.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 11,914 byte (Text) file named "726970_ST25," created on Nov. 7, 2016.

BACKGROUND OF THE INVENTION

Antibiotic resistant bacterial infections, including Methicillin-resistant *Staphylococcus aureus* (MRSA), are increasing in prevalence world-wide at alarming rates. In particular, community-acquired MRSA infections, often presenting as serious skin infections in otherwise healthy individuals, have become a world-wide epidemic problem and warrant attention for therapeutic intervention. While MRSA was once mainly considered a hospital-acquired infection, the emergence of new strains has resulted in serious skin infections in otherwise healthy individuals. Thus there is a need for methods and reagents for increasing the effectiveness in treating MRSA as well as other bacterial infections, and defining the mechanisms that govern the activation and regulation of the immune response to MRSA as well as other bacterial infections is clinically important and could lead to the discovery of much needed rational targets for therapeutic intervention.

BRIEF SUMMARY OF THE INVENTION

The invention provides a method of promoting the host defense of a patient to a bacterial infection comprising administering to a patient suffering or at risk of a bacterial infection, a pharmaceutical composition comprising an effective amount of the pleiotropic cytokine, thymic stromal lymphopoeitin (TSLP), or a functional variant thereof (collectively, "a TSLP protein or polypeptide") in an amount and at a location sufficient to promote the host defense of the patient to the bacterial infection. The invention also provides the use of TSLP for preparing a medicament for promoting the host defense of a patient to a bacterial infection. In a preferred embodiment, the bacterial infection is the infection of the patient with MRSA.

The invention also provides a method of treating blood product, which comprises introducing TSLP into such blood product, wherein the blood product is extracorporeal and comprises at least one neutrophil.

BRIEF DESCRIPTION OF THE SEVERAL VIEWS OF THE DRAWING(S)

Figure 1D:
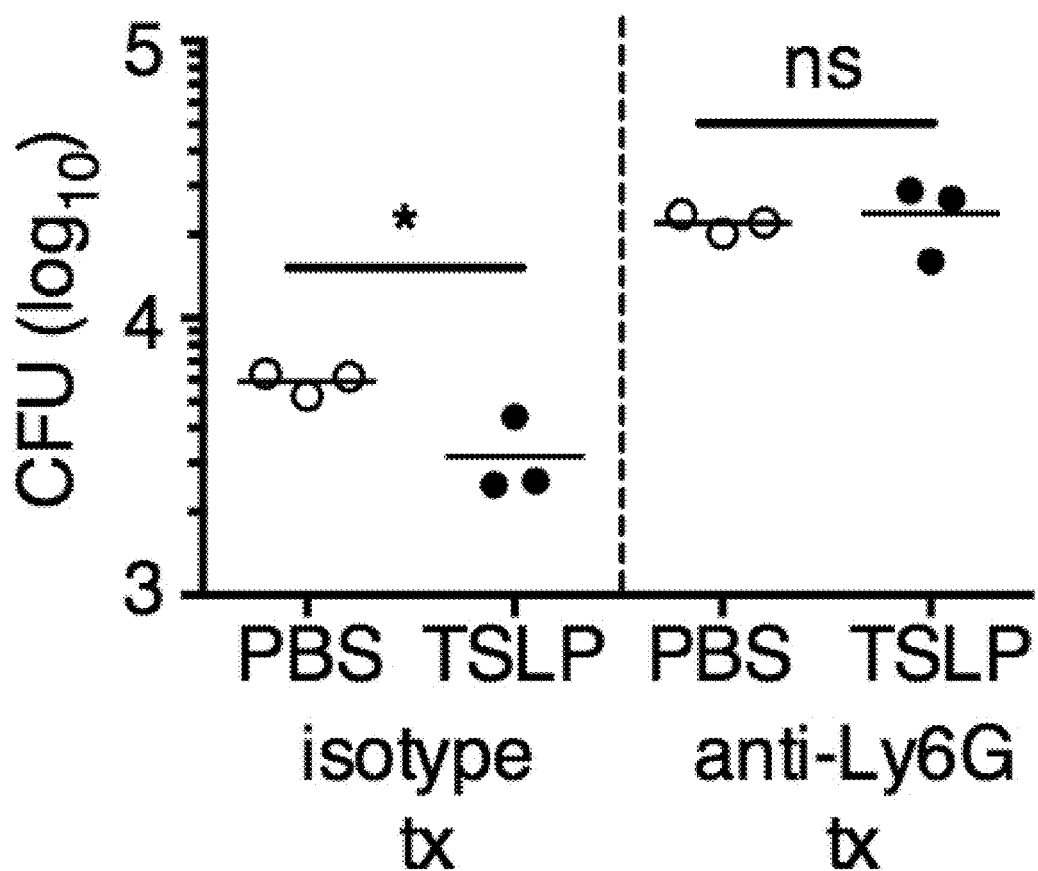

FIG. 1A through FIG. 1D: TSLP increases MRSA killing in mouse blood in a neutrophil-dependent manner. (FIG. 1A, FIG. 1C, FIG. 1D) Mouse blood was incubated with PBS or TSLP and MRSA for 3 h. (FIG. 1A) CFU analysis (shown is a representative experiment from blood from 2 mice performed in triplicate). (FIG. 1B) TSLPR expression on mouse neutrophils incubated with medium or HKSA. (FIG. 1C) Flow-cytometric staining of blood neutrophils in mice treated with a control antibody or depleted of neutrophils using anti-Ly6G antibody. (FIG. 1D) A representative experiment showing CFU of MRSA after an in vitro whole blood killing assay performed with blood from mice treated with an isotype control or anti-Ly6G antibodies (blood from 2-3 mice were combined for each treatment condition and assayed in triplicate). *, $p<0.05$; ***, $p<0.001$; ns=not significant, two-tailed Student's t-test. Data are representative of 6 independent experiments for (FIG. 1A), 2 experiments for (FIG. 1B) and 3 experiments for (FIG. 1C) and (FIG. 1D).

FIG. 2A through FIG. 2F: TSLP acts directly on both mouse and human neutrophils to increase MRSA killing in vitro. (FIG. 2A, FIG. 2B) Thioglycollate-elicited mouse neutrophils were used. (FIG. 2A) Representative flow-cytometric staining of TSLPR expression on neutrophils. (FIG. 2B) CFU after purified neutrophils were incubated with PBS or TSLP and MRSA for 2 h. (FIG. 2C) Whole human blood was incubated with MRSA and PBS or TSLP for 3 h and CFU determined (representative graph of 1 donor shown in triplicate, statistics shown are of two-tailed paired t-test from 6 donors). (FIG. 2D through FIG. 2F) Purified human blood neutrophils were used. (FIG. 2D) CRLF2 expression by human blood neutrophils determined by RT-PCR after 4 h treatment with medium (control) or HKSA (representative donor shown) and normalized to expression of RPL7. (FIG. 2E) Representative flow-cytometric staining of TSLPR on human blood neutrophils. (FIG. 2F) CFU after neutrophils were incubated with MRSA and PBS or TSLP for 3 h (shown is a representative graph of 1 donor done in triplicate; statistics shown are of two-tailed paired t-test from 7 donors). *, $p<0.05$; ***, $p<0.001$; ns=not significant, using two-tailed Student's t-test for unless indicated. Data are representative of at least 3 independent experiments.

FIG. 3A through FIG. 3G: Tslpr-deficient mice have increased MRSA burden during in vivo skin infection. (FIG. 3A-FIG. 3G) Mice were infected with MRSA i.d. in the ear. (FIG. 3A) TSLP protein expression in the ear after i.d. MRSA infection (n=4), naïve controls were mock-infected with PBS only. (FIG. 3B-FIG. 3G) Ears were analyzed on day 1 p.i. (FIG. 3B) Representative TSLPR expression on neutrophils. (FIG. 3C) Analysis of CFU in the ear of WT (n=11) and Tslpr$^{-/-}$ mice (n=12 ears). (FIG. 3D-FIG. 3F) Analysis of neutrophils in the ear. Shown are representative FACS plots (FIG. 3D) and percent (FIG. 3E) and total number (FIG. 3F) of neutrophils from WT and Tslpr$^{-/-}$ mice (n=8 ears). (FIG. 3G) CFU of MRSA in the ear on day 2 post-i.d. ear infection of WT mice treated with human IgG1 Fc isotype control or TSLPR Fc (two-tailed Mann-Whitney test) (n=8 ears). *, p<0.05; , p<0.01; *, p<0.001; ns=not significant. a-f, Two-tailed Student's t-test. Data are representative of 3 (or 2 for (FIG. 3G)) independent experiments.

FIG. 4A through FIG. 4F: TSLP treatment enhances in vivo MRSA and *S. pyogenes* killing during a skin infection. Mice were infected with MRSA i.d. in the ear. (FIG. 4A) CFU of MRSA at day 2 p.i. in the ears of WT mice treated with PBS or TSLP (two-tailed Mann-Whitney test) (n=10 ears). (FIG. 4B) Representative images of hematoxylin and eosin (H&E)-stained ear sections on day 2 p.i. (5× magnification: bar indicates 200 microns). (FIG. 4C) Inflammation score according to blinded histological analysis (n=9 ears). (FIG. 4D) CFU of *S. pyogenes* in the ears of WT mice treated with PBS or TSLP on day 1 post-i.d infection (two-tailed Mann-Whitney test) (n=17 ears, shown are results of two combined independent experiments). (FIG. 4E) CFU in the ear of WT, neutrophil-depleted WT, and Tslpr$^{-/-}$ mice on day 1 p.i. (two-tailed Mann-Whitney test) (n=8 ears for WT and Tslpr$^{-/-}$, n=6 for neutrophil depleted WT) (FIG. 4F) CFU of MRSA in the ears of WT mice or neutrophil-depleted WT mice treated with PBS or TSLP on day 2 p.i. (two-tailed Mann-Whitney test) (n=10 ears). *, p<0.05; , p<0.01; *, p<0.001; ns=not significant. Data are representative of 2 (FIG. 4B, FIG. 4C, FIG. 4E, F) or 4 (FIG. 4A) independent experiments.

FIG. 5A through FIG. 5F: TSLP acts directly on neutrophils in vivo to enhance killing of MRSA during a skin infection. (FIG. 5A) Equal numbers of purified bone marrow neutrophils from WT (CD45.1+/2+) and Tslpr$^{-/-}$ (KO; CD45.1+/1+) mice were co-transferred i.v. into WT C57BL/6 host mice (CD45.2+/2+) and were then infected with MRSA i.d. in the ear. Shown is a representative flow cytometric plot of the neutrophil populations in the ear on day 1 p.i. (n=10, gated on neutrophils=live CD11bhiLy6GhiLy6Clo cells). (FIG. 5B) Experimental design for (FIG. 5C-FIG. 5F), where an equal number of purified CellTracker Green (CMDFA) labeled WT or Tslpr-/- bone marrow neutrophils were transferred i.v. into Tslpr$^{-/-}$ host mice, which were subsequently injected with MRSA+TSLP i.d. in the ear. (FIG. 5C) CFU of MRSA in the ears 16-18 h p.i. (n=17-18). (FIG. 5D) Representative flow-cytometric plot showing the percent of transferred neutrophils (CMDFA+) out of total neutrophils in the ears of Tslpr$^{-/-}$ mice receiving no cells, WT neutrophils, or Tslpr$^{-/-}$ neutrophils (n=17-18 from two combined individual experiments, gated on total neutrophils). (FIG. 5E) Percent and (FIG. 5F) number of transferred neutrophils per ear (n=17-18). *, p<0.05; , p<0.01; *, p<0.001; ns=not significant, using a two-tailed Mann-Whitney test.

Figure 6A:
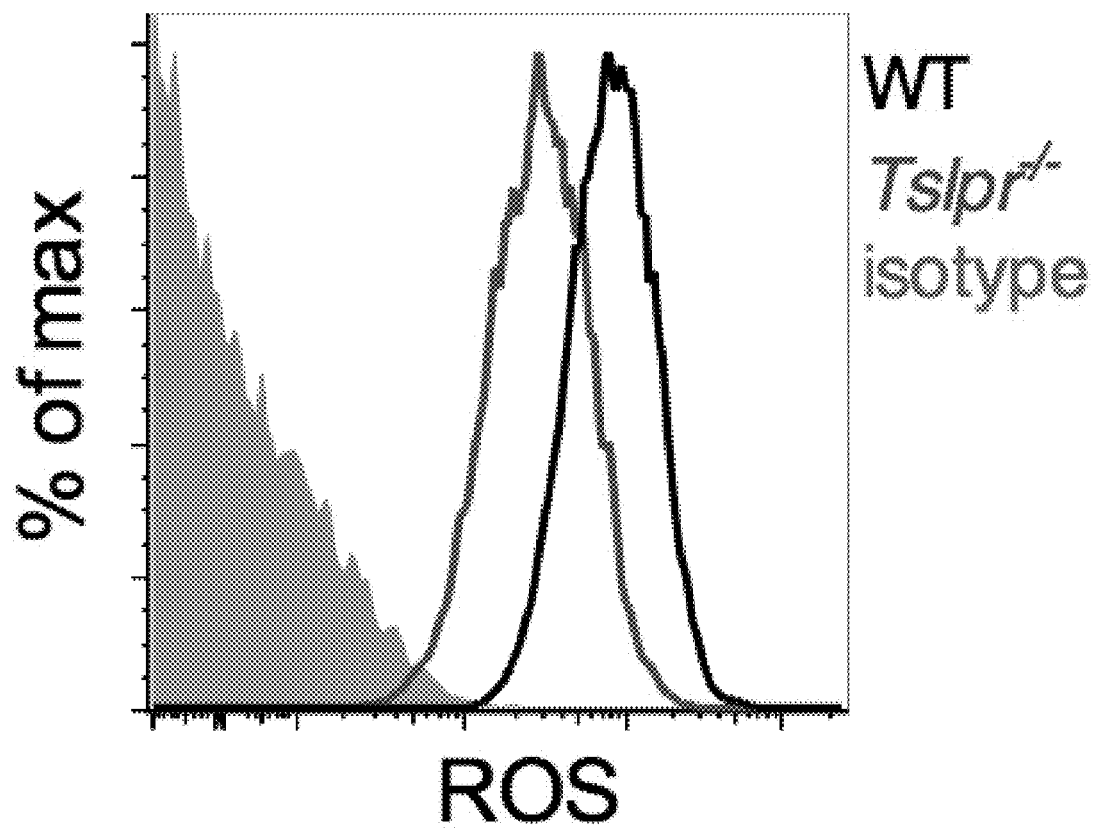
Figure 6B:
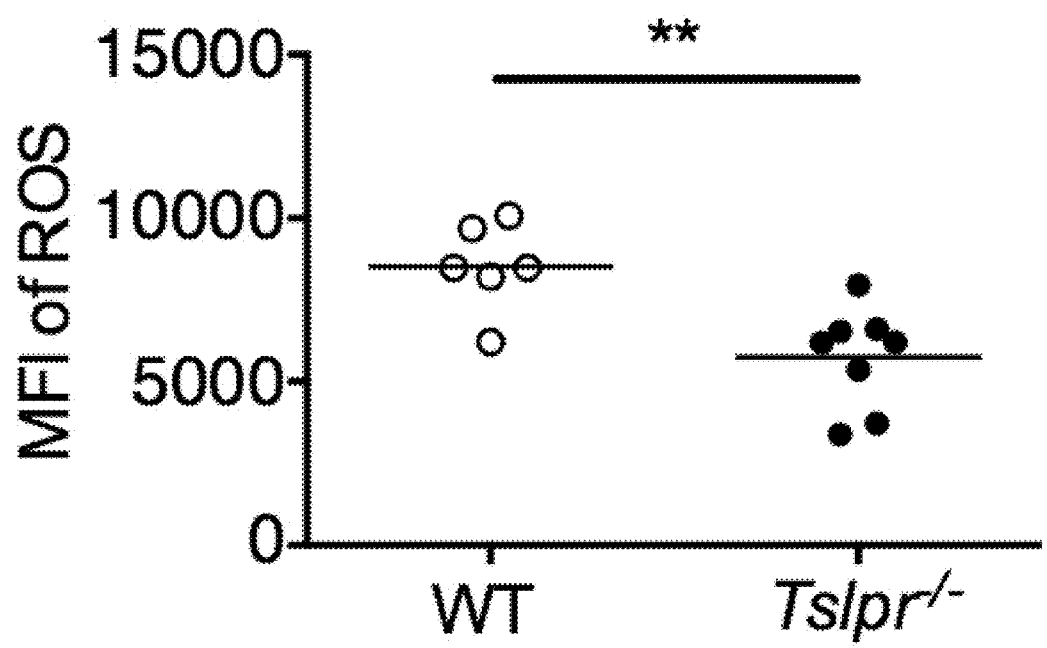
Figure 6D:
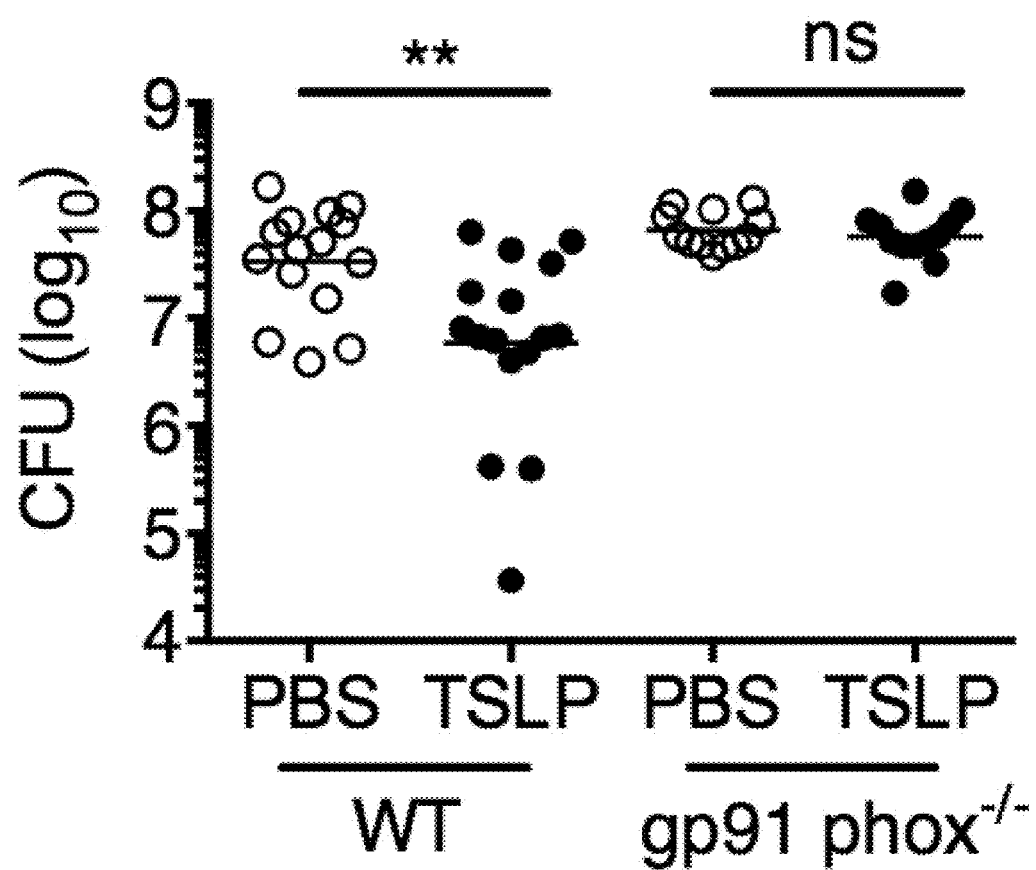
Figure 6E:
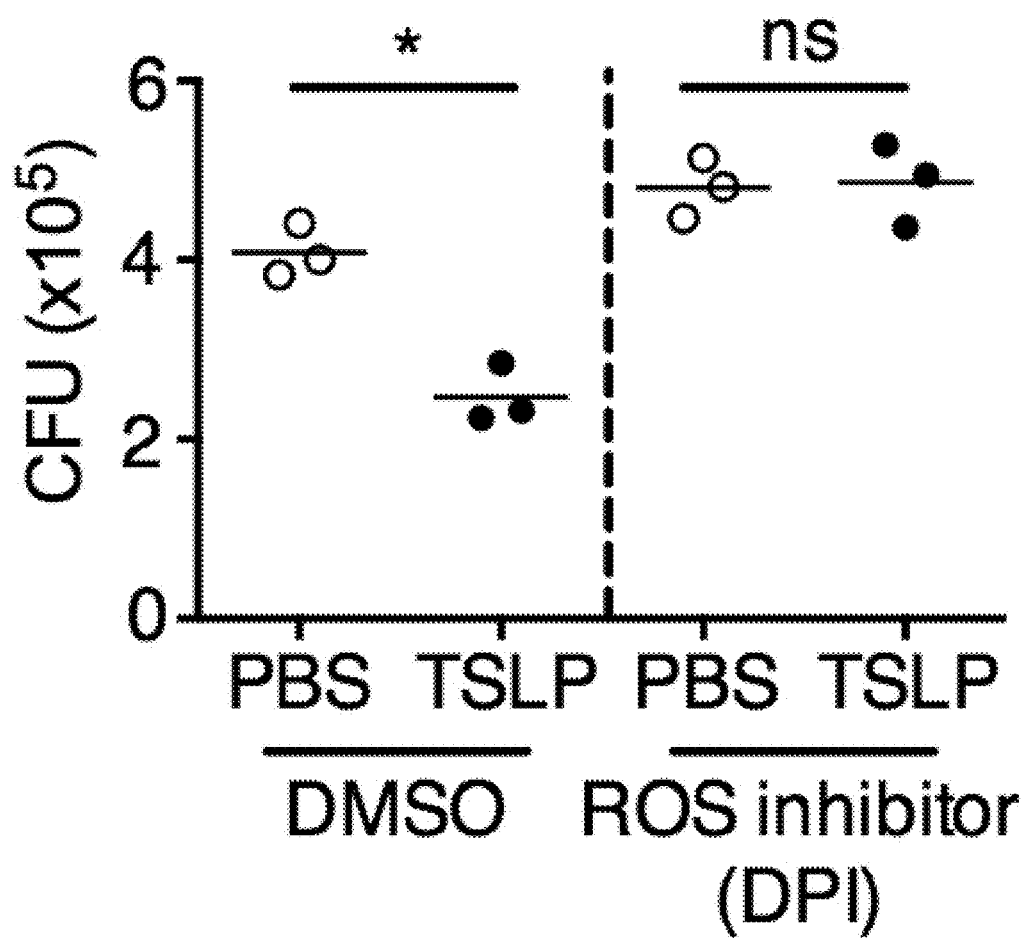

FIG. 6A through FIG. 6E: TSLP induced killing of MRSA is mediated by reactive oxygen species. (FIG. 6A-FIG. 6C) Day 1 p.i. of mice infected with MRSA i.d. in the ear. (FIG. 6A-FIG. 6B) ROS production of mouse neutrophils after staining with CellROX deep red. Shown are a representative FACS plot (FIG. 6A) and mean fluorescence intensity (MFI) (FIG. 6B) of WT (n=6) and Tslpr$^{-/-}$ mice (n=8 ears). (FIG. 6C) Mice were injected i.d. in the ear with MRSA and either PBS or TSLP along with either control (PBS) or a ROS inhibitor (NAC). CFU on day 1 p.i. (two-tailed Mann-Whitney test, n=16 ears). (FIG. 6D) CFU in the ear on day 2 p.i. of WT and Gp91 phox$^{-/-}$ mice infected with MRSA and PBS or TSLP (two-tailed Mann-Whitney test, n=12-16 ears). (FIG. 6E) Purified human neutrophils were pretreated with DMSO or DPI, treated with PBS or TSLP, and incubated for 2 h with MRSA. CFU was then determined (representative donor shown in triplicate, statistics shown are using a two-tailed paired-t test of 3 donors, 3 independent experiments). *, p<0.05; , p<0.01; *, p<0.001; ns=not significant. (b) Two-tailed Student's t-test. Data are representative of 3 independent experiments (FIG. 6A, FIG. 6B) or are combined data from two independent experiments (FIG. 6C and FIG. 6D).

Figure 7B:
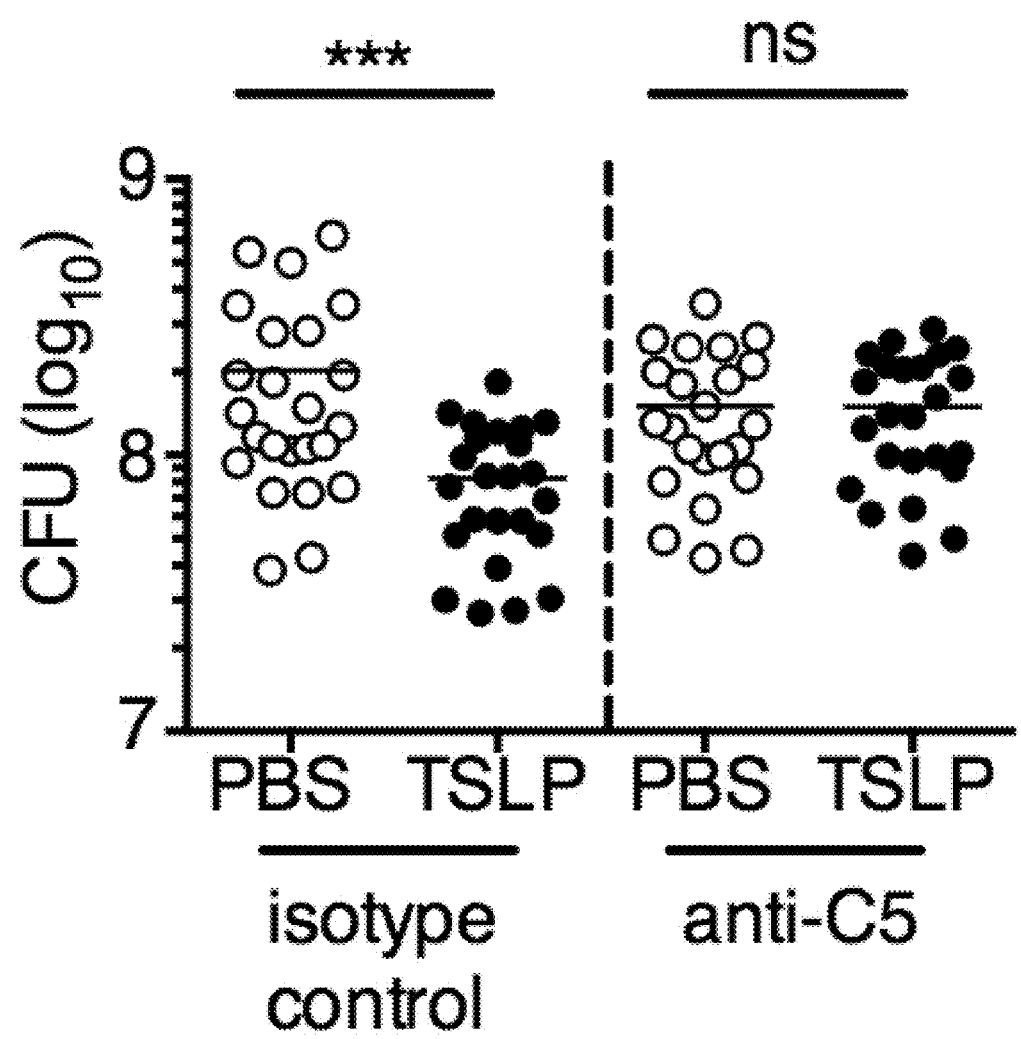
Figure 7C:
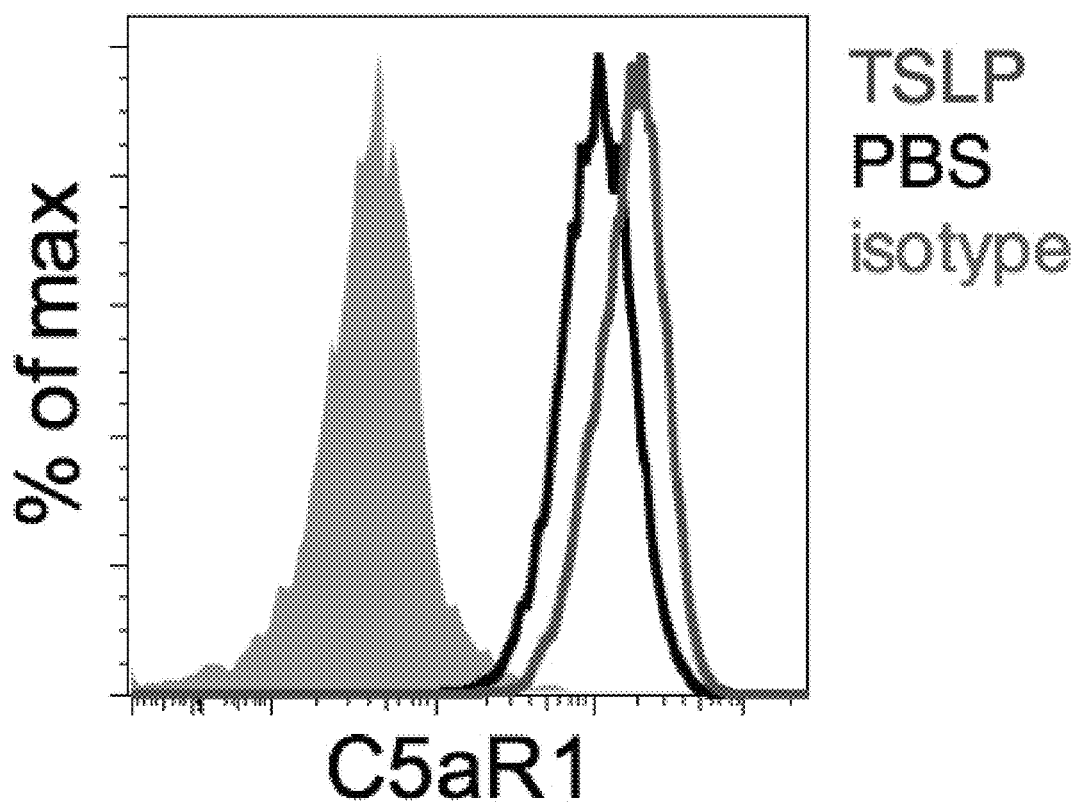
Figure 7D:
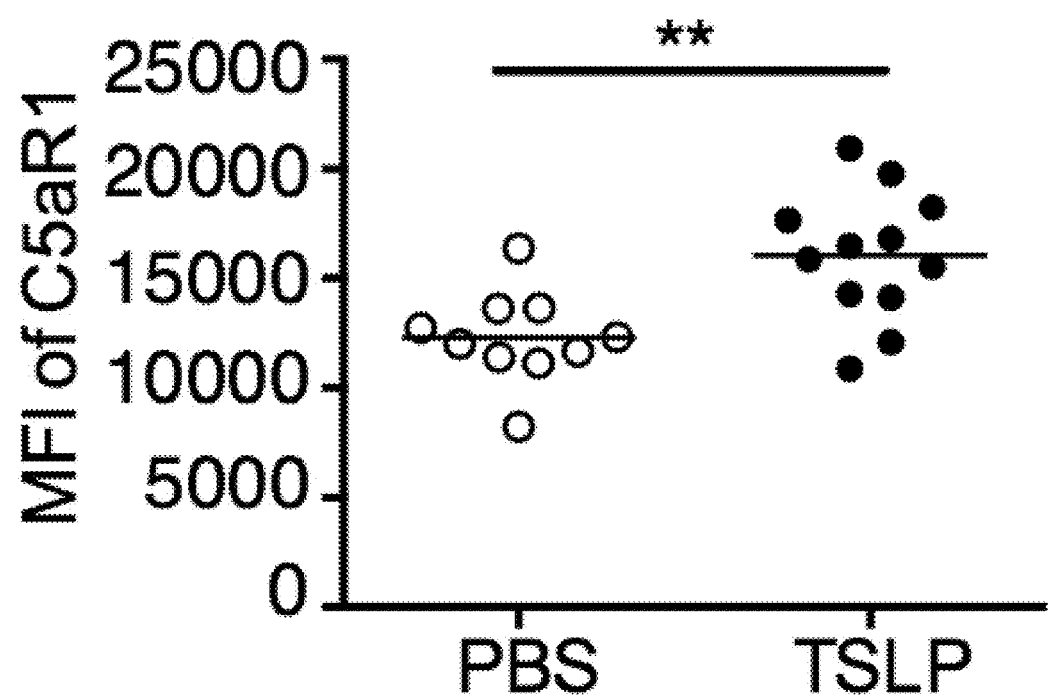
Figure 7E:
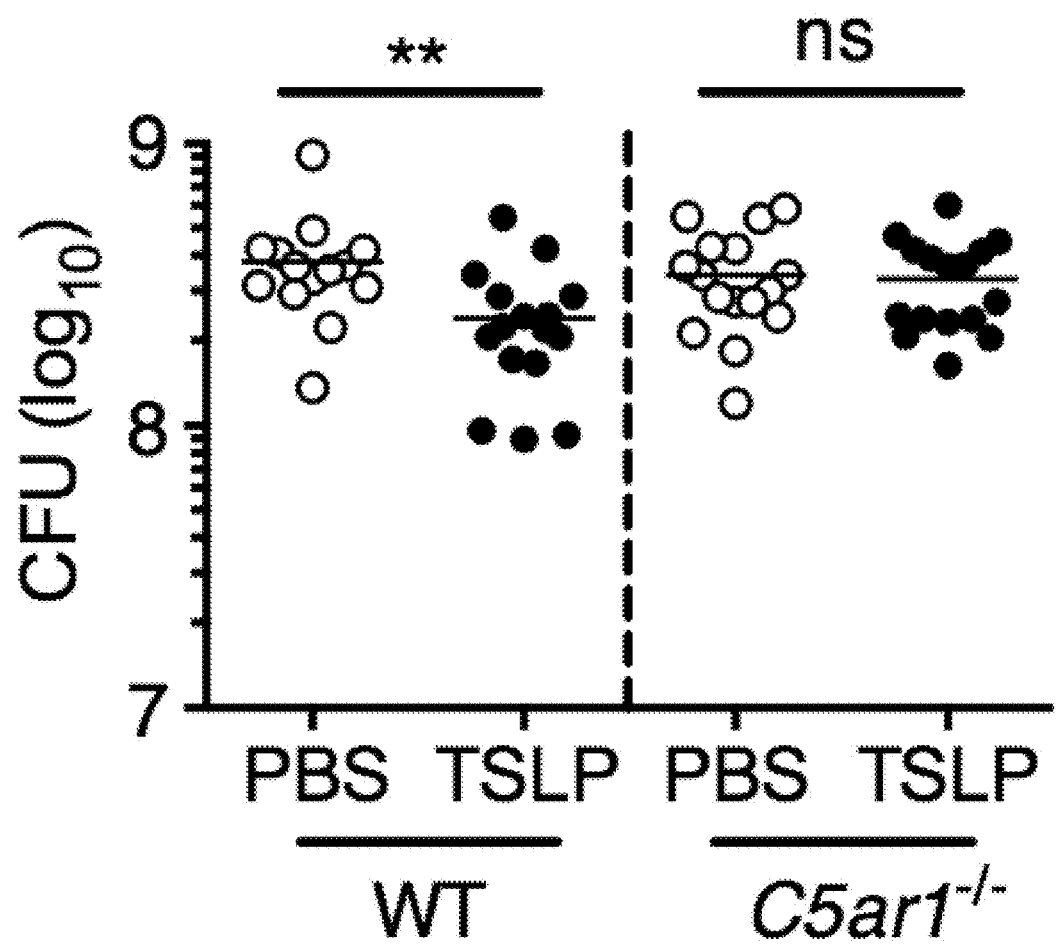

FIG. 7A through FIG. 7G: TSLP induced killing of MRSA is mediated by reactive oxygen species and complement. (FIG. 7A-FIG. 7G) Day 1 p.i. of mice infected with MRSA i.d. in the ear. (FIG. 7A) MFI of ROS production of mouse neutrophils after day 1 p.i. with MRSA plus isotype control (n=15) or anti-C5 antibodies injected i.d. (n=16 ears). (FIG. 7B) Mice were infected with MRSA and PBS or TSLP with isotype control or anti-C5 antibodies given i.d. in the ear. CFU on day 1 p.i. (two-tailed Mann-Whitney test, n=15 (PBS isotype) or n=16 ears). (FIG. 7C-FIG. 7D) C5aR1 expression on mouse neutrophils as assessed by flow cytometry. Shown are a representative FACS plot (FIG. 7C) and MFI for multiple animals (FIG. 7D) (n=10 (WT) or 12 (TSLP) ears. (FIG. 7E) CFU at day 1 p.i. of WT or C5ar1$^{-/-}$ mice infected with MRSA and PBS or TSLP (n=10 (PBS WT) or 16 (all other groups) ears. (FIG. 7F) Purified human neutrophils were treated with DMSO or PMX-53 and PBS or TSLP and incubated for 2 h with MRSA. CFU was then determined (n=5 donors, two-tailed paired-t test of 4 independent experiments). (FIG. 7G) Purified human neutrophils were incubated with PBS or TSLP for 30 min and supernatants were assessed for C5a protein (n=6 donors, ratio-paired two-tailed student's t-test, 3 independent experiments). *, p<0.05; , p<0.01; *, p<0.001; ns=not significant. (FIG. 7A) Two-tailed Student's t-test. Data are representative of 3 independent experiments (FIG. 7A, FIG. 7C-FIG. 7D) or 3 combined independent experiments shown in (FIG. 7B) and 2 in (FIG. 7E).

Figure 8A:
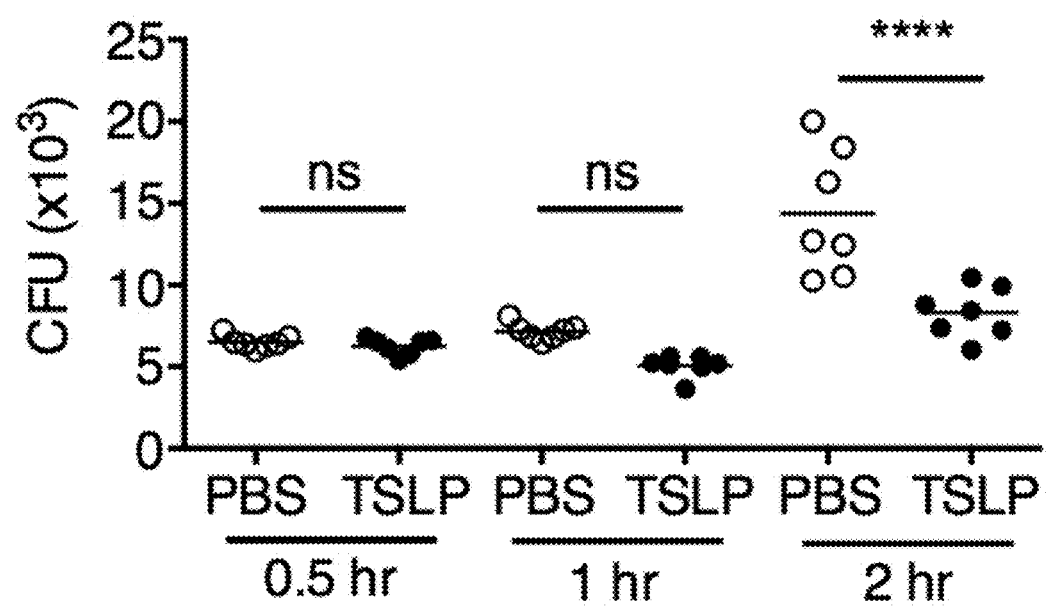
Figure 8C:
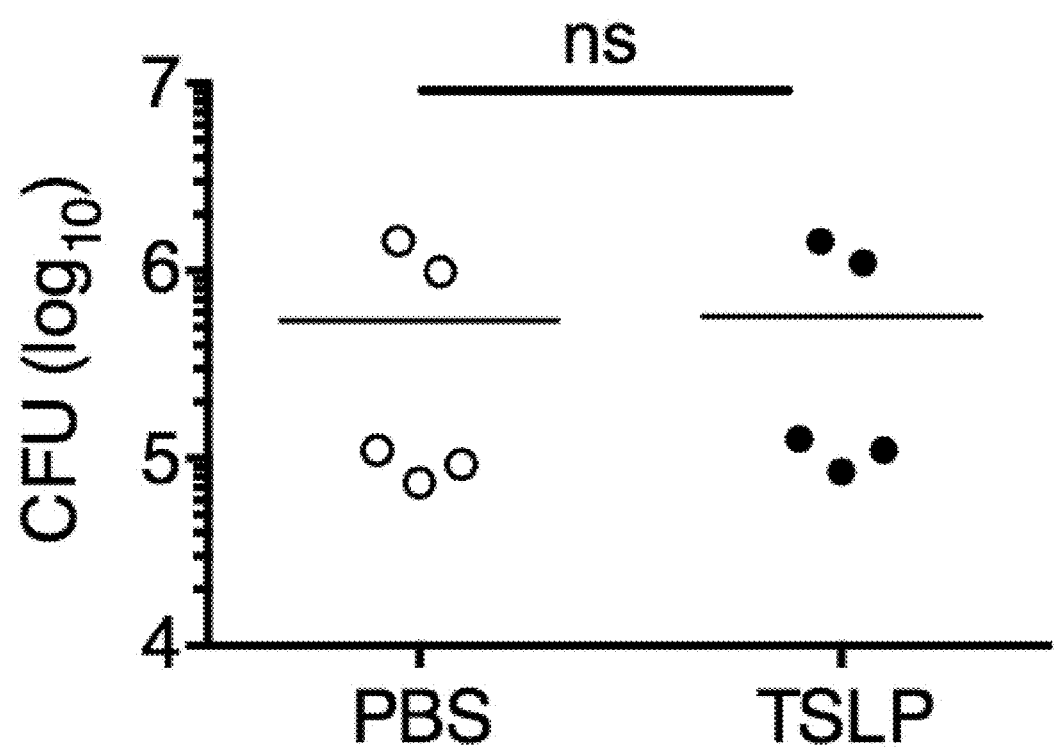
Figure 8D:
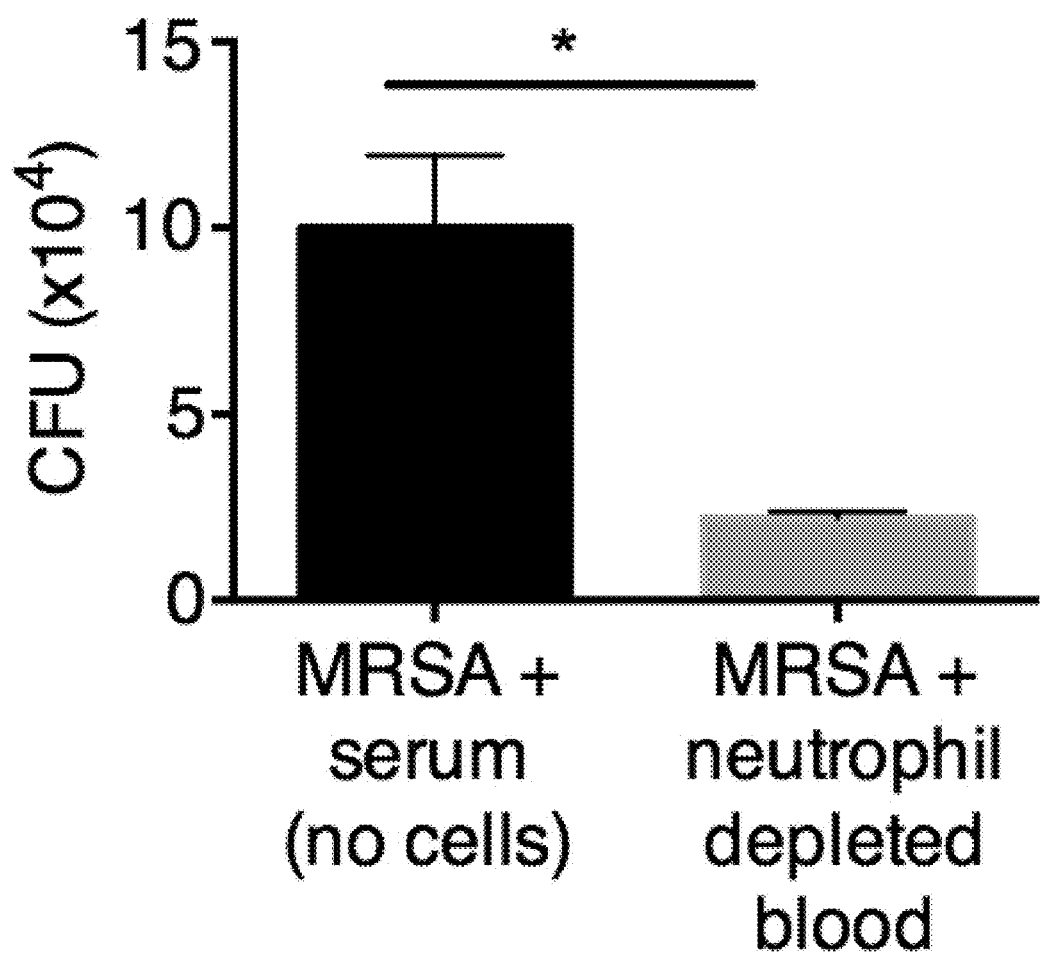

FIG. 8A through FIG. 8D: TSLP does not directly kill MRSA, and normal neutrophil-depleted blood can still reduce MRSA burden. (FIG. 8A, FIG. 8B) Mouse blood was incubated with PBS or TSLP and MRSA for (FIG. 8A) 0.5, 1 and 2 h or (FIG. 8B) 4 h and CFU determined (n=7, data combined from 2 experiments). (FIG. 8C) Mouse serum was incubated with MRSA and either PBS or TSLP for 3 h and CFU determined (n=5, data combined from 3 experiments). (FIG. 8D) CFU of MRSA incubated with serum (i.e., no blood cells were present) or after an in vitro whole blood killing assay was performed with blood from mice treated with anti-Ly6G antibodies. For each assay, blood was combined from 3 mice and assays were performed in triplicate. ns, not significant; ****, p<0.0001 One way ANOVA (A, B); *, p<0.05 using two-tailed Student's t-test (FIG. 8C, FIG. 8D).

Figure 9A:
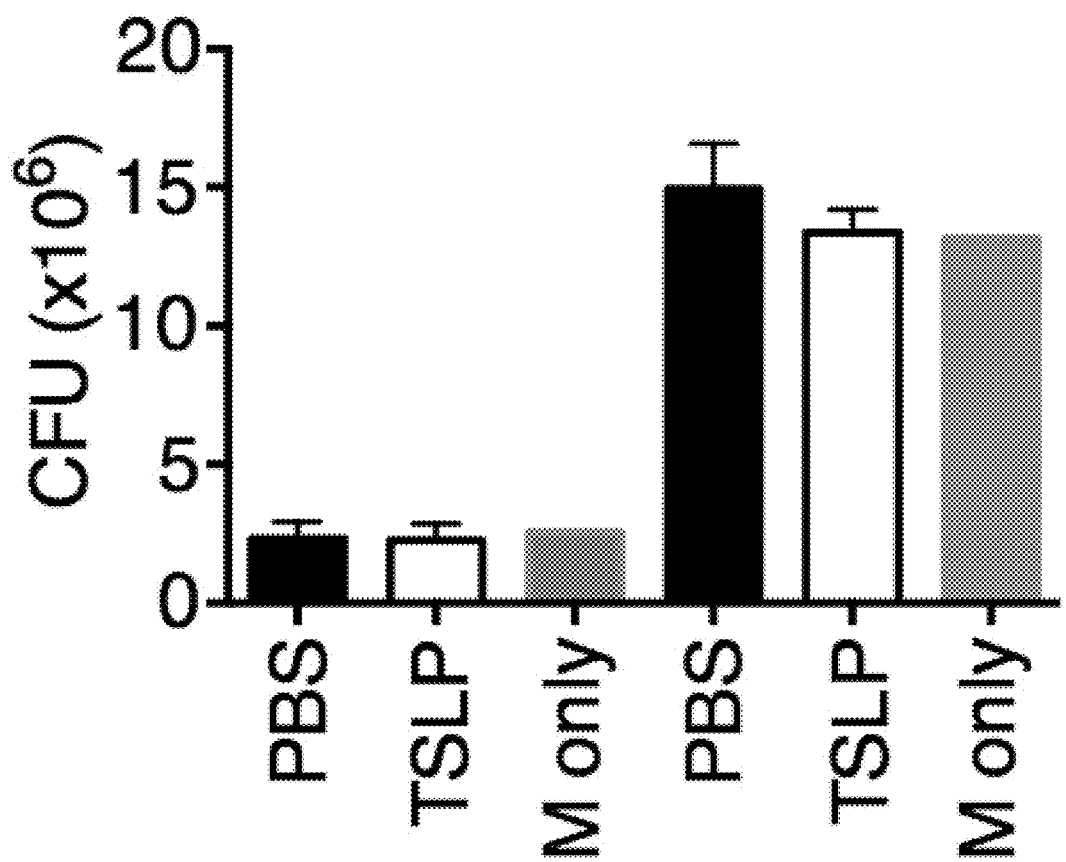
Figure 9B:
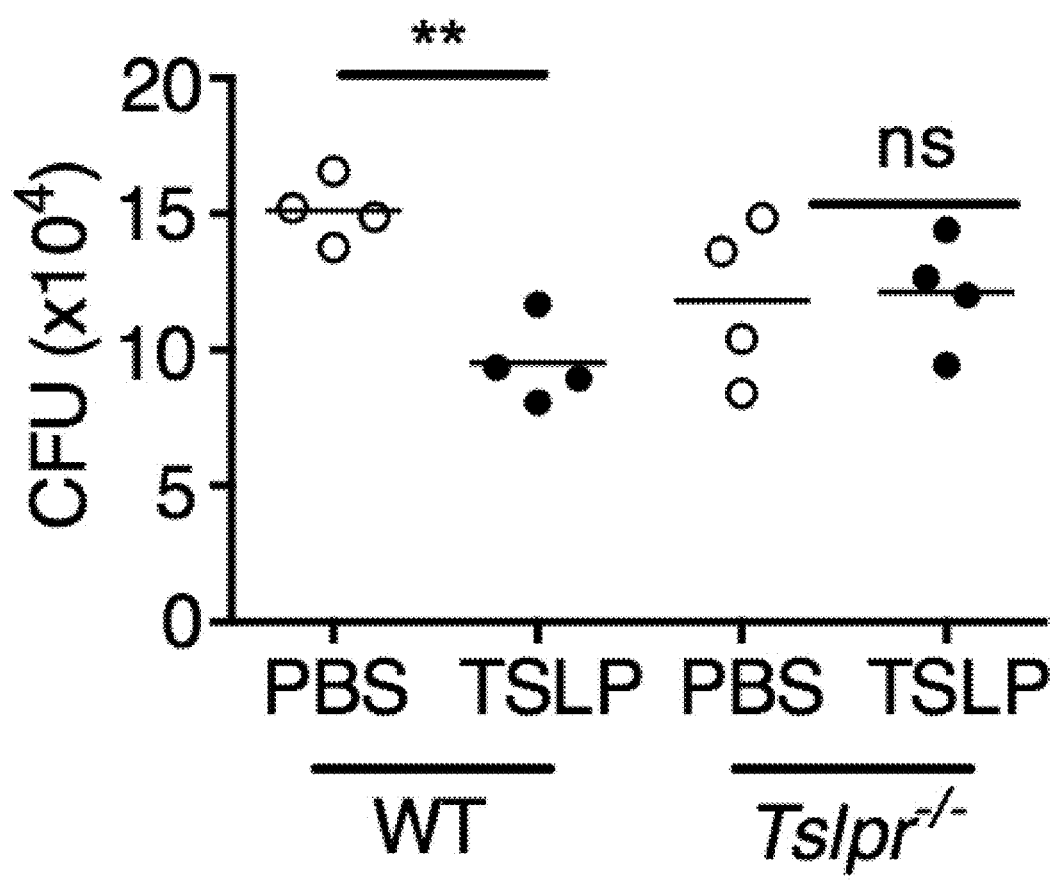
Figure 9D:
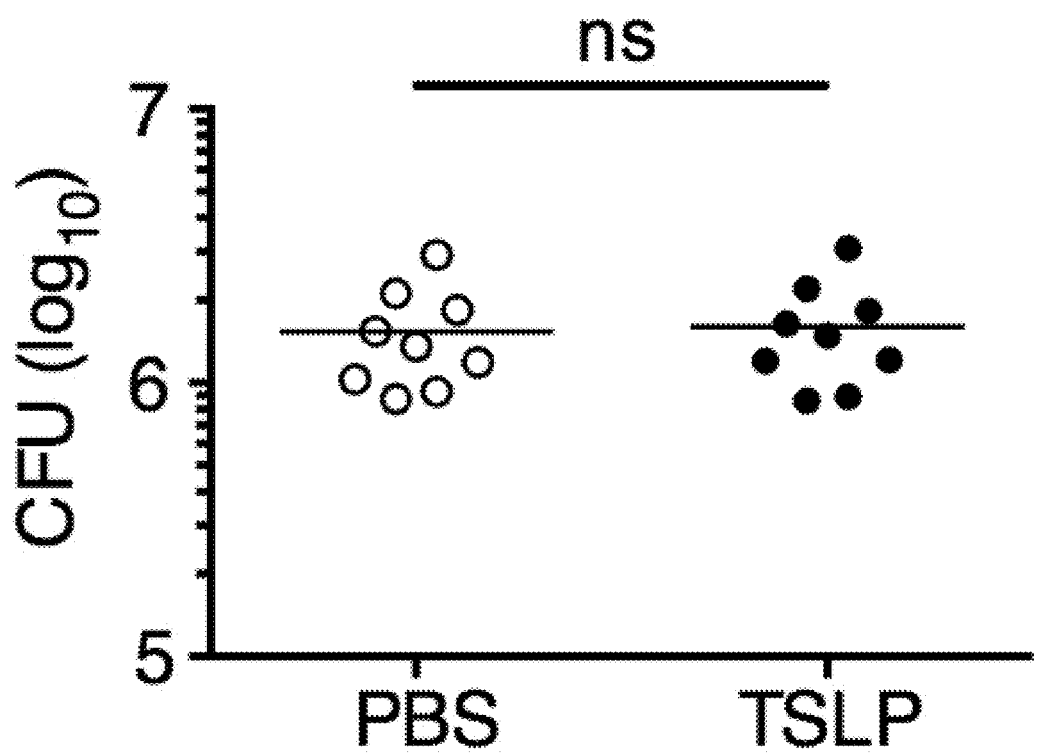

FIG. 9A through FIG. 9G: TSLP requires TSLPR and acts on human neutrophils to increase control of MRSA. (FIG. 9A) Bone marrow neutrophils were isolated from naïve mice and incubated with PBS or TSLP and MRSA for 2 or 4 hours, and CFU was enumerated. "M only" indicates tubes that only received MRSA (no cells). (FIG. 9B) CFU after thioglycollate-elicited purified neutrophils from WT or Tslpr$^{-/-}$ mice were incubated with PBS or TSLP and MRSA for 2 h. (FIG. 9C) Whole human blood was incubated with MRSA and either PBS or TSLP for 3 h and CFU determined (n=6). (FIG. 9D) MRSA was incubated with human serum (i.e., without cells) plus PBS or TSLP for 3 h and CFU determined (n=9). (FIG. 9E) CRLF2 expression by purified human blood neutrophils determined by RT-PCR after 4 h treatment with medium alone or with peptidoglycan (PGN) and normalized to expression of RPL7 (data from two individual donors combined). (FIG. 9F, FIG. 9G) Purified human neutrophils (FIG. 9F) or human neutrophils primed with HKSA plus either PBS or TSLP for 2 h (FIG. 9G) were incubated with MRSA and PBS or TSLP, and CFU assessed after 3 h (FIG. 9F) (n=7) or 2 h (FIG. 9G) (n=4). *, p<0.05; ns, not significant using the two-tailed paired Student's t-test (FIG. 9C, FIG. 9E-FIG. 9G); for FIG. 9C, FIG. 9F and FIG. 9G each line represents 1 donor. Two-tailed Student's t-test (FIG. 9D). Data were representative of 3 individual mice (FIG. 9A) or from either 5 (FIG. 9C, FIG. 9F) or 3 (FIG. 9D, FIG. 9G) combined experiments.

Figure 10A:
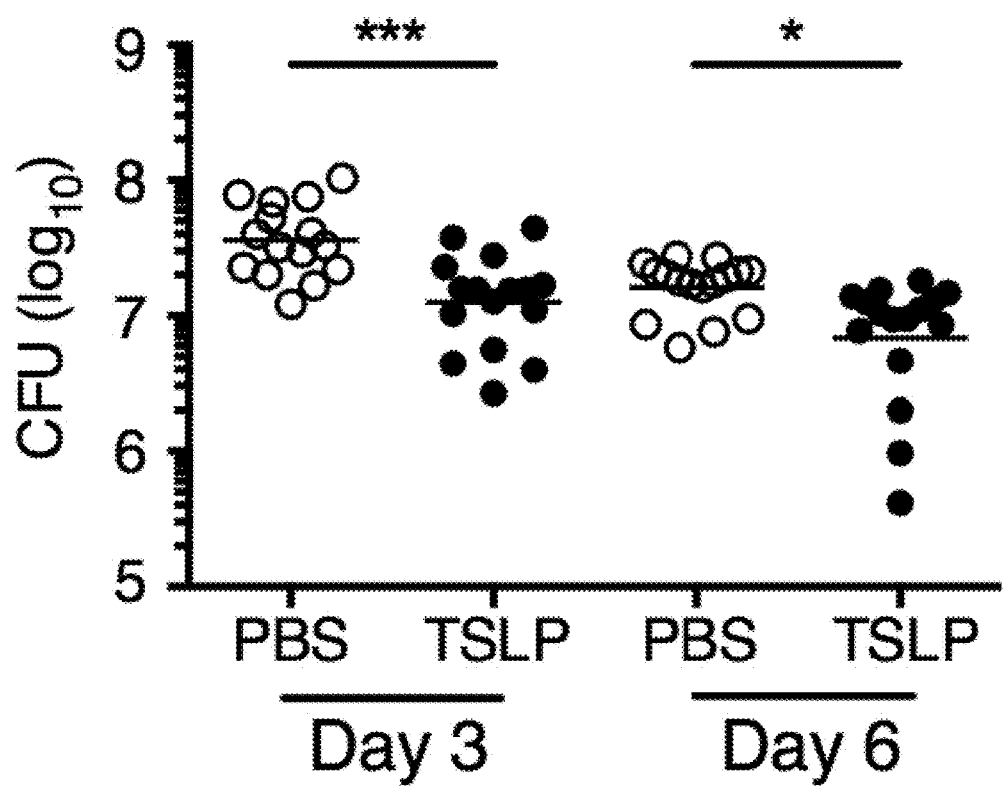
Figure 10B:
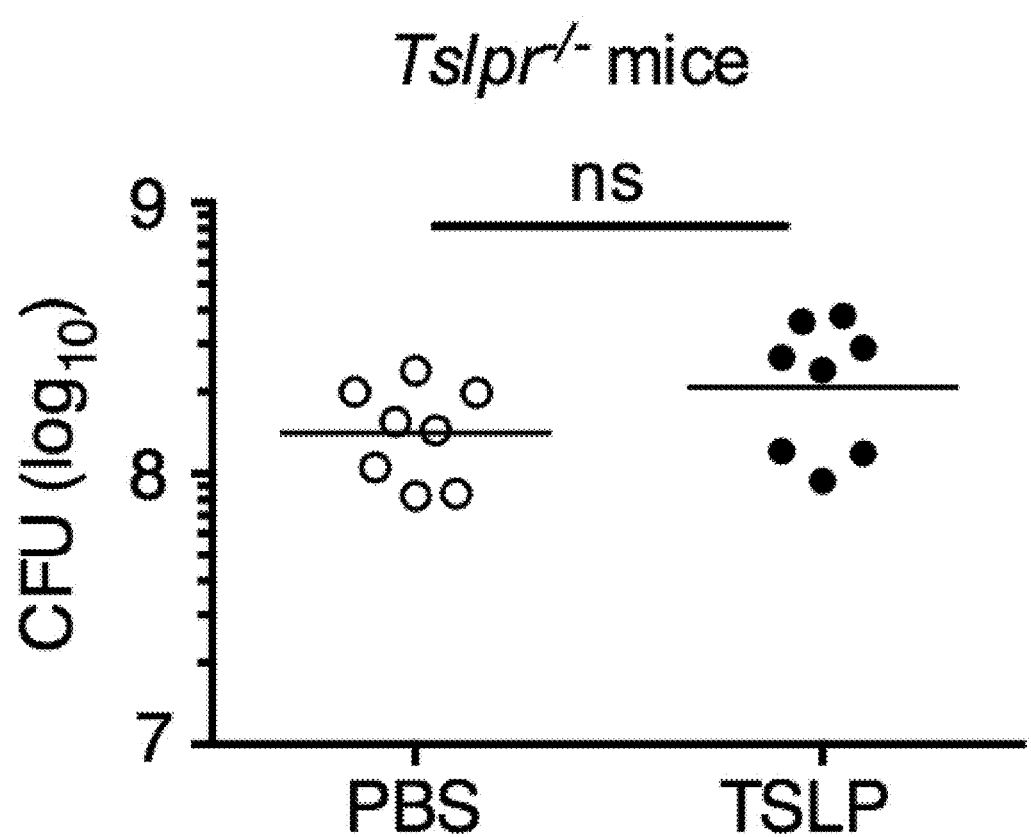
Figure 10C:
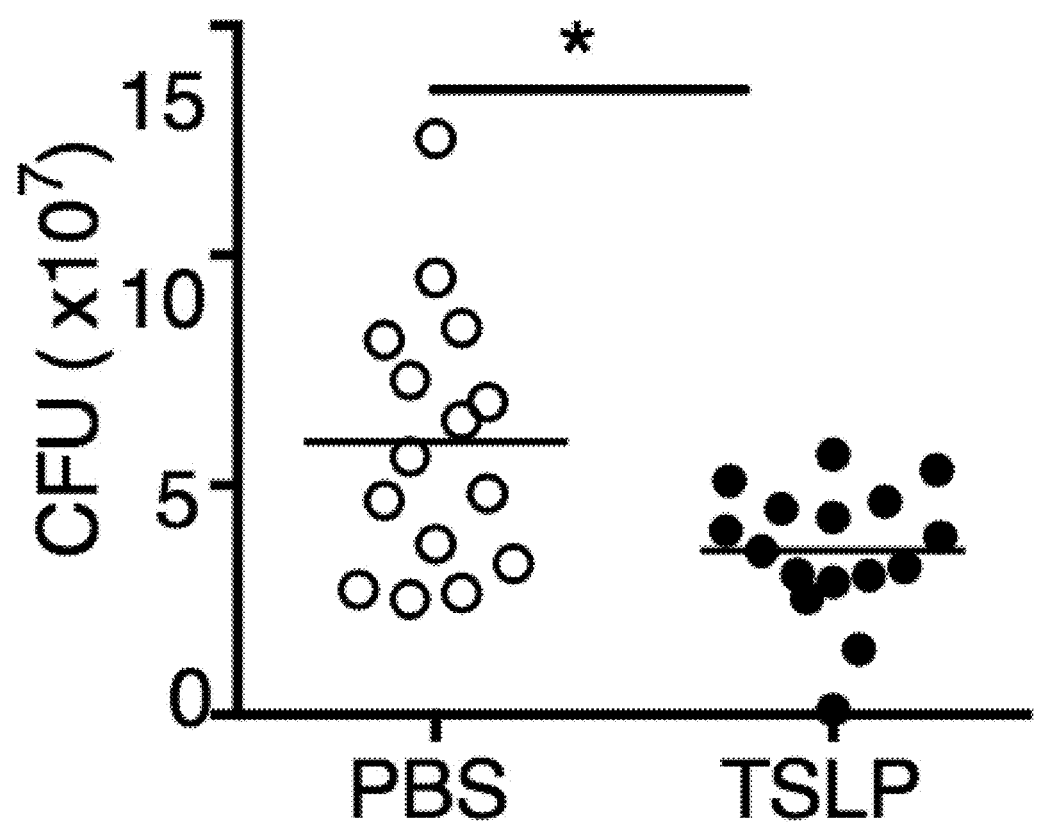

FIG. 10A through FIG. 10C: TSLP is TSLPR-dependent and enhances the killing of both MRSA and *S. aureus* in vivo. Mice were infected with MRSA i.d. in the ear. (FIG. 10A) CFU of MRSA at days 3 and 6 p.i. in the ears of WT mice treated with PBS or TSLP (Kruskal-Wallis ANOVA with Dunn's multiple comparison test). (FIG. 10B) TSLPR$^{-/-}$ mice were injected in vivo i.d. with MRSA plus either PBS or TSLP and CFU determined at day 1 p.i. (n=8, representative of 2 experiments, two-tailed Student's t-test). (FIG. 10C) CFU of *S. aureus* at day 2 p.i. in the ears of WT mice treated with PBS or TSLP and infected i.d. with *S. aureus* strain MW2 (Mann-Whitney test). ns, not significant. *, p<0.05; , p<0.01; **, p≤0.0001.

Figure 11A:
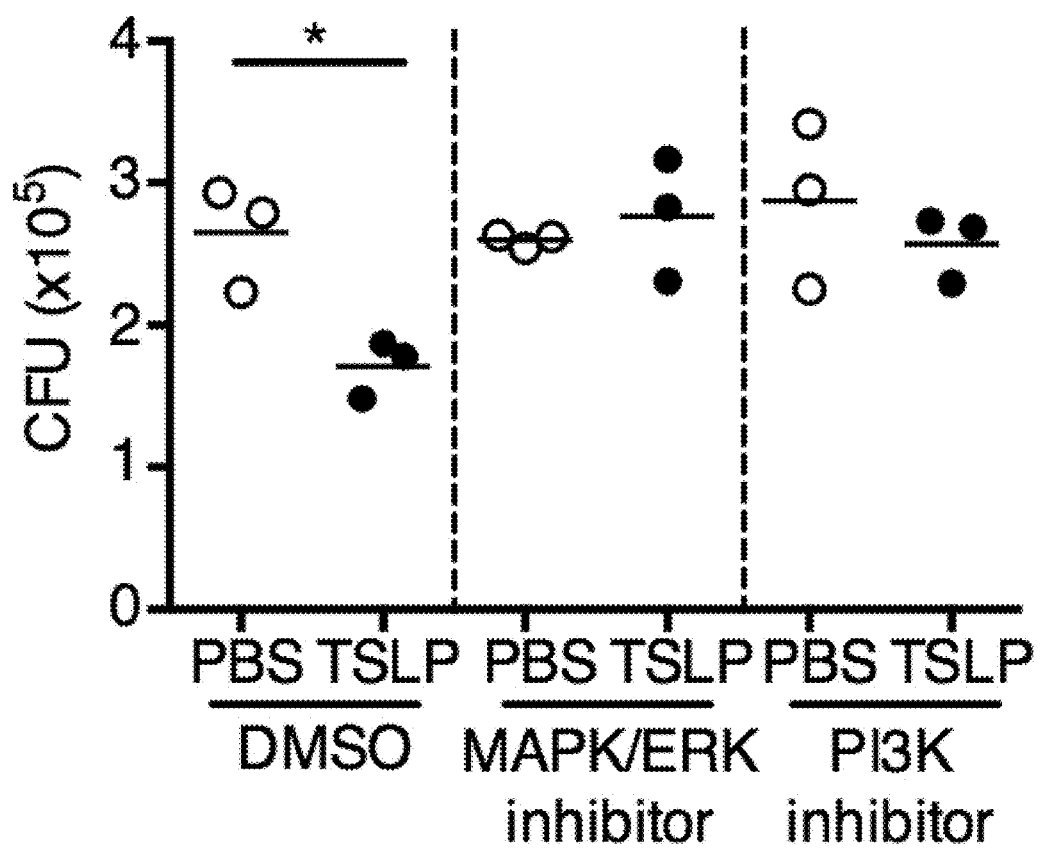
Figure 11B:
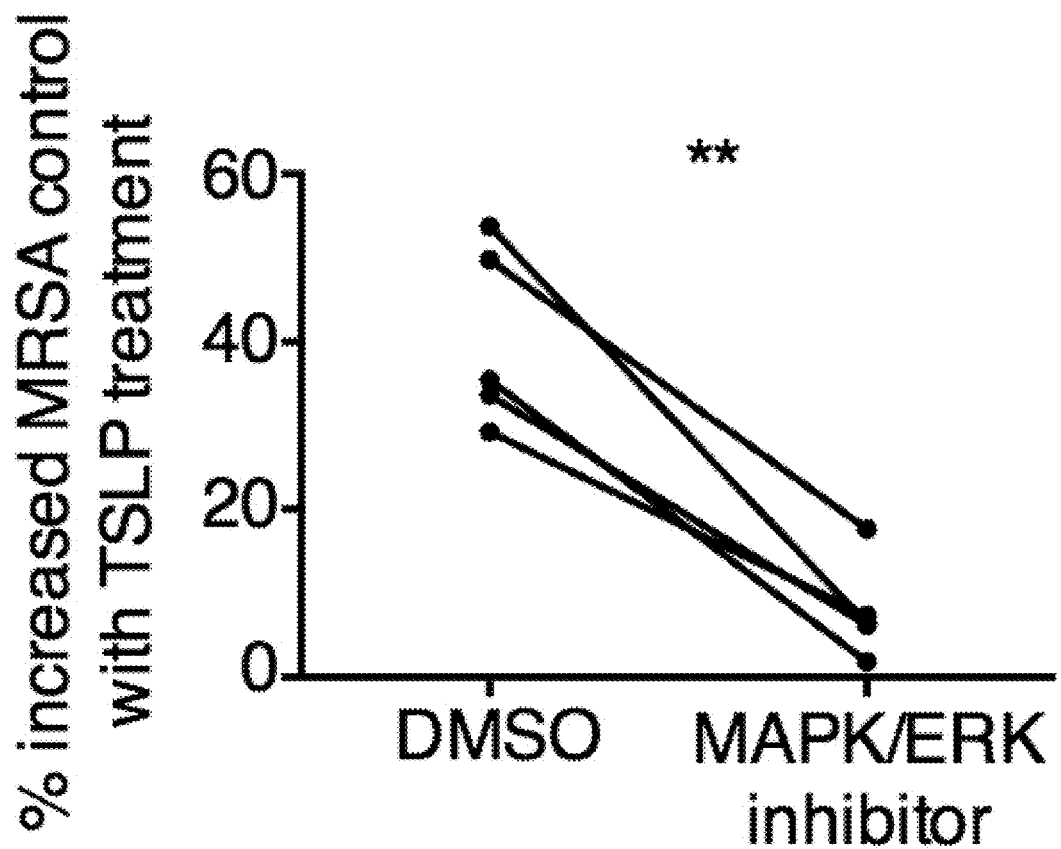
Figure 11C:
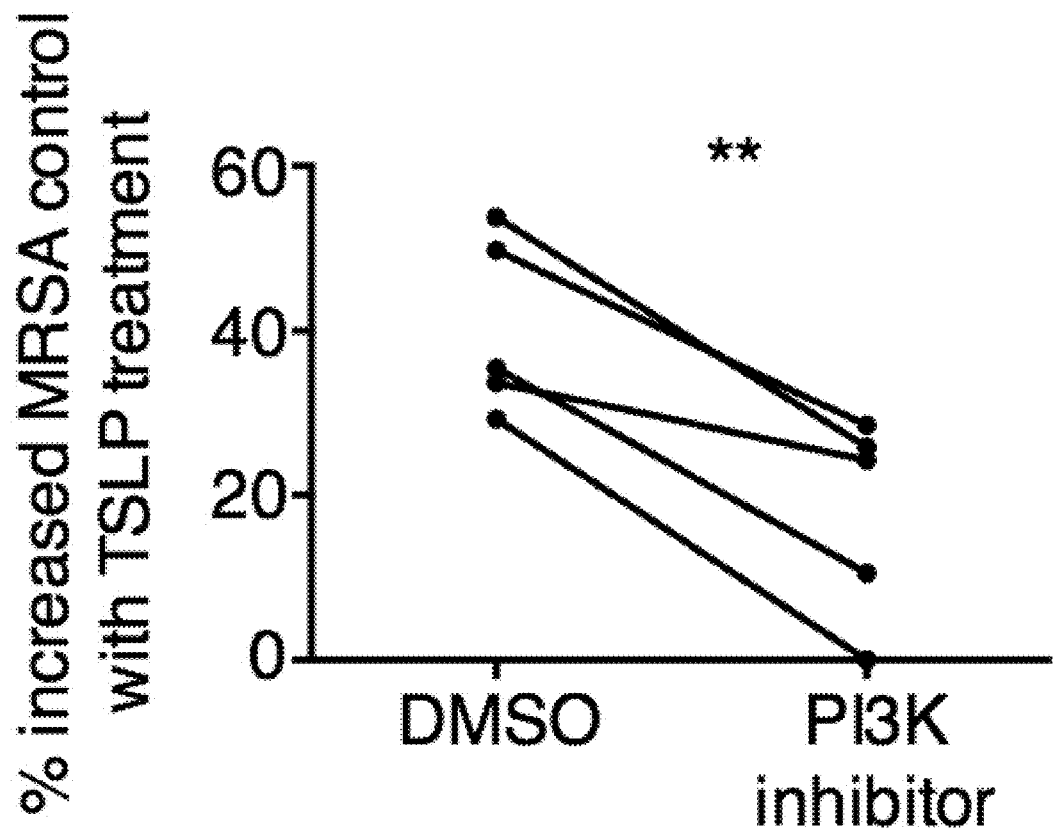

FIG. 11A through FIG. 11D: TSLP treatment increases killing of MRSA by human neutrophils in a PI3K- and MAPK/ERK-dependent manner.☐ Purified human neutrophils were pretreated with MAPK/ERK kinase inhibitor (PD98059) or PI3K inhibitor (LY294002), incubated with MRSA plus either PBS or TSLP for 2 h, and CFU determined. (FIG. 11A) Representative donor shown (performed in triplicate). (FIG. 11B and FIG. 11C) Percent increased control of MRSA with TSLP shown for 5 individual donors. Treatment with MAPK/ERK kinase inhibitor (FIG. 11B) or PI3K inhibitor (FIG. 11C) each diminished control of MRSA. (FIG. 11D) Neutrophils were pretreated with DMSO, MAPK/ERK kinase inhibitor (PD98059), or PI3K inhibitor (LY294002), then incubated with MRSA and CFU determined, as compared to MRSA incubated with serum alone (i.e., no cells) for 2 h. Data are representative of 3 independent experiments. *, p<0.05; , p<0.01; **, p≤0.0001 using ANOVA (FIG. 11A, FIG. 11D) or two tailed paired Student's t-test (FIG. 11B, FIG. 11C).

FIG. 12A through FIG. 12F: TSLP treatment of mouse or human neutrophils does not affect phagocytosis. (FIG. 12A) Purified thioglycollate-elicited neutrophils were pre-treated either with DMSO or cytochalasin D for 15 min and then incubated with PBS or TSLP and MRSA. CFU were enumerated 2 h later. (FIG. 12B) CD11b expression (MFI) on human blood neutrophils incubated for 30, 60, and 120 min with medium (control), TSLP, HKSA, or HKSA+TSLP (n=3). (FIG. 12C) CD11b expression (MFI) on mouse ear neutrophils from WT mice or Tslpr$^{-/-}$ mice 1 day p.i. with i.d. MRSA; WT animals were treated with PBS or TSLP as indicated (n=8). (FIG. 12D) Purified human neutrophils were incubated with pHrodo Green *S. aureus* BioParticles and the % phagocytosed bacteria was determined 30 min later by flow cytometry (n=2). (FIG. 12E, FIG. 12F) Neutrophils isolated from WT and Tslpr$^{-/-}$ bone marrow (FIG. 12E) or WT mouse bone marrow (FIG. 12F) were incubated with pHrodo Green *S. aureus* Bioparticles, and the % phagocytosed bacteria determined by flow cytometry after 20 (FIG. 12E) (n=2) or 5 (FIG. 12F) min (n=2). For WT BM, either PBS or TSLP was added as indicated.

FIG. 13A through FIG. 13E: ROS- and complement-dependent TSLP-enhanced neutrophil killing. (FIG. 13A) Mouse blood was combined with MRSA and either PBS or TSLP in the presence of EDTA for 3 h, and CFU was then determined (n=3). (FIG. 13B and FIG. 13C) WT mice were injected i.d. in the ear with MRSA plus either PBS or TSLP and either isotype control or anti-05 antibodies. Shown are percent (FIG. 13B) and total number (FIG. 13C) of neutrophils in the ear at day 1 p.i. (n=8 ears). (FIG. 13D and FIG. 13E) CFU determined after neutrophils were (FIG. 13D) pretreated with DMSO or DPI or (FIG. 13E) treated with DMSO or PMX-53 and then incubated with MRSA, compared to MRSA incubated in serum only (no cells) for 2 h. ****, p≤0.0001 using ANOVA. Representative of 3 independent experiments.

Figure 14:
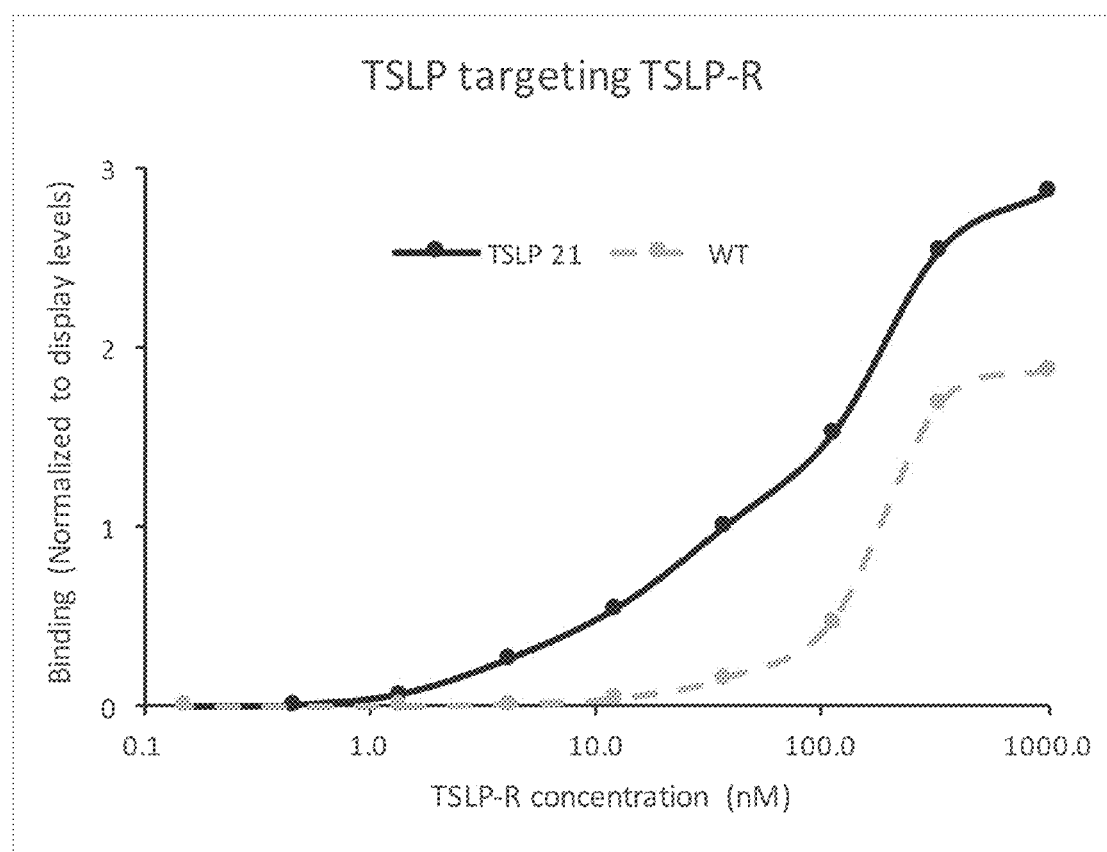

FIG. 14 presents data showing the affinity of WT vs. a mutant form of TSLP (SEQ ID NO:10) for the TSLP receptor.

DETAILED DESCRIPTION OF THE INVENTION

In one embodiment, the invention provides a method of promoting the host defense of a patient to a bacterial infection. In accordance with the inventive method, a pharmaceutical composition comprising an effective amount of a TSLP protein or polypeptide is administered to a patient in need of such treatment. Naturally, in humans, TSLP is highly expressed at barrier surfaces, including the skin, and TSLP plays a deleterious role in the promotion of allergic responses. However, its role in host-defense against bacterial infections heretofore has not been elucidated.

In this context, a patient "in need" of treatment in accordance with the inventive method is a patient suffering from or at risk of a bacterial infection, particularly a pathogenic bacterial infection. In this context, a pathogenic bacterial infection is an infection by a bacterium that damages the tissue of the patient, or which causes a pathological condition, such as sepsis. A pathogenic bacterial infection, thus, is distinguished from beneficial or symbiotic bacterial colonization (e.g., intestinal flora).

A patient to be treated in accordance with the inventive method can be at risk of a pathogenic bacterial infection even if not currently infected at the time the treatment is administered. For example, as many bacterial infections are nosocomial, a patient can be at risk for a pathogenic bacterial infection by being present in a health-care facility, such as a hospital, clinic, or the like, or in an area of intensified or indiscriminate antibacterial usage, such as many farm environments. Patients who are candidates for surgery also are at risk of a pathogenic bacterial infection, as are patients experiencing other diseases or disorders, such as pneumonia, sepsis, and the like. Elderly patients, very young patients, and immunocompromised patients also can be said to be at risk of a bacterial infection, particularly a pathogenic bacterial infection.

It will be observed that the method can be applied to human patients as well as veterinary patients (especially mammals), and also to laboratory animals (especially mammals) (which can be considered "patients" in the context of the present invention). Preferably, the patient is human.

In accordance with the inventive method, a pharmaceutical composition comprising a TSLP protein or polypeptide is administered to the patient. The pharmaceutical composition is administered in an amount and at a location sufficient to promote the host defense of the patient to the bacterial infection. The amount of pharmaceutical composition to be administered will depend on the route of administration, the severity of the bacterial infection within the patient, and the concentration of the active agent (TSLP protein or polypeptide) within the composition, among other parameters as discussed below. However, it will be within the purview of the treating physician, veterinarian or laboratory researcher, as appropriate to the patient, to select a suitable amount of the pharmaceutical composition for administration to the patient in accordance with the inventive method. An effective amount of the pharmaceutical composition can be titrated by assaying the effect of administration of increasing amounts of the composition on the ability of neutrophils obtained from the patient to kill MRSA (or another bacterium of interest).

The location at which the pharmaceutical composition comprising a TSLP protein or polypeptide is administered in accordance with the inventive method will vary in accordance with the type of bacterium, the nature of the infection, and the formulation of the pharmaceutical composition. For example, the formulation comprising the TSLP protein or polypeptide can be formulated for application (e.g., topically) to a barrier tissue of the patient, such as conjunctiva, nasal epithelium, oral epithelium, rectal epithelium, skin, vaginal epithelium, and the like, and therefore be applied topically to such tissue in accordance with the inventive method. It will be understood that such barrier tissue can be intact or broken (e.g., ruptured or wounded), and that the inventive method can be employed regardless of the integrity of the barrier tissue. Furthermore, in accordance with the present invention, the pharmaceutical composition comprising the TSLP protein or polypeptide can be applied to an abscess or boil, such as which often forms as a result of a bacterial (e.g., MRSA) infection of barrier tissue such as skin. In other embodiments, the pharmaceutical composition comprising the TSLP can be formulated for intravenous or intraperitoneal administration, and thus administered to the systemic blood circulation of the patient, a body cavity, an organ, or another desired location within the patient.

The inventive method can be employed against a variety of types of bacterial infections. For example, the bacterial infection can result from a Gram positive or Gram negative bacterium (or a combination of several types of bacteria). Exemplary pathogenic Gram positive bacteria to be combatted in accordance with the inventive method include species from the genera: *Bacillus, Clostridium, Corynebacterium, Listeria, Staphylococcus* (e.g., *Staphylococcus aureus*), and *Streptococcus* (*Streptococcus pyogenes*), although the inventive method is not limited to treating a patient suffering from or at risk of infection with only these bacterial genera. Exemplary pathogenic Gram negative bacteria to be combatted in accordance with the inventive method include Enterobacteriaceae (including *E. coli, Enterobacter cloacae, Proteus mirabilis, Serratia marcescens*, among others) and species from the genera: *Acinetobacter* (e.g., *Acinetobacter baumannii*), *Helicobacter* (e.g., *Helicobacter pylori*), Hemophilus (e.g., Hemophilus influenza), *Klebsiella* (e.g., *Klebsiella pneumoniae*), *Legionella* (e.g., *Legionella pneumophila*), *Moraxella* (e.g., *Moraxella catarrhalis*), *Neisseria* (e.g., *Neisseria gonorrhoeae, Neisseria meningitides*, etc.), *Salmonella* (e.g., *Salmonella enteritidis, Salmonella typhi*, etc.), *Shigella, Pseudomonas* (e.g., *Pseudomonas aeruginosa*), and *Stenotrophomonas*, although the inventive method is not limited to treating a patient suffering from or at risk of infection with only these bacterial groups, genera, and species. In a preferred embodiment, the bacterial infection is the infection of the patient with MRSA.

As noted herein, the active agent in the pharmaceutical composition for use in the inventive method is the cytokine, TSLP or a functional variant of TSLP (the TSLP protein or polypeptide). Several isoforms of TSLP exist and can be employed as the active agent in the context of the present invention. These include, but are not limited to, proteins or polypeptides comprising, consisting of, or consisting essentially of the following amino acid sequences:

SEQ ID NO:1:
MFPFALLYVLSVSFRKIFILQLVGLVLTYDFTNCD-FEKIKAAYLSTISKDLITYMSGTKST EFNNTVSCSN-RPHCLTEIQSLTFNPTAGCASLAKEMFAMKTKAALAI-WCPGYSETQINAT QAMKKRRKRKVTTNKCLEQVSQLQGLWRRFN-RPLLKQQ. This (SEQ ID NO:1) is the full length human isoform of TSLP, according to UniProtKB/Swiss-Prot: Q969D9.1, which is incorporated herein by reference. The first 28 amino acids are reported as being a signal.

SEQ ID NO:2:
YDFTNCDFEKIKAAYLSTISKDLITYMSGTKSTEF-NNTVSCSNRPHCLTEIQSLTFNPTAG CASLAKEM-FAMKTKAALAIWCPGYSETQINATQAMKKRRKRK-VTTNKCLEQVSQLQG LWRRFNRPLLKQQ. This (SEQ ID NO:2) is amino acids 29-159 of SEQ ID NO:1, i.e., without the first 28 amino acids reported as being a signal.

SEQ ID NO:3:
MYDFTNCDFEKIKAAYLSTISKDLITYMSGTKSTEF-NNTVSCSNRPHCLTEIQSLTFNPTA GCASLAKEM-FAMKTKAALAIWCPGYSETQINATQAMKKRRKRK-VTTNKCLEQVSQLQ GLWRRFNRPLLKQQ. This (SEQ ID NO:3) represents SEQ ID NO:2 with an amino-terminal methionine.

SEQ ID NO:4:
MVLLRSLFILQVLVRMGLTYNFSNCNFTSITKIYCNI-IFHDLTGDLKGAKFEQIEDCESKP ACLLKIEYYTLN-PIPGCPSLPDKTFARRTREALNDHCPGYPE-TERNDGTQEMAQEVQNIC LNQTSQILRLWYSFMQSPE. This (SEQ ID NO:4) is the full length murine isoform of TSLP, according to NCBI Reference Sequence: NP 067342.1, which is incorporated herein by reference. The first 19 amino acids are reported as being a signal.

SEQ ID NO:5: YNFSNCNFTSITKIYCNIIFHDLTGDLK-GAKFEQIEDCESKPACLLKIEYYTLNPIPGCPSLP DKT-FARRTREALNDHCPGYPETERNDGTQEMAQEVQNI-CLNQTSQILRLWYSFMQSPE. This (SEQ ID NO:5) is amino acids 20-140 of SEQ ID NO:4, i.e., without the first 19 amino acids reported as being a signal.

SEQ ID NO:6:
MYNFSNCNFTSITKIYCNIIFHDLTGDLKGAKFEQ-IEDCESKPACLLKIEYYTLNPIPGCPS LPDKTFARRT-REALNDHCPGYPETERNDGTQEMAQEVQNICLN-QTSQILRLWYSFMQSP E. This (SEQ ID NO:6) represents SEQ ID NO:5 with an amino-terminal methionine.

SEQ ID NO:10: YDFTNCDFEKIKAAYLSTISEDLI-YYMSGTKSTEFNNTVSCSNRPHCLTEILSLTFNPTAG CASLAKEKFAMRTKAALAIWCPGYSETQINATQAM-KKRRKRKVTTNKCLEQVSQLQGL WRRFSRPLLKQQ. This (SEQ ID NO:10) represents a functional variant (mutant) TSLP protein, ("TSLP 21") (see FIG. 14).

SEQ ID NO:11:
MYDFTNCDFEKIKAAYLSTISEDLIYYMSGTKSTEF-NNTVSCSNRPHCLTEILSLTFNPTA GCASLAKEKFAM-RTKAALAIWCPGYSETQINATQAMKKRRKRK-VTTNKCLEQVSQLQ GLWRRFSRPLLKQQ. This (SEQ ID NO:11) represents SEQ ID NO:10 with an amino-terminal methionine.

The TSLP protein or polypeptide for use in the inventive method and composition can be obtained from any suitable source or methodology. For example, information about suitable TSLP isoforms that can be employed in the context of the present invention is known to persons of ordinary skill in the art and is available via published nucleic acid and amino acid sequence information, see accession numbers: AF338732, NM_021367, Q969D9.1, and NP_067342, which are incorporated herein by reference. Accordingly, using only routine skill, recombinant TSLP protein or polypeptide for use in the inventive method and composition can be synthesized in bacteria or eukaryotic expression systems, purified, and then formulated as desired into pharmaceutical compositions. Alternatively, if desired, TSLP protein or polypeptide can be synthesized using solid state polypeptide synthesis technology. However, both the human and murine isoforms are commercially available (e.g., as reported in the Examples herein, from R&D Systems and also from other sources), such that de novo production of these proteins is not necessary to practice the inventive method. Additionally, Sonesson et al. (*Experimental Dermatology* 20: 1004-1010 (2011)), page 1005, incorporated herein by reference) report that TSLP-derived peptides 1-10 reported therein were supplied by Sigma Genosys (PEP screen, The Woodlands, Tex., USA), and a truncated form ("MKK34") having the following sequence: MKKRRKRKVTTNKCLEQVSQLQGLWR-RFNRPLLK (SEQ ID NO:7) was provided by another commercial source (Biopeptide (Sand Diego, Calif., USA)). Additionally, Bjerkan et al. (*Mucosal Immunology,* 8(1): 49-56 (2015), page 54, incorporated herein by reference) report that the full length recombinant TSLP was acquired from another commercial source (Peprotech (Rocky Hill, N.J.)) and two truncated derivative peptides (63aa: MFAM-KTKAALAIWCPGYSETQINATQAMKKRRKRK-VTTNKCLEQVSQLQGLWRRFNR PLLKQQ (SEQ ID NO:8) and 60aa: MKTKAALAIWCPGYSETQINATQAM-KKRRKRKVTT-NKCLEQVSQLQGLWRRFNRPLLKQQ (SEQ ID NO:9)) were obtained from ProteoGenix SAS (Schiltigheim, France). Thus, it will be apparent that a suitable TSLP protein or polypeptide for use in the inventive method can be acquired from a number of sources. Preferably, the TSLP isoform to be employed in accordance with the inventive method is derived from the same species as the patient.

Aside from a sequence represented by one of SEQ ID NOs: 1-11 above, the TSLP protein or polypeptide for use in the inventive method can have a sequence highly identical to one of the sequences disclosed herein. In this respect, the TSLP protein or polypeptide can comprise, consist of, or consist essentially of a sequence at least 75% (or at least about 75%), such as at least 80% (or at least about 80%), or at least 85% (or at least about 85%), or at least 90% (or at least about 90%), or even at least 95% (or at least about 95%), such as at least 97% (or at least about 97%) or at least 99% (or at least about 99%) identical to any one of SEQ ID NO:s 1-11). The percent identity can be calculated using the commonly employed BLAST online resource using the BlastP algorithm.

Aside from a sequence represented by one of SEQ ID NOs: 1-11 above, the TSLP protein or polypeptide for use in the inventive method can be a functional variant of one of those sequences. For example, a functional variant can comprise the amino acid sequence of the parent TSLP protein or polypeptide sequence with at least one conservative amino acid substitution. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can represent an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, a functional variant can comprise the amino acid sequence of the parent TSLP protein or polypeptide with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to parent TSLP protein or polypeptide.

However obtained or engineered, the activity of a variant of TSLP (or a TSLP protein or polypeptide) can be assessed using a neutrophil killing assay, such as is described in Example 9 herein with respect to MRSA. It will be observed that such assays can identify variant TSLP mutants that may be more or less active than wild-type TSLP.

The TSLP protein or polypeptide for use in the inventive method can consist essentially of the specified amino acid sequence or sequences described herein, such that other components of the functional variant, e.g., other amino acids, do not materially change the biological activity of the functional variant. In this regard, the TSLP protein or polypeptide can, for example, consist essentially of the amino acid sequence of any of SEQ ID NOs: 1-11. For example, a recombinant mouse TSLP protein product is marketed by R&D Systems, and is described as "Source: Mouse myeloma cell line, NS0-derived Tyr20-Glu140, with a C-terminal 10-His tag." Also, it should be apparent that the inventive method can employ more than one type or isoform of TSLP protein or polypeptide—i.e., the method can employ a plurality or combination of different types or isoforms of TSLP proteins or polypeptides.

However obtained, for use in the context of the present invention, the TSLP protein or polypeptide is formulated into a pharmaceutical composition, which, in addition to the TSLP protein or polypeptide, comprises a pharmaceutically-acceptable carrier. A composition including a TSLP protein or polypeptide can be prepared in accordance with standard techniques well known to those skilled in the pharmaceutical or veterinary arts. Such compositions can be administered in dosages and by techniques well known to those skilled in the medical or veterinary arts taking into consideration such factors as the age, sex, weight, species and condition of the particular patient, and the route of administration. The TSLP protein or polypeptide can be administered alone, or can be co-administered with other agents, or can be sequentially administered with other agent(s) or other antibiotic or vaccine compositions thereby providing cocktail or combination compositions or administrations, and methods employing them.

The TSLP protein or polypeptide can be administered by any means known to one of skill in the art (see Banga, "Therapeutic Peptides and Proteins: Formulation, Processing, and Delivery Systems, Third Edition," CRC Press, 2015) such as by intramuscluar, subcutaneous, or intravenous injection, but even oral, nasal, or anal administration is contemplated. Also contemplated is topical administration (e.g., to barrier tissues or to abscesses as discussed above). In one embodiment, administration is by subcutaneous or intramuscular injection. To extend the time during which the peptide or protein is available to stimulate a response, a peptide or protein can be provided as an implant, an oily injection, or as a particulate system. The particulate system can be a microparticle, a microcapsule, a microsphere, a nanocapsule, or similar particle. A particulate carrier based on a synthetic polymer has been shown to act as an adjuvant to enhance the immune response, in addition to providing a controlled release.

Thus, examples of compositions include preparations for orifice (e.g., anal, intragastric, nasal, peroral, vaginal, etc.) administration such as suspensions, syrups or elixirs or for ophthalmic or otic administrations, such as drops and ointments; and, preparations for parenteral, subcutaneous, intradermal, intramuscular, intraperitoneal or intravenous administration (e.g., injectable administration, including the use of needleless injectors) such as sterile suspensions or emulsions, are contemplated. Examples of compositions for topical administration include salves, ointments, creams, patches, bandages, and the like. In such compositions the TSLP protein or polypeptide can be in admixture with a suitable carrier, diluent, or excipient, such as sterile water, physiological saline, glucose or the like. The pharmaceutical compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. The compositions can also be lyophilized. Standard texts, such as "Remington: The Science and Practice of Pharmacy" (22d edition, Pharmaceutical Press, 2012), incorporated herein by reference, may be consulted to prepare suitable preparations, without undue experimentation.

In a specific embodiment, pharmaceutical compositions comprising the TSLP protein or polypeptide are administered via liposomes, microparticles, or microcapsules. In various embodiments, it may be useful to use such compositions to achieve sustained release of the TSLP protein or polypeptide.

Alternatively, an expression vector which contains a DNA sequence encoding the TSLP protein or polypeptide can be used and formulated into a pharmaceutical composition suitable for delivering the vector. Once the vector is delivered to the host cell, the cell will transcribe the DNA into the TSLP protein or polypeptide. If the host cell is that of the patient this method accomplishes production and delivery of the TSLP protein or polypeptide simultaneously. The expression vector can contain any desired genetic constructs to achieve delivery of the encoded TSLP protein or polypeptide to the patient.

The compositions disclosed herein can be administered for therapeutic or prophylactic treatments. For therapeutic applications, compositions are administered to a subject having a disorder in a therapeutically effective amount, which is an amount sufficient to cure or at least partially arrest the disease or a sign or symptom of the disorder. Amounts effective for this use will depend upon the severity of the disorder and the general state of the patient's health. An effective amount of the compound is that which provides either subjective relief of a symptom(s) or an objectively identifiable improvement as noted by the clinician or other qualified observer. Suitable dosages can also be based determined by one of skill in the art.

Single or multiple administrations of the compositions are administered depending on the dosage and frequency as required and tolerated by the subject. In one embodiment, the dosage is administered once as a bolus, but in another embodiment the dosage can be applied periodically until a therapeutic result is achieved. Generally, the dose is sufficient to treat or ameliorate symptoms or signs of disease without producing unacceptable toxicity to the subject.

As noted above, the dosage of the composition varies depending on the weight, age, sex, and method of administration. The dosage can also be adjusted by the individual physician, veterinarian, or laboratory researcher, as appropriate to the patient, as called for based on the particular circumstances. The compositions can be administered conventionally containing the active composition as a predetermined quantity of active material calculated to produce the desired therapeutic antibacterial or immunologic effect in association with the required pharmaceutically acceptable carrier or diluent (i.e., carrier or vehicle).

As a result of the inventive method, the host defense of the patient is promoted so as to more robustly combat the bacterial infection. In particular, the inventive method results in an enhancement of the capacity of the patient's neutrophils to kill the bacterial pathogen (such as MRSA).

It will be observed that the invention also pertains to the use of a TSLP protein or polypeptide for preparing a medicament (such as a pharmaceutical composition, as discussed above) for promoting the host defense of a patient to a bacterial infection, such as those bacterial infections described above. As noted, a particularly preferred embodiment involves the use of a TSLP protein or polypeptide for preparing a medicament for promoting the host defense of a patient to MRSA.

In another aspect, the invention provides a method of treating blood product, which comprises introducing a TSLP protein or polypeptide into such blood product. By "blood product" in this context is meant extracorporeal blood or a derivative of blood. Thus, the blood product can be whole blood or any derivative product of blood (e.g., plasma, packed red cells, etc.) so long as the blood product comprises at least one (and preferable a plurality of) neutrophils. The TSLP protein or polypeptide can be any TSLP protein or polypeptide, such as those disclosed above. However, preferably, the TSLP protein or polypeptide isoform to be employed in accordance with the inventive method is derived from the same species as is the blood product. As a result of introducing the TSLP protein or polypeptide into the blood product, the capacity of neutrophils within the blood product to kill bacterial pathogens, such as MRSA, is enhanced.

EXAMPLES

The following examples further illustrate the invention but, of course, should not be construed as in any way limiting its scope.

Specifically, the studies reported in the Examples below show that that mouse neutrophils express the TSLP receptor, TSLPR, and that TSLP protein is increased during cutaneous MRSA infection. Using in vitro MRSA whole blood killing assays, the data demonstrate that TSLP acts on mouse neutrophils in the blood to enhance MRSA killing. In an in vivo MRSA intradermal ear infection, TSLPR-deficient mice exhibit increased MRSA burden compared to wild-type mice. Moreover, TSLP protein or polypeptide treatment increases cutaneous MRSA killing in wild-type mice, as intradermal TSLP protein or polypeptide treatment of wild-type mice results in significantly enhanced MRSA killing in the ear. Taken together, these data show that TSLP protein or polypeptide plays a positive role in the control of cutaneous MRSA. Importantly, TSLP protein or polypeptide action relies on neutrophils in vivo, as depletion of neutrophils eliminates the effects of TSLP protein or polypeptide treatment. In addition, using TSLPR-deficient mice, the data show that the effect of TSLP protein or polypeptide on MRSA killing is TSLPR dependent. Furthermore, TSLP protein or polypeptide increases MRSA killing in human whole blood and also acts directly on purified human blood neutrophils to increase control of MRSA. These data indicate that TSLP protein or polypeptide acts on both mouse and human neutrophils to increase MRSA killing and may have implications for the treatment of cutaneous or systemic MRSA infections.

Thus, the data demonstrate that that TSLP protein or polypeptide acts on mouse neutrophils to increase their killing of MRSA in both an in vitro whole blood killing assay and an in vivo skin infection model, and that TSLP protein or polypeptide also can act directly on purified human blood neutrophils to reduce MRSA burden. Therefore, neutrophils represent previously unrecognized potent responders to TSLP protein or polypeptide. Unexpectedly, the data demonstrate that TSLP protein or polypeptide mediates these effects by directly engaging the complement C5 system to modulate reactive oxygen species production by neutrophils. Thus, TSLP protein or polypeptide increases MRSA killing in a neutrophil- and complement-dependent manner, revealing a key connection between TSLP protein or polypeptide and the innate complement system, with potentially important therapeutic implications for control of MRSA infection.

While TSLP is known for being highly expressed at barrier surfaces, such as the lung, gut, and skin, the role of TSLP in cutaneous bacterial infections has not been elucidated. Moreover, TSLP has not been previously shown to act directly on neutrophils. However, the data reported in the Examples below demonstrate that TSLP protein or polypeptide promotes host defense to infection with MRSA, including skin MRSA infection. Whereas TSLP has been shown to be involved in the progression of allergic skin diseases, such as atopic dermatitis, the data presented in these Examples demonstrate that TSLP protein or polypeptide also plays a key unexpected protective role in the skin by increasing immune control of a bacterial infection via engaging a vital arm of innate immunity. These findings uncover an unanticipated role for TSLP protein or polypeptide in neutrophil effector function and protection against a bacterial infection, with a functionally critical crosstalk between TSLP protein or polypeptide and the complement system, and therapeutic implications for MRSA skin infections.

For the experiments reported in the Examples below, the following materials, reagents, and protocols were followed:

Mice

In experiments where only WT mice were used, 6-9 week old WT BALB/c mice or C57/BL6 mice were obtained from The Jackson Laboratory. Tslpr$^{-/-}$ (Al-Shami et al., *J Exp. Med.*, 202, 829 (2005)) and C5aR1$^{-/-}$ (Jackson Laboratory) mice were bred for this study. Gp91$^{phox-/-}$ mice were purchased from the Jackson Laboratory. For experiments, using both knockout mice and WT mice, littermate control WT mice were used. 6-9 week old strain-, age- and sex-matched mice were used for experiments. All experiments were performed under protocols approved by the National Heart, Lung, and Blood Institute Animal Care and Use Committee and followed National Institutes of Health guidelines for the use of animals in intramural research.

Bacteria

The USA 300 clinical isolate (FPR3757) of MRSA was used in these studies, except where indicated. For whole blood killing assays, MRSA was plated overnight on a blood agar plate, 1 colony was picked and grown overnight at 37° C. shaking in 2 ml of Tryptic Soy Broth (TSB) (Fisher Scientific) and then washed 2 times with PBS. The non-MRSA *S. aureus* strain, MW2, and *S. pyogenes* strain, NZ131, (both from ATCC) were used in the same way as MRSA, except NZ131 was grown in Todd Hewitt Broth under static culture conditions. For intradermal (i.d.) ear infections, bacteria in logarithmic growth were used.

Whole Blood Killing Assays

Whole blood killing assays were adapted from Kaplan et al. (Kaplan et al., *J. Immunol.*, 189, 4537 (2012)) In brief, whole mouse blood was collected into 4% sodium citrate, and whole human blood from healthy donors was collected into sodium citrate tubes. 75 µl of whole blood, 5 µl of 4% sodium citrate, 10 µl of PBS or mouse or human TSLP (100 ng/ml final concentration; both from R&D Systems) and 25 µl of MRSA (at a 1:1800 dilution of OD600=0.25) were sequentially added to capped 2 ml skirted tubes and the tubes were slowly rotated in a 37° C. incubator for 3 h. Serial 10-fold dilutions were then made, and the blood was spread on blood agar plates and incubated overnight. Colonies were counted the following day to determine the colony forming units (CFU)/tube. Experiments were performed with triplicate samples.

Mouse Neutrophil Isolation

For elicitating peritoneal neutrophils, mice were injected i.p. with 1 ml of 3% thioglycollate and 4 h later their peritoneums were lavaged with 10 ml cold PBS and cells were collected. For bone marrow neutrophils, femurs from mice were excised under sterile conditions and the cells were flushed out using 2% FBS in PBS+1 mM EDTA. Both peritoneal and bone marrow neutrophils were purified using either a Miltenyi Biotech negative selection Neutrophil Isolation Kit, or by a 55%/65%/75% percoll gradient.

Human Neutrophil Isolation and In Vitro MRSA Killing Assays

Whole blood from healthy donors was collected in EDTA tubes, and neutrophils were isolated directly from the blood by negative selection using a kit (Stem Cell). For neutrophil killing assays, 3-4×10$^5$ neutrophils (either purified human blood neutrophils or thioglycollate-elicited mouse peritoneal neutrophils) were added to a capped 2 ml skirted tube in RPMI medium. PBS or TSLP (100 ng/ml final), and/or PMX-53 (5 pM; Tocris Bioscience) were added and incubated for 5 min. 50 µl of coated MRSA or *S. pyogenes* (bacteria at a 1:50 dilution of OD600=0.25) pre-incubated in 10% autologous human or mouse serum) was added/tube, for a final total volume of 200 µl. In some experiments, neutrophils were primed with HKSA (Invivogen) plus either PBS or TSLP for 2 h before addition of MRSA. The tubes were slowly rotated in a 37° C. incubator for 2-3 h as indicated in the figure legends. For DPI treatment, neutrophils were incubated with 2 µM DPI for 30 min, washed, counted, and then used in the killing assay as described above. For MAPK/ERK and PI3K inhibition, human neutrophils were pre-incubated for 20 min with 50 µM PD98059 or 20 µM Ly294002, respectively, and then either PBS or TSLP and MRSA were added for 2 h shaking. After the 2 hr incubation the samples were put on ice, 10-fold serial dilutions were made, spread on blood agar plates, incubated overnight at 37° C., and colonies counted to determine the CFU/tube. Each treatment was done in triplicate. Whole blood from healthy human NIH blood bank volunteer donors was obtained without donor identification and met the criteria for exemption from informed consent and institutional review board review as defined in The Code of Federal Regulations Title 45 (Public Welfare), Department of Health and Human Services, Part 46 (Protection of Human Subjects), and their distribution was in accord with National Institutes of Health guidelines for the research of human subjects.

Neutrophil Depletion

Neutrophil-depleted blood was obtained by injecting mice i.p. with 0.5 mg of anti-Ly6G antibody (1A8, Bioxcel) two days before blood was collected. For infection studies of neutrophil-depleted mice, mice were injected i.p. with 0.5 mg of anti-Ly6G antibody two days before and again on the day of infection. Neutrophil depletion was ~93-98% efficient as assessed by flow cytometric staining with Gr-1 and Ly6C antibodies (Biolegend).

Intradermal Ear Infection 6-9 week old WT, Tslpr$^{-/-}$, or C5ar1$^{-/-}$ BALB/c mice or neutrophil-depleted WT BALB/c mice were injected intradermally (i.d.) using a 29½-gauge ³⁄₁₀ ml insulin syringe (BD Biosciences) with MRSA or S. pyogenes mixed with either TSLP (2 µg) or PBS (final OD600=0.125 in a total volume of 10 µl). In some experiments, 10 µg of anti-mouse C5 blocking antibody (BB5.1, Hycult Biotech) or mouse IgG1 isotype control (MOPC-21, Bioxcel) was additionally added, but the total volume injected was still 10 µl. For in vivo ROS inhibition, 1.3 µg of NAC (N-acetyl-L-cysteine, Sigma-Aldrich) was co-injected with PBS or TSLP and MRSA i.d. into the ears. Each experiment included 6-12 ears per group. Some samples were excluded at the time of infection due to a poor injection.

Neutrophil In Vivo Transfer Experiments

Equal numbers of purified WT and Tslpr$^{-/-}$ bone marrow neutrophils were either co-transferred (~3×10$^6$ of each) into WT mice or labeled with 5 µM CMDFA, as previously described (Swamydas et al., JoVE, e50586 (2013)), and transferred separately (~15×10$^6$) into Tslpr$^{-/-}$ mice i.v. 30 min prior to infection with MRSA i.d. in the ear.

Preparation of Ear Cells

On day 1 or 2 post-infection, the ears were processed as described (Ribeiro-Gomes et al., Infect. Immun., 82, 2713 (2014)). In brief, ears were excised, washed with 70% ethanol, and allowed to dry for 5 min. The dorsal and ventral layers were separated and incubated at 37° C. for 90 min in RPMI medium containing Liberase, homogenized for 3.5 min in a Medimachine, flushed out of the Medicon, filtered, using a 50 µM strainer and centrifuged. The homogenate was then serially diluted 10-fold, plated on blood agar plates, and plates incubated at 37° C. for 18 h. Colonies were counted the following day to determine MRSA titers. The remaining ear homogenate was used for flow cytometric analysis using the indicated antibodies.

Antibodies for Flow Cytometric Analysis

For mouse samples: anti-CD11b (M1/70), Gr-1, Ly6G (1A8), Ly6C (HK1.4), F4/80, CD127, and C5aR1 (20/70) antibodies and TruStain fcX were from Biolegend, and anti-TSLPR (FAB5461F) was from R&D Systems. The appropriate isotype controls from the corresponding company were used for all phenotyping antibodies. For intracellular staining, cells were fixed and permeabilized with Cytofix Cytoperm and Perm wash (BD Biosciences). For human samples: anti-CD16 (3G8), CD66b (G10F5), CD11b (M1/70) and Trustain were from BioLegend. Anti-TSLPR (1F11) was from BD biosciences and the cells were fixed and permeabilized before staining with TSLPR. Samples were collected using a FACS Canto II or Fortessa flow cytometer (BD Biosciences) and analyzed using Flow Jo analysis software (Treestar, Inc).

Ex-Vivo Detection of ROS

Mouse ear samples were processed as described above, and cells were incubated in medium with 5 µM of Cell Rox® Deep Red reagent (Life Technologies) for 30 min at 37° C., washed 3 times with PBS, and fixed with 4% paraformaldehyde before staining for CD11b$^+$ Ly6G$^+$ (Ly6C$^{low}$).

Phagocytosis Assay

Mouse bone marrow neutrophils or human blood neutrophils were isolated as described above, stimulated with PBS or TSLP, and incubated with pHrodo® Green S. aureus Bioparticles® (Life Technologies) for 5, 20, or 30 min, per the figure legends, and phagocytosis assessed by flow cytometry on a FACS Canto II. For inhibition of phagocytosis, neutrophils were pretreated with either DMSO or cytochalasin D (10 µg/ml) for 15 min.

CRLF2 RT-PCR

Human neutrophils were isolated and stimulated with medium or 10$^9$ HKSA/ml (Heat killed S. aureus, InvivoGen) for 4 h. Probes for CRLF2 (Hs00845692_m1) and RPL7 (Hs02596927_g1) were from Life technologies.

RNA Sequencing

Neutrophils were purified from 2 independent human donors on different days (in 2 independent experiments) and stimulated with either PBS or TSLP, with or without heat killed MRSA for 4 and 24 hr. The cells were washed, RNA purified, RNA-Seq libraries prepared using the KAPA Stranded mRNA-Seq kit (Kapa Biosystems), and sequencing performed using an Illumina HiSeq 2000 platform in the NHLBI DNA Sequencing core.

TSLP Protein Measurement

Mouse ears were excised, washed with 70% ethanol, allowed to dry for 5 min, and then the dorsal and ventral layers were separated, put into 1 ml of PBS with protease inhibitor, homogenized using a Minibead beater (Biospec), cleared by centrifugation, and samples were immediately frozen. TSLP protein was determined using the BioLegend Legendplex kit according to the manufacturer's protocol. Similar results were found with the mouse quantikine ELISA kit (R & D Systems).

Ear Pathology

Ears were excised, fixed with 3.7% formalin, and embedded in paraffin. Three segments of each ear were cut and the slides were stained with hematoxylin and eosin. Pathological scoring of the H&E stained sections was performed blinded.

Statistics

Statistical significance was calculated as indicated in the figure legends, using GraphPad Prism 6 software. For all statistical analyses, data were considered significant when P≤0.05 (*), P≤0.01 (), P≤0.001 (*) or P≤0.0001 (****). Variances were similar between groups in all experiments, as determined by the F test using GraphPad Prism 6 software. The animal experiments were not randomized. The investigators were not blinded to allocation during experiments and analyses unless otherwise indicated.

Example 1

This Example demonstrates that TSLP enhances MRSA killing in a whole blood assay.

Incubating TSLP together with MRSA in mouse blood significantly increased bacterial killing at both 2 and 3 hours, as compared to that observed with the addition of PBS and MRSA (assayed by colony forming units, CFU) (FIGS. 8, A and B, and FIG. 1, A). The possibility that the increased killing of MRSA by TSLP resulted from a direct action of TSLP on the bacteria was excluded (FIG. 8C), and it was thus sought to define the cell type that mediated TSLP-induced killing of the bacteria. Neutrophils are critical for host-defense against S. aureus, and it was found that mouse bone marrow neutrophils not only express the TSLP binding protein (receptor), TSLPR, but that TSLPR expression was further increased upon in vitro stimulation with heat-killed S. aureus (HKSA) in these cells (FIG. 1B). These data suggested that mouse neutrophils might exhibit enhanced responsiveness to TSLP during MRSA infection. To determine if neutrophils were required for the action of TSLP, mice were depleted of neutrophils by using anti-Ly6G (FIG. 1C). When neutrophil-depleted blood was used in the whole blood killing assay, TSLP no longer augmented MRSA killing (FIG. 1D), demonstrating that the increased killing of MRSA induced by TSLP was neutrophil-dependent. Importantly, neutrophils are potent killers of bacteria and while depletion of neutrophils in the blood resulted in reduced control of bacteria in general, in line with the important role neutrophils play in bacterial clearance, it did not result in complete loss of bacterial control (FIG. 8D), consistent with the contributions of other cell types, such as macrophages, to MRSA clearance. Taken together, these data demonstrate that TSLP-enhanced killing of MRSA is neutrophil-dependent.

Example 2

Figure 2A:
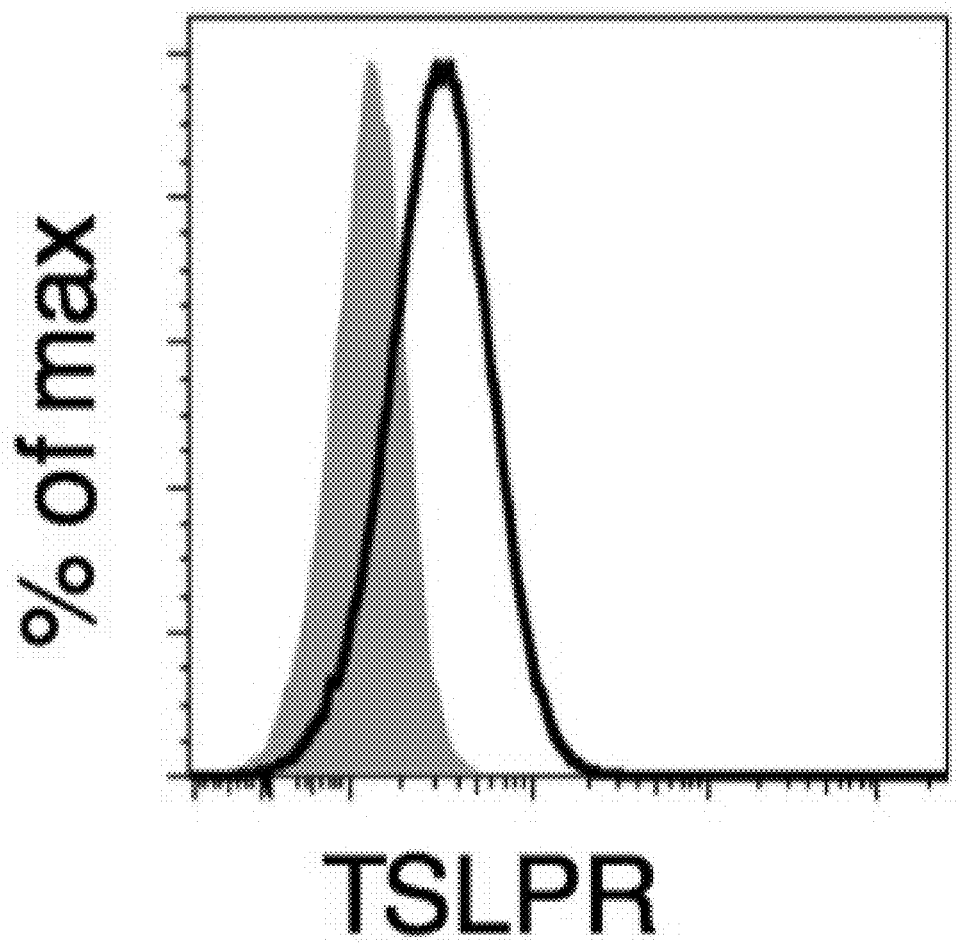
Figure 2D:
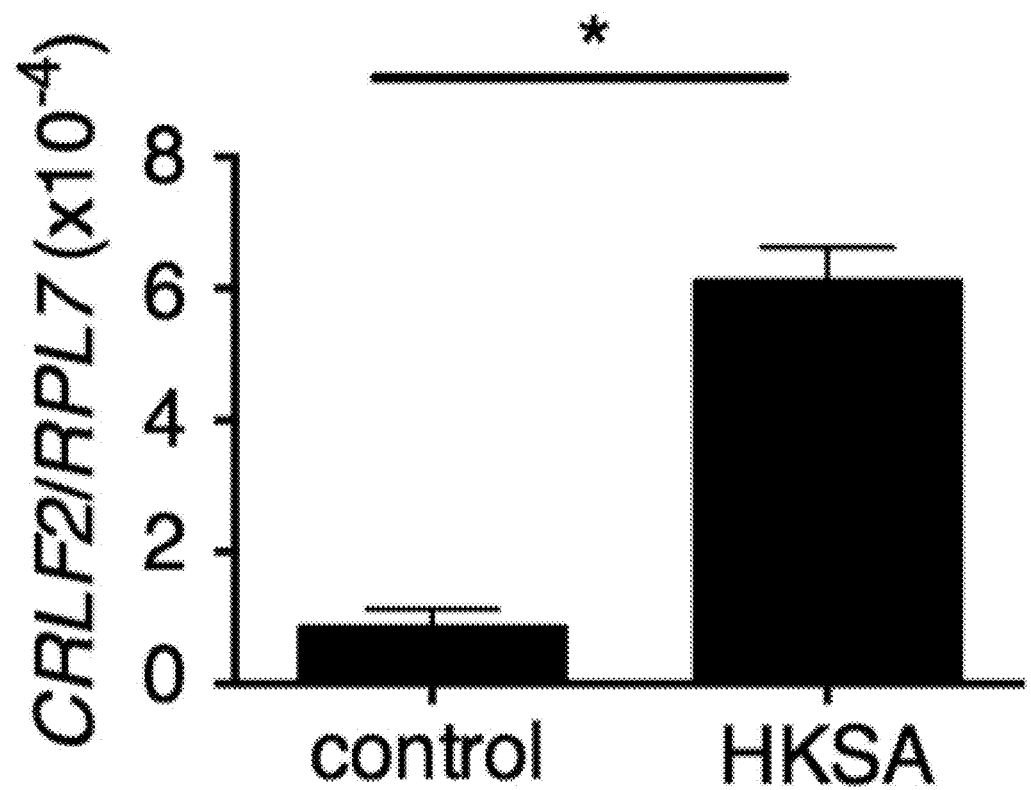
Figure 2E:
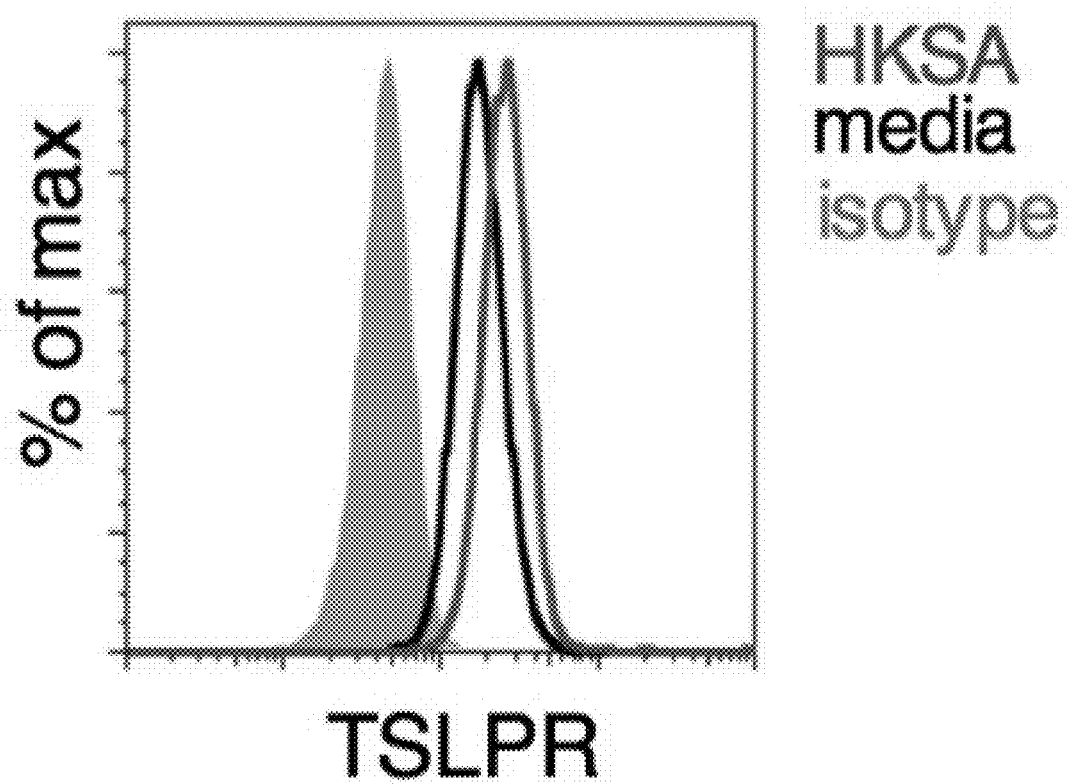

This Example demonstrates that TSLP acts directly on both mouse and human neutrophils to increase killing of MRSA To determine whether TSLP could act directly on neutrophils, purified thioglycollate-elicited mouse peritoneal neutrophils were obtained, as less mature bone marrow neutrophils are incapable of killing MRSA in vitro (FIG. 9A), and first demonstrated that they expressed TSLPR (FIG. 2A). Moreover, when these neutrophils were incubated with MRSA and TSLP for 2 h, they exhibited increased killing as compared to cells incubated with MRSA and PBS (FIG. 2B), demonstrating that TSLP can act directly on mouse neutrophils in vitro to enhance MRSA killing. This direct effect of TSLP on neutrophils was TSLPR-dependent, as TSLP did not increase the killing of MRSA by $Tslpr^{-/-}$ neutrophils (FIG. 9B).

Figure 9E:
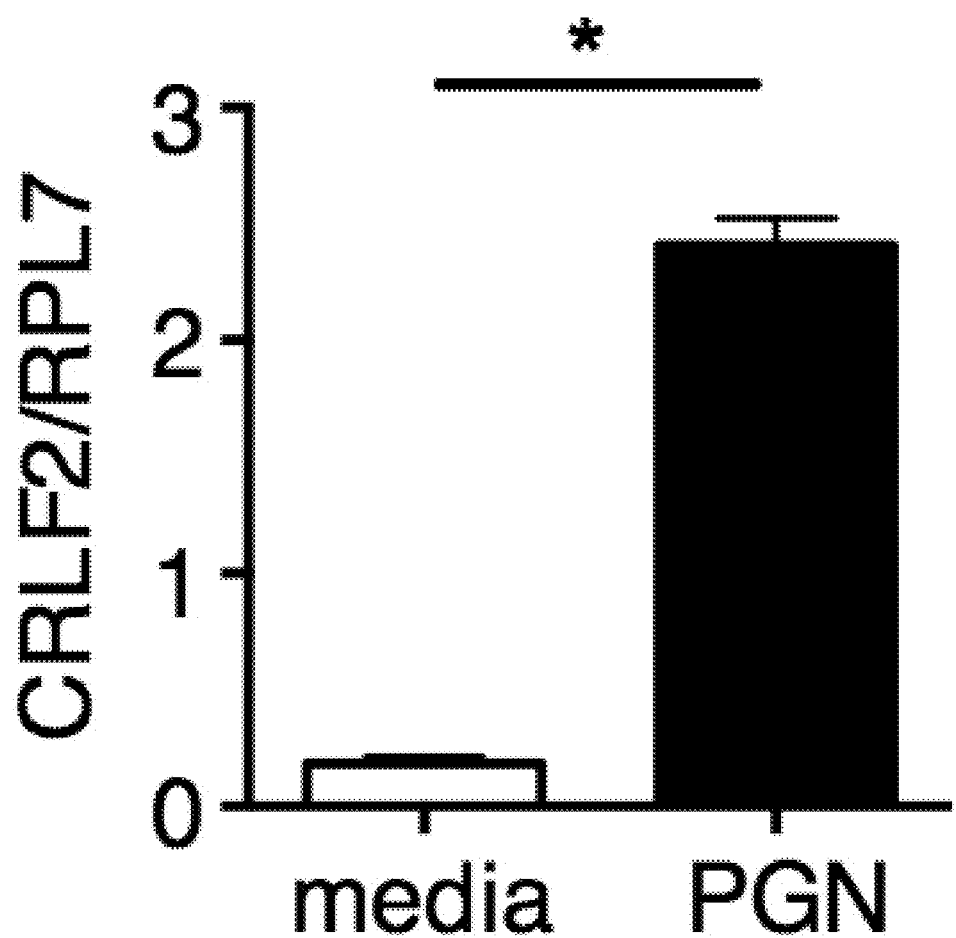
Figure 9F:
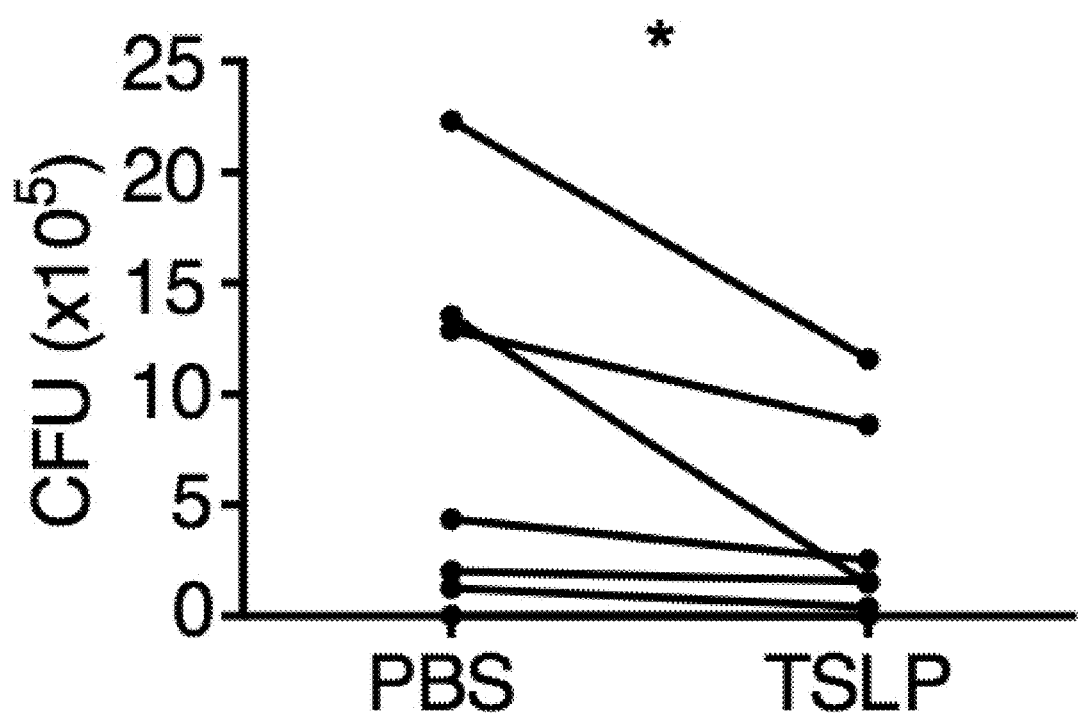
Figure 9G:
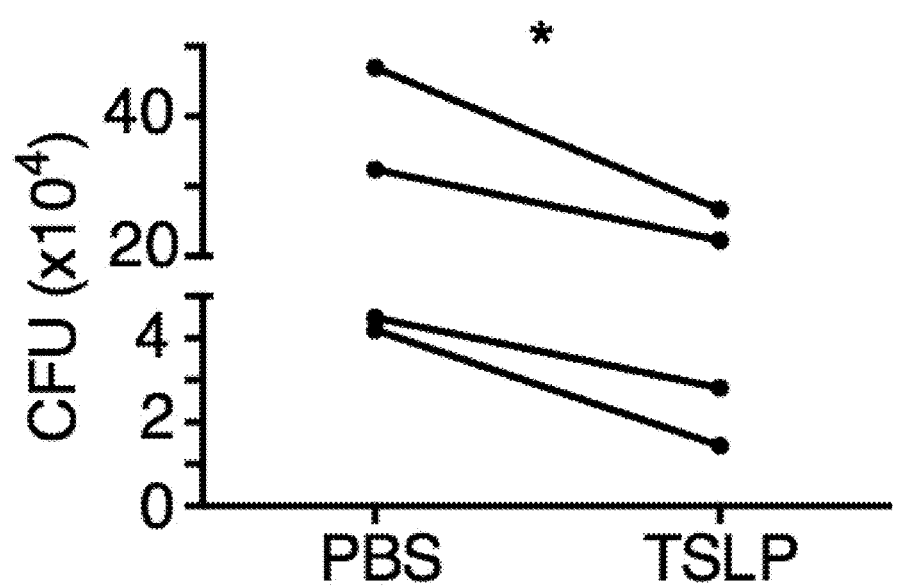

Next, whether TSLP exerts similar effects on human neutrophils was investigated. TSLP treatment resulted in increased killing of MRSA in a whole blood killing assay (a representative donor is shown in FIG. 2C, with all donors shown in FIG. 9C). Although two previous studies reported that a synthetic short form of human TSLP could have direct antimicrobial activities on some pathogens, they observed little or no killing with S. aureus (Bjerkan et al., Mucosal Immunol., 8, 49 (2015); Sonesson et al., Exp. Dermatol., 20, 1004 (2011)). Consistent with this, it was found that the increased killing of MRSA by TSLP did not result from a direct action of TSLP on the bacteria, as MRSA and TSLP incubated together with serum alone (i.e., in the absence of cells) resulted in a similar bacterial titer to that observed when control PBS was used in place of TSLP (FIG. 9D). To determine whether TSLP-induced killing of MRSA in human whole blood was mediated by neutrophils, analogous to what was found for the mouse, neutrophils from whole blood from healthy donors were purified. These human neutrophils expressed mRNA for CRLF2 (encoding TSLPR), and its expression was significantly enhanced by stimulation with heat killed S. aureus (HKSA), ranging from 5-76 fold enhancement depending on the donor (one donor shown in FIG. 2D). This increase in CRLF2 expression by HKSA was likely due to TLR2 activation, as it was found that stimulation of neutrophils with peptidoglycan, a TLR2 agonist present on gram positive bacteria including S. aureus, also increased CRLF2 expression (FIG. 9E). Consistent with these mRNA expression data, the purified human neutrophils also expressed TSLPR protein, with higher expression upon HKSA stimulation (FIG. 2E), indicating that human neutrophils might also be able to respond to TSLP. Indeed, when freshly isolated human neutrophils were incubated with PBS or TSLP and MRSA for 3 h, TSLP markedly lowered the CFU (a representative donor is shown in FIG. 2F and all donors tested are depicted in FIG. 9F). Freshly isolated human neutrophils were primed with HKSA and either PBS or TSLP, and it was found that TSLP increased the ability of primed neutrophils to kill MRSA in vitro (FIG. 9G), analogous to unprimed neutrophils. Consistent with the experiments in mice, these data demonstrate that TSLP acts directly on both unprimed and primed human neutrophils to increase their killing of MRSA.

Example 3

This Example demonstrates that Tslpr-deficient mice have increased MRSA titers during an in vivo skin infection.

Figure 3A:
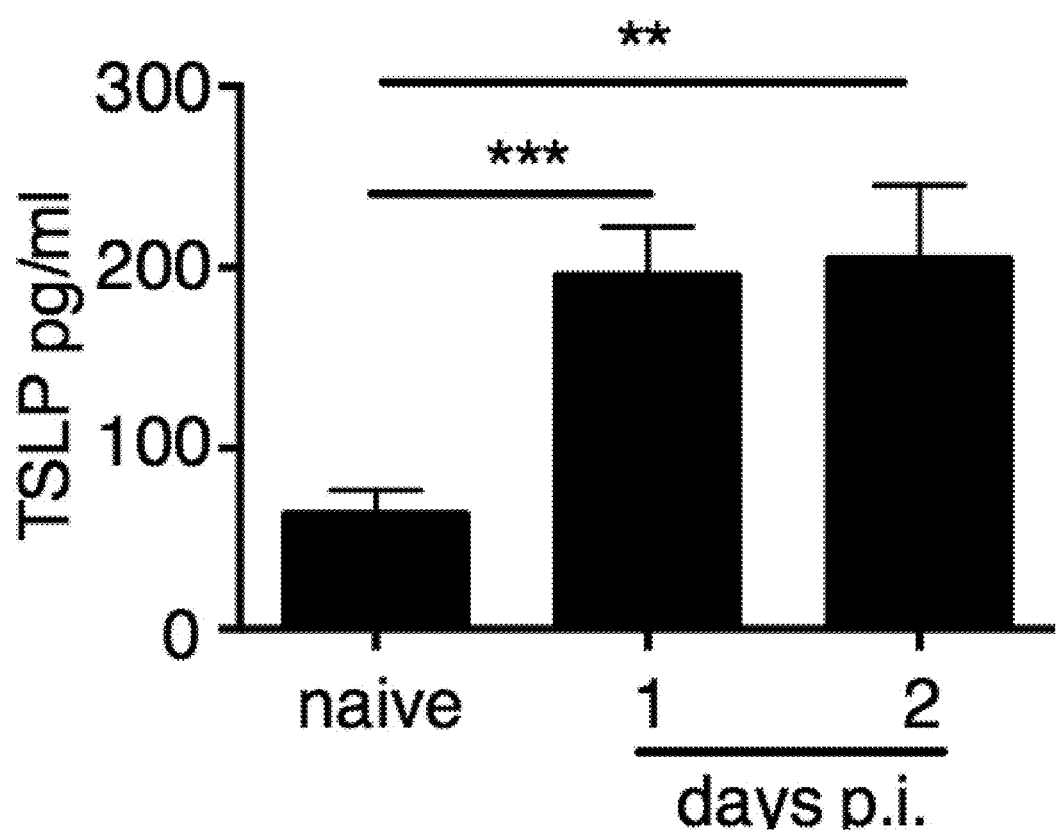
Figure 3B:
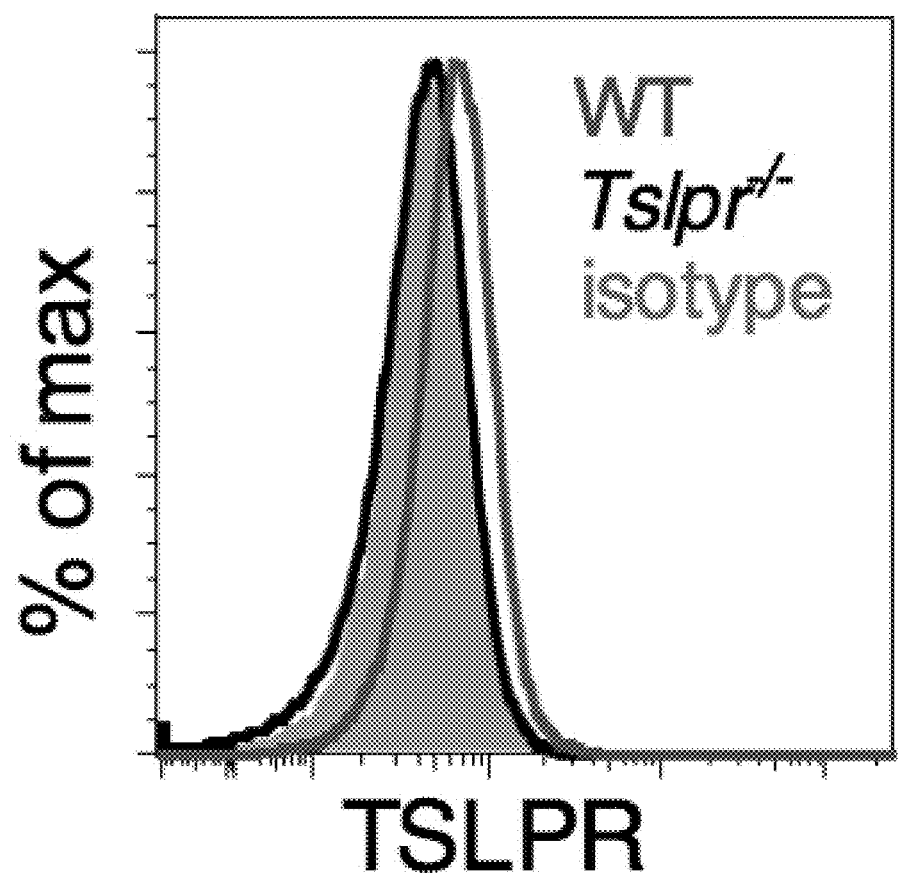
Figure 3C:
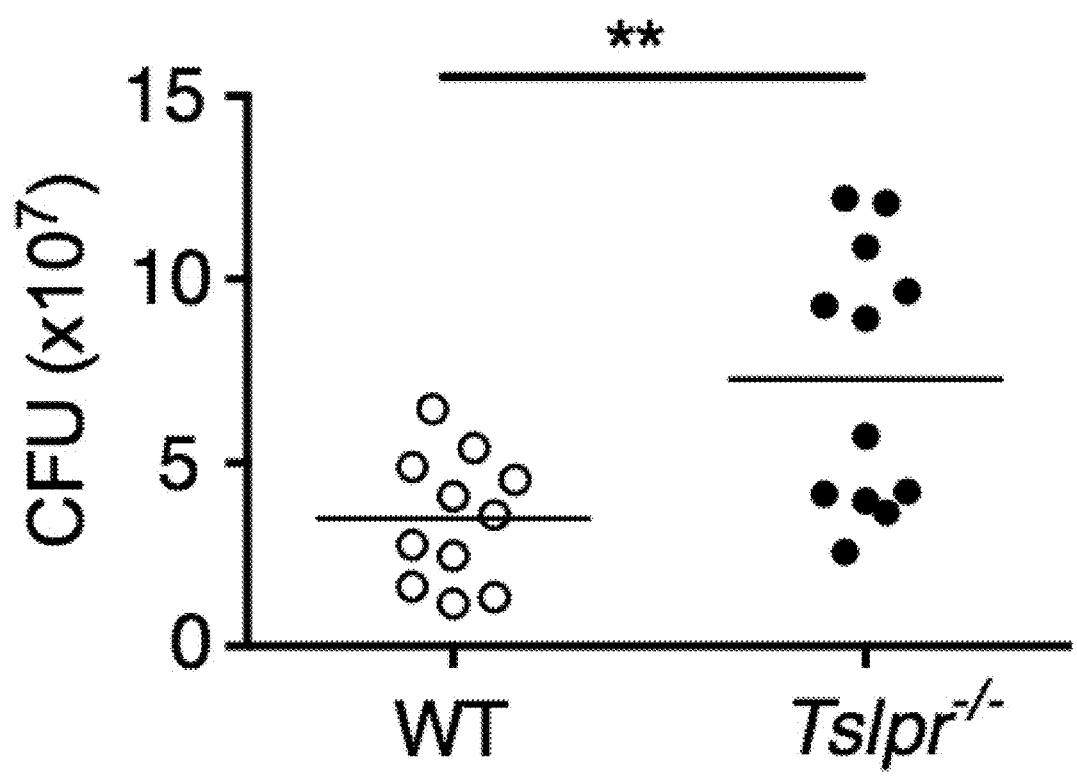
Figure 3D:
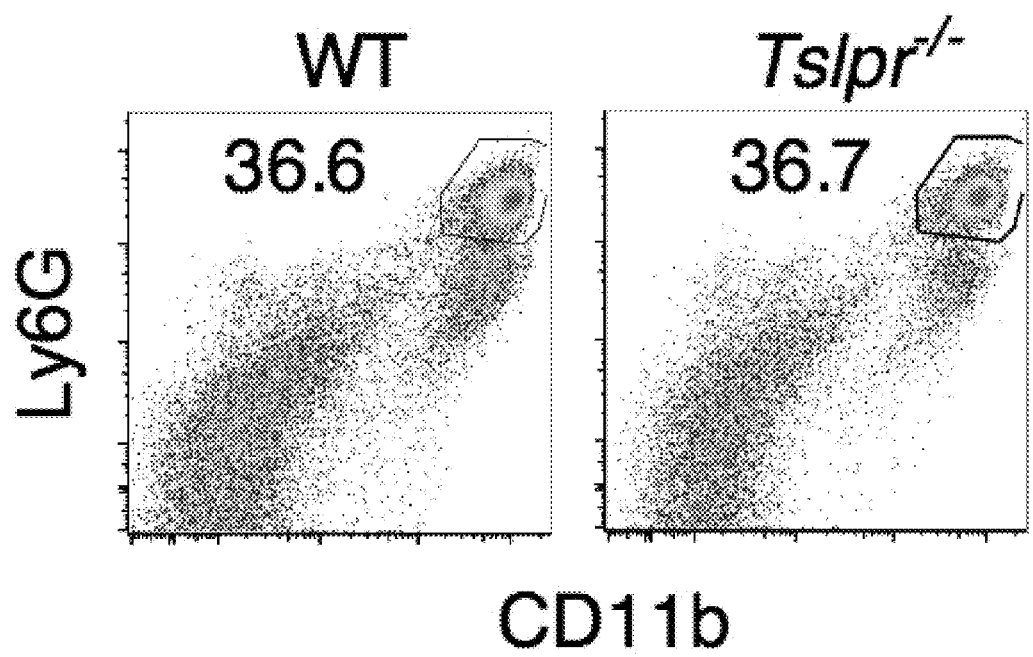
Figure 3F:
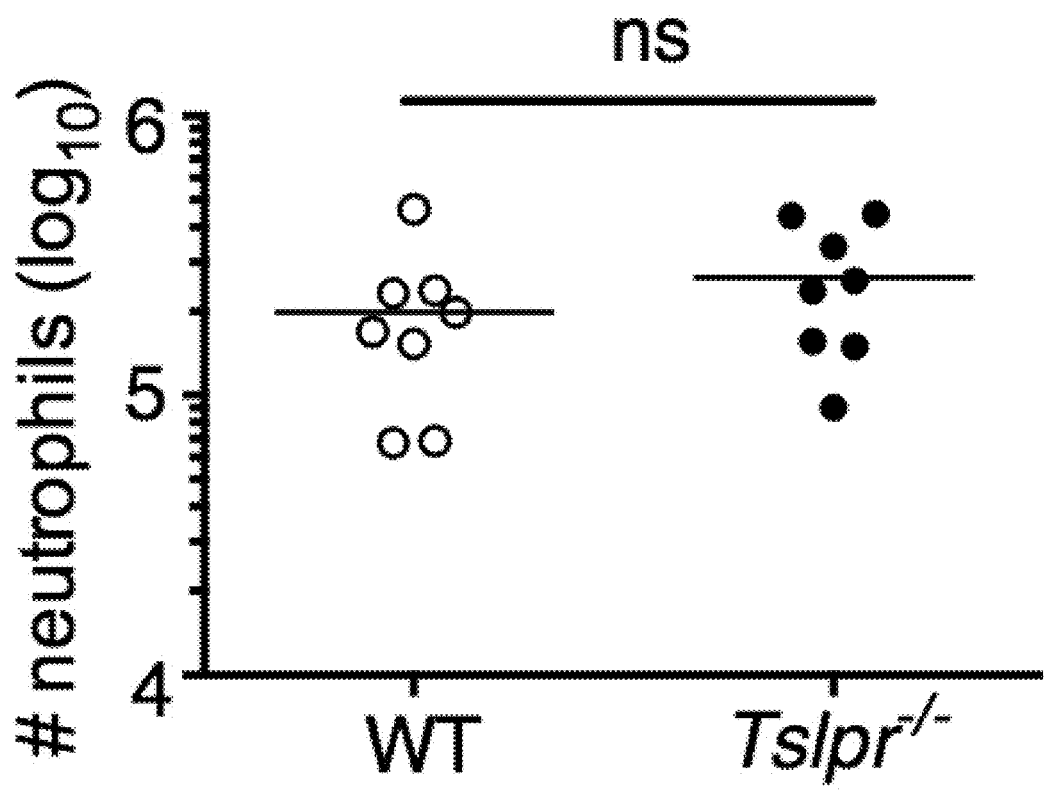
Figure 4B:
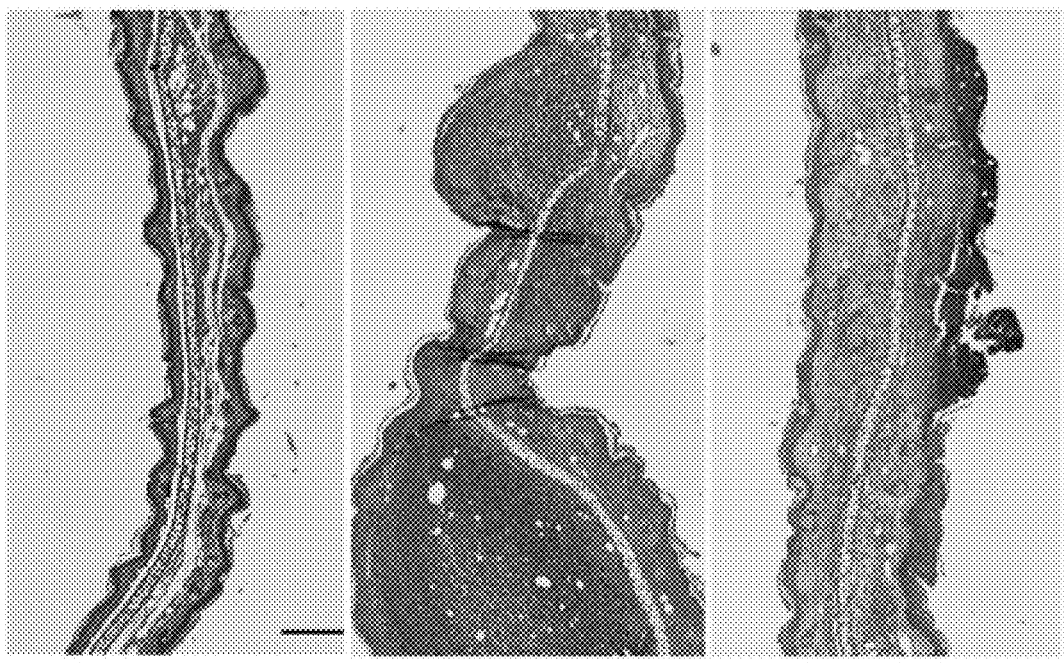
Figure 4E:
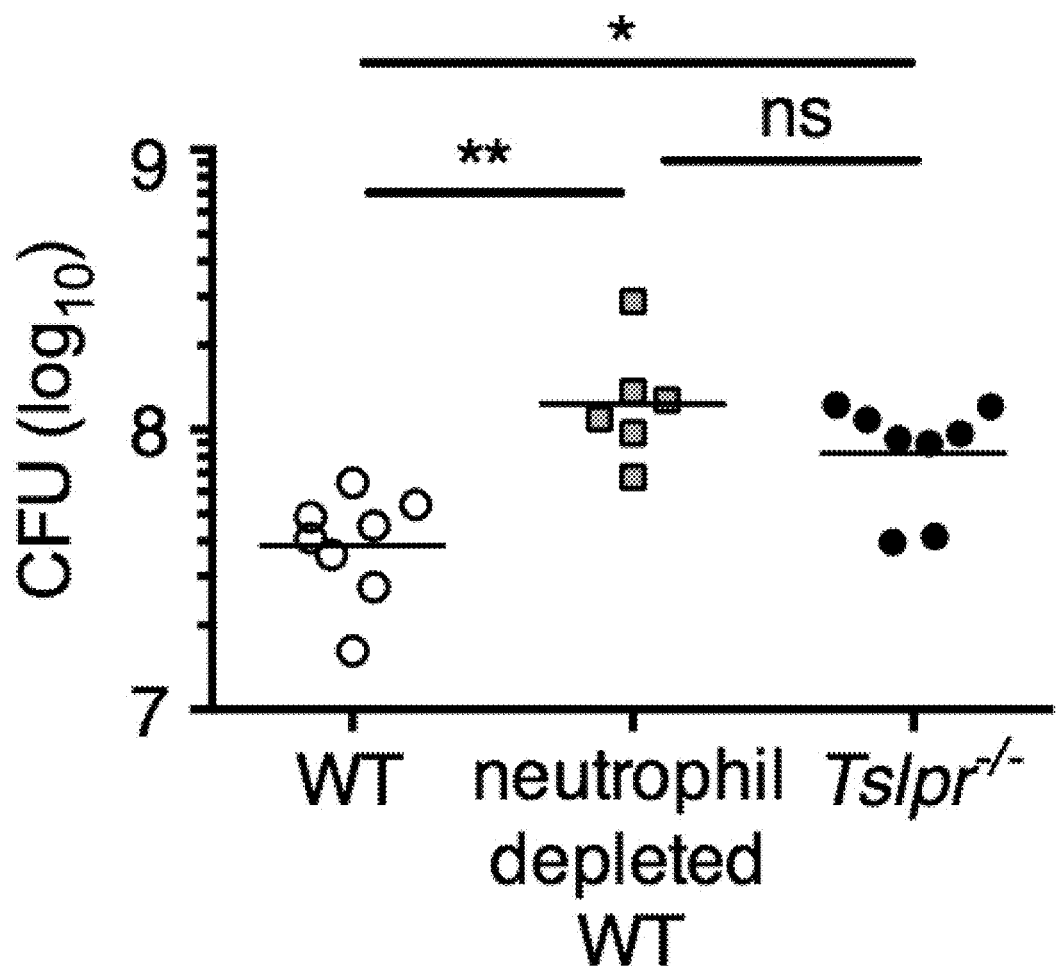

Whether the TSLP-neutrophil axis also enhanced MRSA killing in vivo was investigated by using a skin infection model in which MRSA was injected intradermally (i.d.) into the mouse ear. Interestingly, TSLP protein was potently increased in the ears at days 1 and 2 post-infection (p.i.) with MRSA, as compared to naïve PBS-injected controls (FIG. 3A). Additionally, TSLPR was expressed by ear neutrophils (FIG. 3B). To elucidate the role of TSLP in skin MRSA infection, mice were infected with MRSA i.d., which resulted in Tslpr-deficient ($Tslpr^{-/-}$) mice having a significantly higher bacterial burden than did wild-type (WT) mice (FIG. 3C), indicating that TSLP helps to control MRSA in vivo. The increased bacterial burden in $Tslpr^{-/-}$ mice was not due to reduced recruitment of neutrophils to the ear, as $Tslpr^{-/-}$ and WT mice had similar percentages (FIGS. 3, D and E) and numbers (FIG. 3F) of neutrophils in their infected ears.

To eliminate the possibility that the in vivo results resulted from compensatory mechanisms in $Tslpr^{-/-}$ mice, WT mice were treated with either a human IgG1 Fc isotype control or TSLPR-Fc fusion protein i.d. at the time of MRSA infection. It was found that the mice with in vivo TSLP blockade (TSLPR-Fc treated) had significantly increased MRSA titers in the ear compared to isotype control treated mice, confirming that TSLP enhances bacterial control during in vivo MRSA skin infection (FIG. 3G).

Example 4

This Example demonstrates that TSLP treatment enhances MRSA killing in vivo in normal wild-type ("WT") hosts.

It was sought to determine whether increased TSLP signaling could augment MRSA killing in the skin of normal hosts, and therefore PBS or TSLP plus MRSA i.d. was injected into the ears of WT mice. TSLP treatment significantly reduced the bacterial burden in the ears at day 2 p.i. (FIG. 4A), and this effect was sustained as one injection of TSLP at the time of infection resulted in significantly reduced titers even at days 3 and 6 p.i. (FIG. 10A). Because bacterial titers can only be assessed at one time-point per mouse, whether TSLP has a more cumulative effect by assessing pathology also was evaluated in these mice, and it was found that TSLP also decreased pathological changes, with significantly decreased inflammation in the skin after MRSA infection compared to that observed in PBS-treated animals (FIGS. 4, B and C). Moreover, the effect of TSLP was mediated by its functional receptor rather than an off-target effect, as Tslpr$^{-/-}$ mice treated with TSLP had similar MRSA titers to those treated with PBS (FIG. 10B).

To determine whether TSLP's ability to increase in vivo killing of bacteria was limited to MRSA, whether TSLP could also enhance the killing of both a non-MRSA strain of S. aureus (MW2) and Streptococcus pyogenes, another bacterial strain that causes clinically significant human skin infections, was tested. Indeed, WT mice treated with TSLP had significantly lower S. aureus MW2 and S. pyogenes titers compared to PBS-treated control mice (FIGS. 10C and 4D). Thus, treatment with TSLP not only can decrease MRSA burden in vivo but also can kill a non-MRSA strain of S. aureus and another pathogenic bacterial strain (S. pyogenes) in the skin as well.

Additionally, Tslpr$^{-/-}$ infected mice had a similar bacterial burden to that observed in neutrophil-depleted WT mice (FIG. 4E), suggesting that TSLP-enhanced MRSA killing in vivo might be dependent upon neutrophils. Importantly, in contrast to its ability to enhance MRSA control in mice treated with an isotype control antibody, TSLP treatment did not increase MRSA control in neutrophil-depleted (anti-Ly6G treated) WT mice, thus demonstrating that TSLP-enhanced MRSA killing in vivo was dependent on neutrophils (FIG. 4F).

Example 5

This Example demonstrates that TSLP acts directly on neutrophils in vivo to decrease MRSA burden.

Figure 5A:
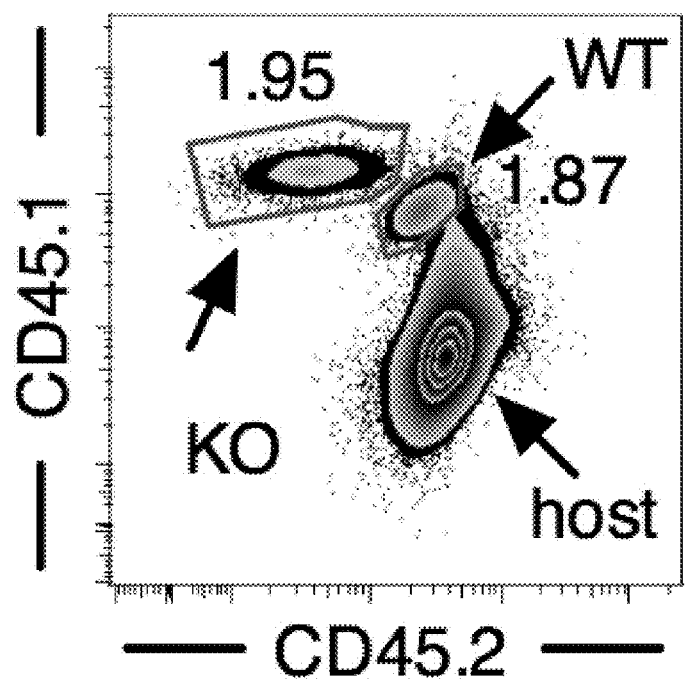

A neutrophil-specific Cre is not available, and LysM-Cre affects onocytes/macrophages as well as neutrophils. Thus, a cell transfer approach was employed in which equal numbers of purified WT and Tslpr$^{-/-}$ bone marrow neutrophils were co-transferred into naïve mice, which could be distinguished by their expression of different isoforms of the congenic marker CD45. After infection i.d. with MRSA in the ear, transferred Tslpr$^{-/-}$ neutrophils were recruited to the infection site and accumulated there equally well as WT neutrophils (FIG. 5A).

Figure 5B:
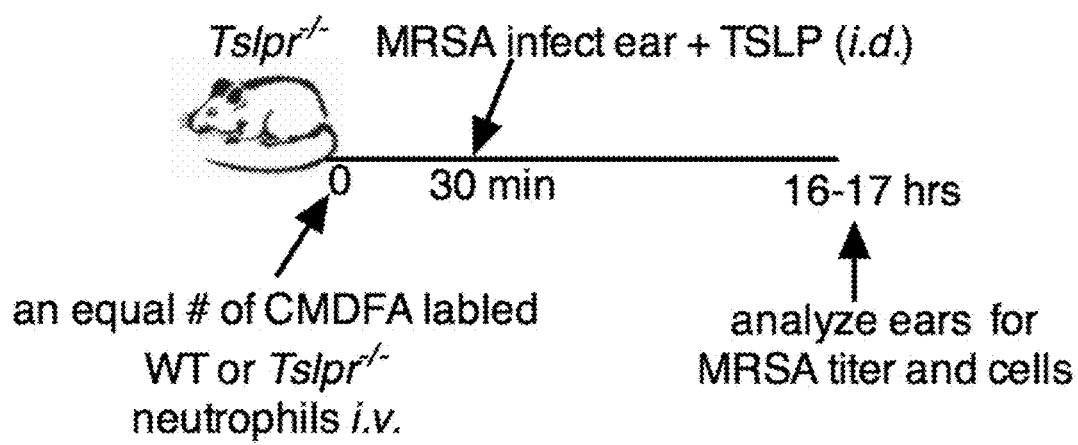
Figure 5D:
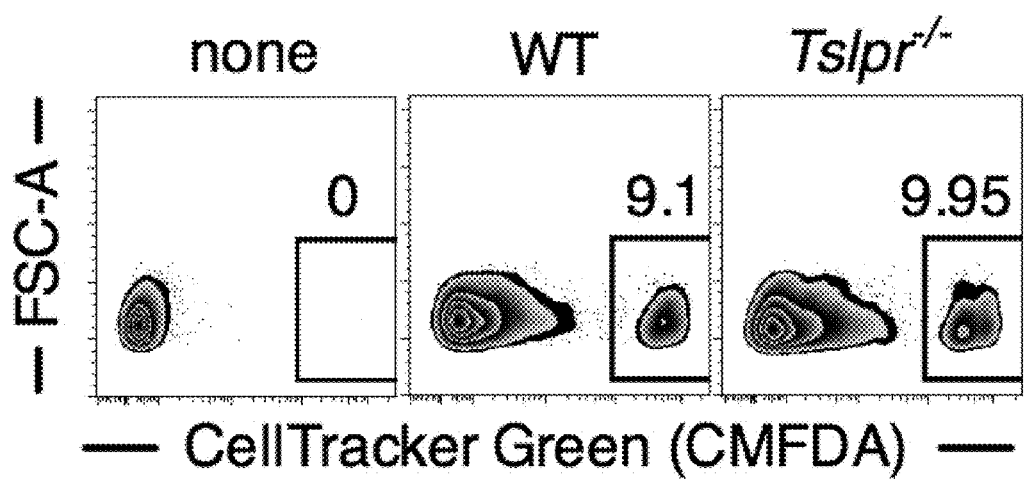
Figure 5F:
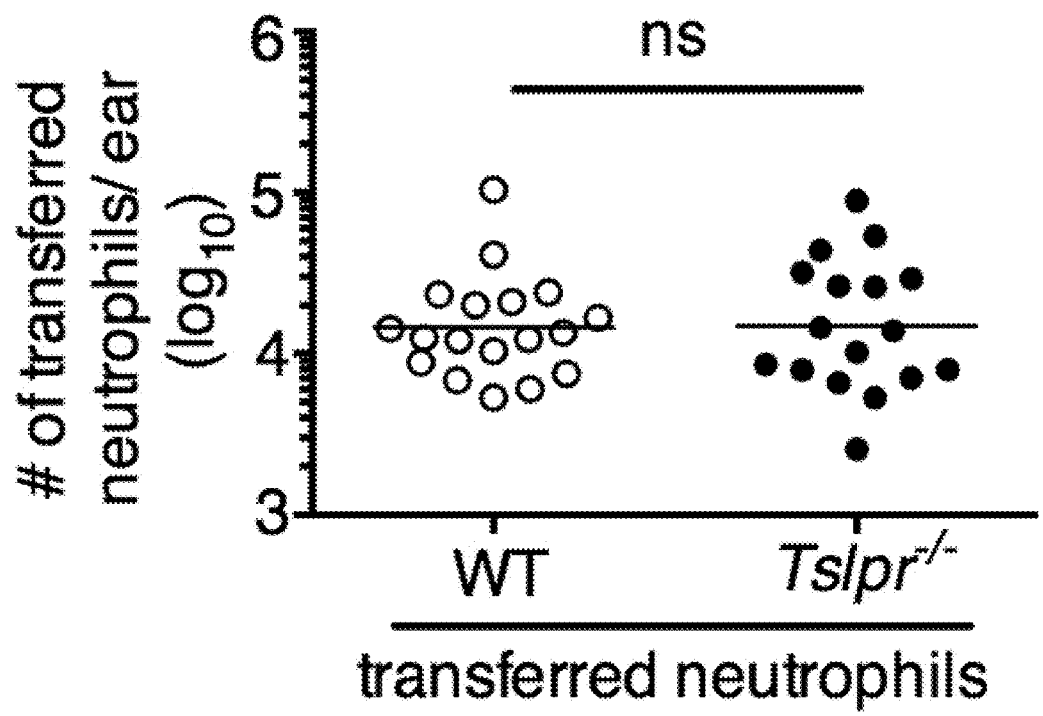

An equal number of CMDFA-labeled WT or Tslpr$^{-/-}$ purified bone marrow neutrophils next were adoptively transferred into Tslpr$^{-/-}$ mice, and then these mice were injected with MRSA and TSLP i.d. in the ear, as outlined in FIG. 5B. In these experiments, only the transferred WT neutrophils can respond to TSLP. On day 1 p.i., the Tslpr$^{-/-}$ mice that received WT neutrophils exhibited significantly greater MRSA killing (i.e., lower CFU) than mice receiving Tslpr$^{-/-}$ neutrophils (FIG. 5C). Importantly, this difference in MRSA titer was not due to less efficient recruitment of Tslpr$^{-/-}$ neutrophils than of WT neutrophils, as the percent of transferred Tslpr$^{-/-}$ neutrophils was even slightly higher than for WT neutrophils (FIGS. 5, D and E), and the overall numbers of Tslpr$^{-/-}$ and WT transferred neutrophils in the ear were similar (FIG. 5F). Given that TSLP does not directly act on MRSA (FIGS. 8C and 9C) and requires TSLPR signals to act both in vitro (FIG. 9B) and in vivo (FIG. 10B), these data together demonstrate that TLSP acts directly on neutrophils in vivo to enhance MRSA clearance.

Example 6

This Example demonstrates a non-transcriptional mechanism for TSLP-mediated MRSA killing by neutrophils.

The mechanism underlying TSLP-mediated killing of MRSA was elucidated. RNA sequencing (RNA-Seq) on purified human neutrophils treated with PBS or TSLP with or without HKSA for 4 and 24 h was performed. It was discovered that TSLP did not significantly alter the transcriptional profile of human neutrophils at either 4 or 24 h, whereas HKSA greatly increased the number of differential expressed genes (1394 genes common to both donors at 4 h and 1252 at 24 h). As compared to HKSA alone, the addition of TSLP plus HKSA resulted in the common induction in both donors of only a single gene (CCL22) at 24 h (Table 1).

TABLE 1

| | | Donor1 | Donor2 | Common |
|---|---|---|---|---|
| 4 hr | CTL vs. TSLP | 0 | 8 | 0 |
| | CTL vs. HKM | 2664 | 1631 | 1394 |
| | HKM vs. HKM + TSLP | 1 | 2 | 0 |
| 24 hr | CTL vs. TSLP | 1 | 7 | 0 |
| | CTL vs. HKM | 1832 | 1702 | 1252 |
| | HKM vs. HKM + TSLP | 1 | 6 | 1* |

*CCL22
RNA-Seq performed on neutrophils after 4 or 24 h incubation with PBS (control) or TSLP with or without HKSA. Shown are the number of differentially expressed genes (Fold Change > 1.5, FDR < 0.05, RPKM > 4) from two different donors performed in two independent experiments and the number of common genes that were differentially expressed in both donors.

Figure 11D:
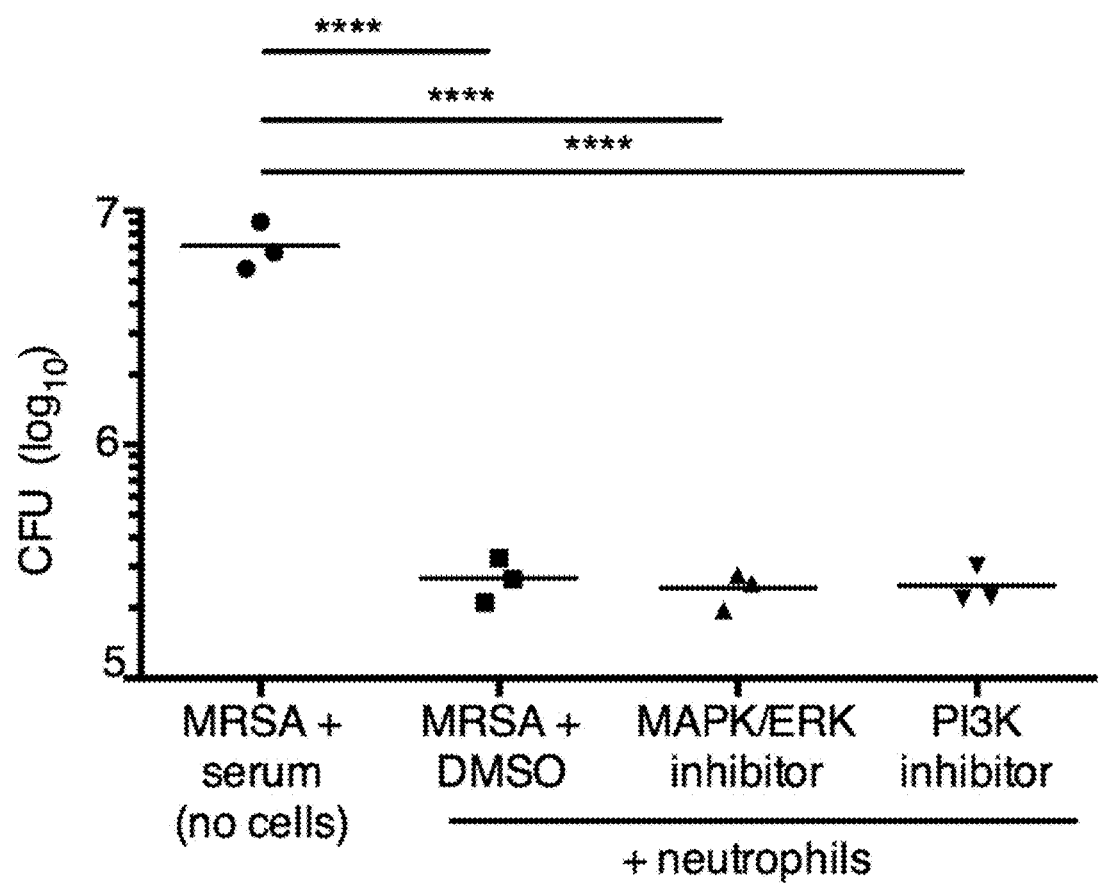

These data suggest that TSLP-mediated neutrophil killing of MRSA is not due to transcriptional activation of new gene expression during the time of the killing assays and that proximal signaling events instead might be involved. Indeed, studies using inhibitors of mitogen-activated protein kinase/extracellular signal regulated kinase (MAPK/ERK) kinase or phosphatidyl inositol 3-kinase (PI3K) showed that both of these pathways are necessary for TSLP-mediated killing of MRSA by human neutrophils, as pre-treatment with these inhibitors blocked TSLP-increased MRSA killing (FIGS. 11, A and B for MAP/ERK inhibition and FIGS. 11, A and C for PI3K inhibition) but did not eliminate the basal ability of human neutrophils to kill MRSA (FIG. 11D). Given the rapid TSLP-induced neutrophil-mediated killing of MRSA (2-3 h for the in vitro assay) and the fact that the MAPK/ERK and PI3K pathways can mediate non-transcriptional effects in neutrophils, these results indicate that TSLP-mediated MRSA killing by neutrophils is a rapid response that does not require de novo gene induction.

Example 7

This Example demonstrates that TSLP-enhanced killing of MRSA in both mouse and human is ROS-dependent.

Figure 12A:
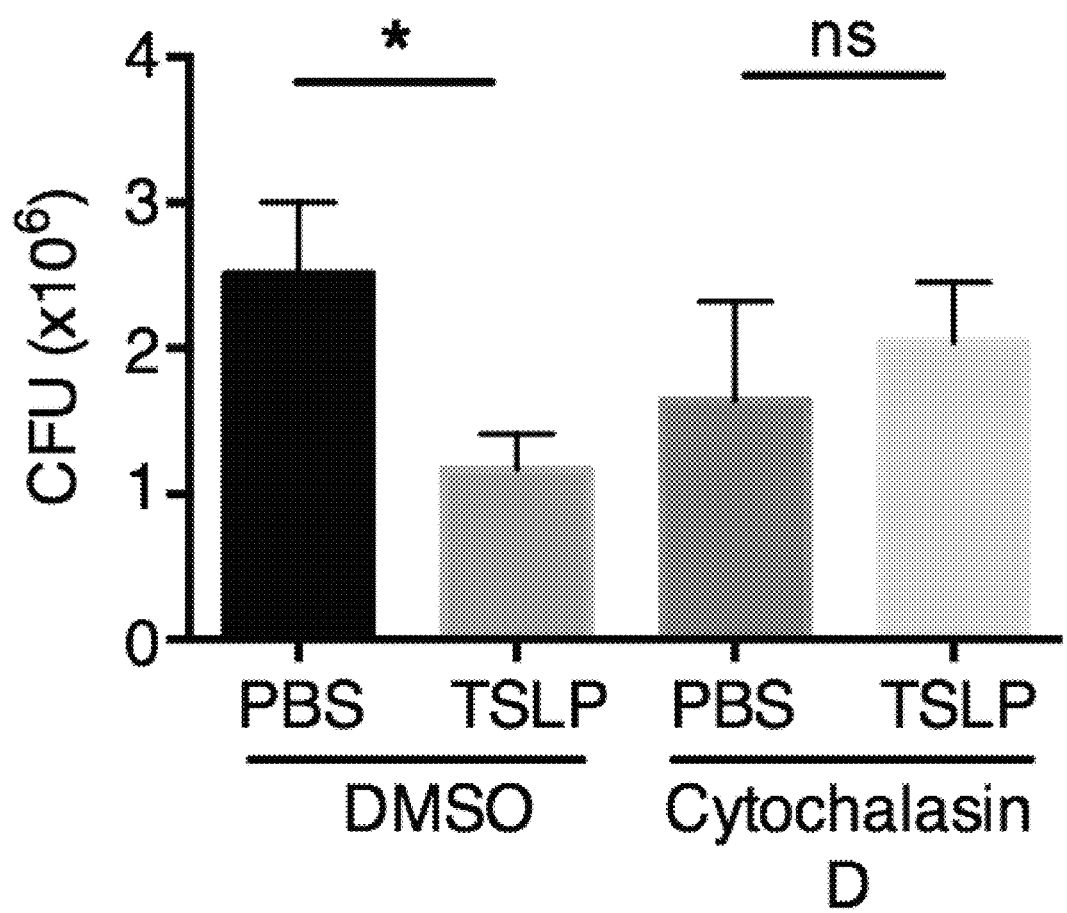
Figure 12B:
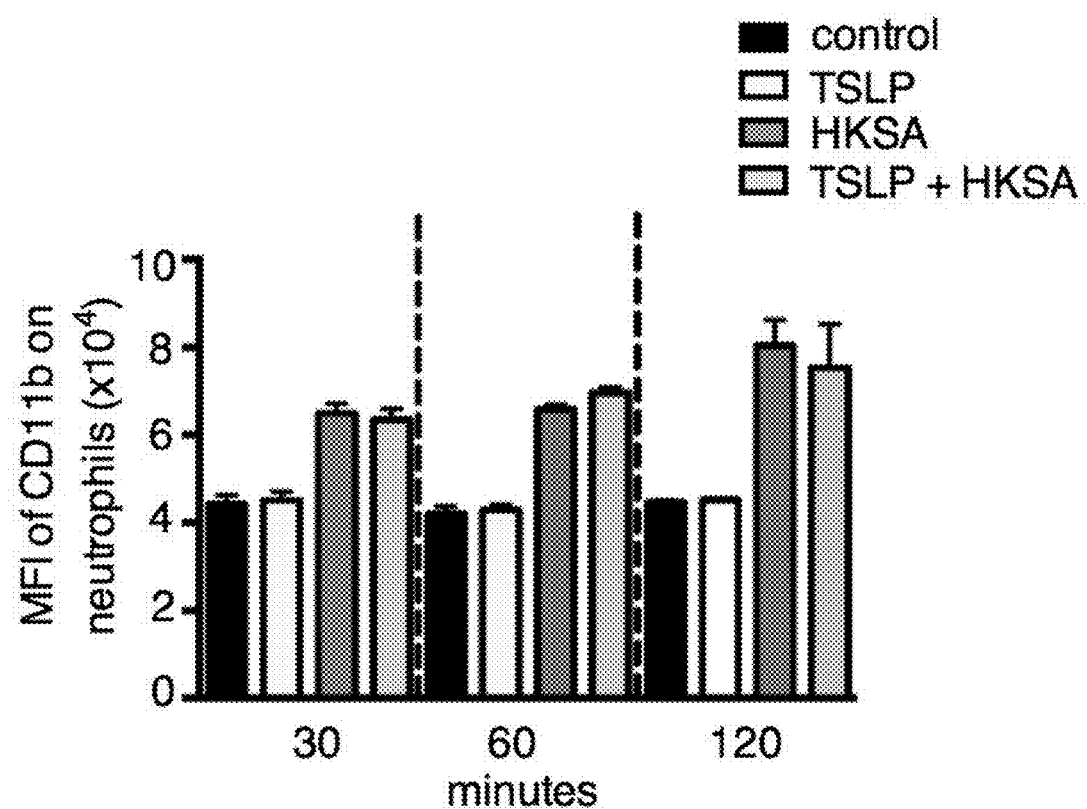
Figure 12C:
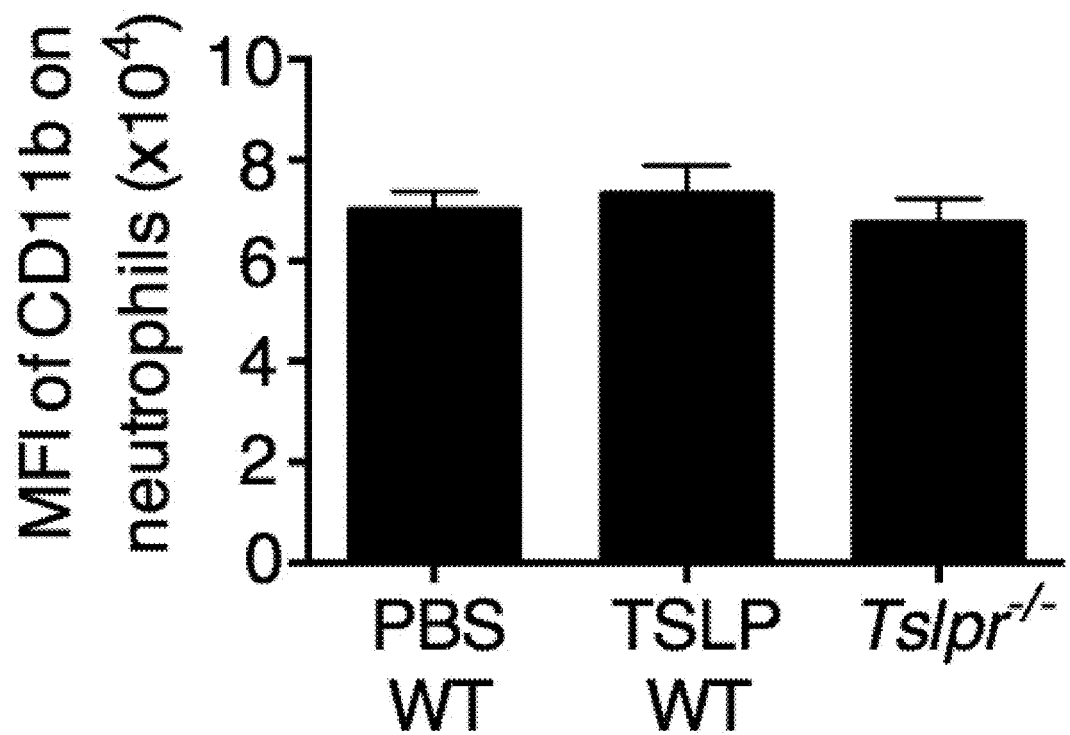
Figure 12D:
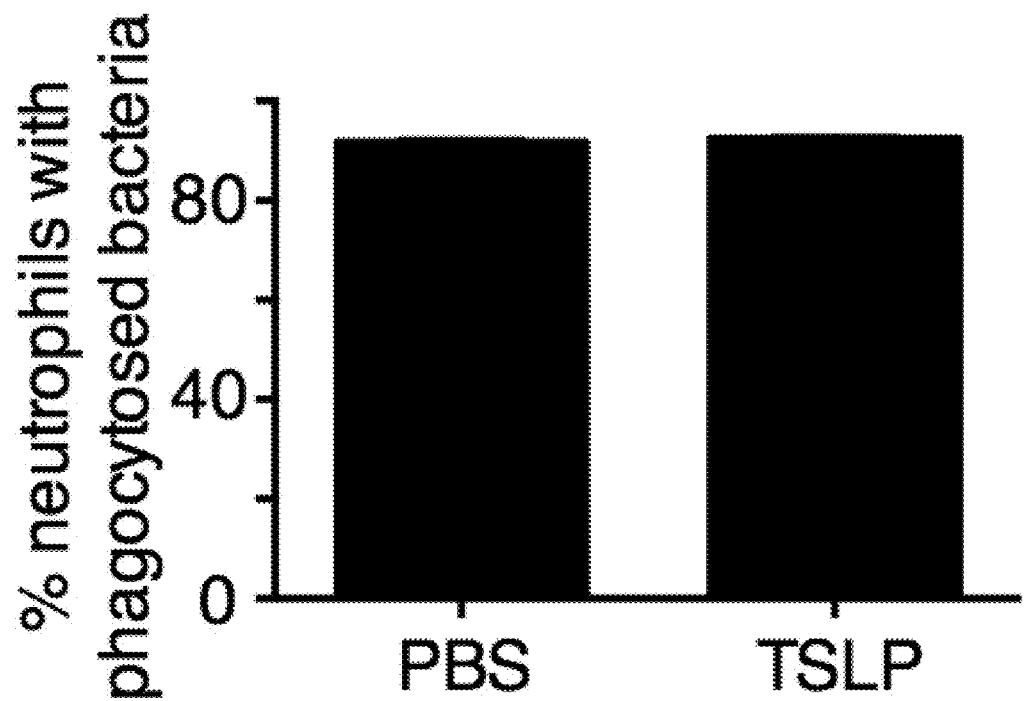
Figure 12E:
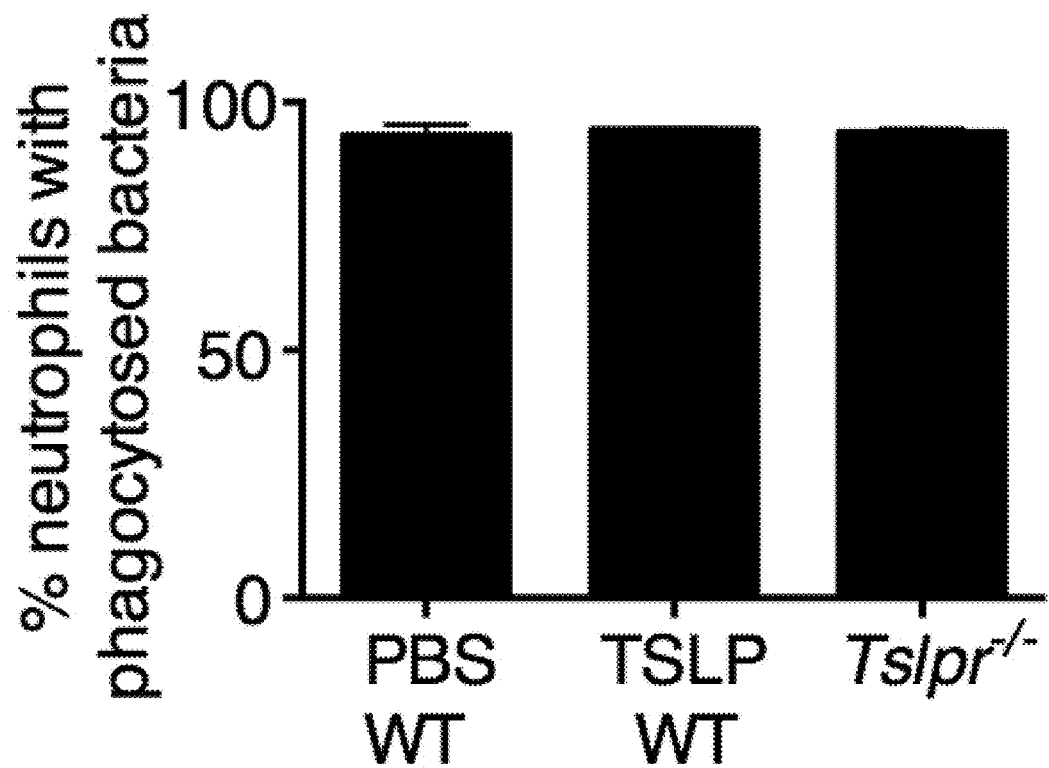
Figure 12F:
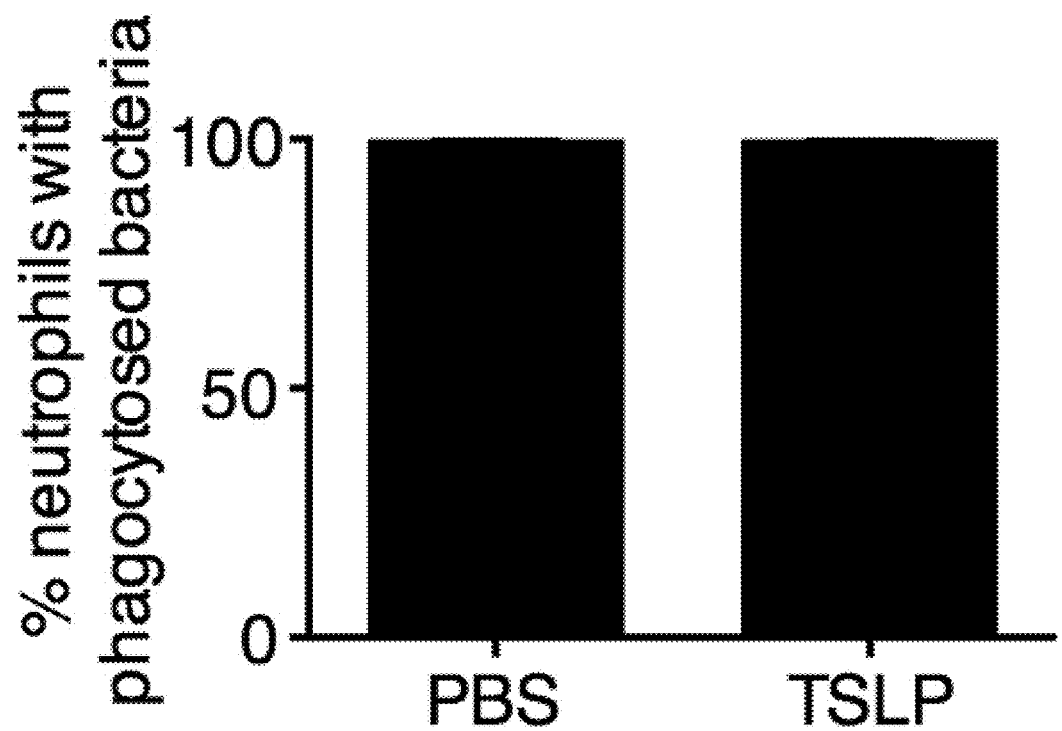

As phagocytosis of microbes is an important rapid response of neutrophils, whether TSLP might increase neutrophil phagocytosis was investigated. Pathogen uptake is likely necessary for TSLP-enhanced killing of MRSA as treatment of neutrophils with cytochalasin D, an inhibitor of phagocytosis, eliminated TSLP-enhanced killing of MRSA in vitro (FIG. 12A). Surprisingly, however, TSLP treatment did not affect expression of CD11b (a component of the phagocytic CR3 receptor) on human neutrophils in vitro (FIG. 12B) or on mouse neutrophils in vivo (FIG. 12C). Moreover, TSLP did not augment the phagocytic uptake of S. aureus by either human (FIG. 12D) or mouse (FIGS. 12, E and F) neutrophils.

A major mechanism used by human and mouse neutrophils to eliminate bacteria is the production of reactive oxygen species (ROS); therefore, the role of ROS in TSLP-driven MRSA killing in vivo utilizing the mouse skin infection model was investigated. Strikingly, neutrophils from infected Tslpr$^{-/-}$ mice had lower ROS levels (FIGS. 6, A and B) compared to neutrophils from infected WT mice, indicating that ROS might contribute to TSLP-enhanced neutrophil killing of MRSA. Consistent with this notion, TSLP treatment did not enhance MRSA killing when a ROS scavenger, N-acetyl-L-cysteine, (NAC) was administered i.d. (FIG. 6C), demonstrating that ROS is essential for TSLP-induced neutrophil-mediated killing of MRSA in vivo. To eliminate the possibility that these data resulted from non-specific actions of NAC, used Gp91$^{phox-/-}$ (Nos2$^{-/-}$) mice, which are deficient in an integral component of the NADPH oxidase complex that generates ROS. TSLP treatment did not increase the killing of MRSA in Gp91$^{phox-/-}$ mice infected i.d. in vivo with MRSA, unlike its effect in WT controls (FIG. 6D), demonstrating that ROS is essential for TSLP-induced neutrophil-mediated killing of MRSA in vivo. Consistent with an essential role for ROS in TSLP-enhanced MRSA killing in the mouse skin infection model, pre-treatment of purified human neutrophils with Diphenyliodonium (DPI), an NADPH-oxidase inhibitor, eliminated the ability of TSLP to enhance their killing of MRSA (FIG. 6E), demonstrating that ROS is also essential for TSLP-augmented control of MRSA by human neutrophils.

Example 8

This Example demonstrates that TSLP-enhanced killing of MRSA is complement-dependent.

Figure 13A:
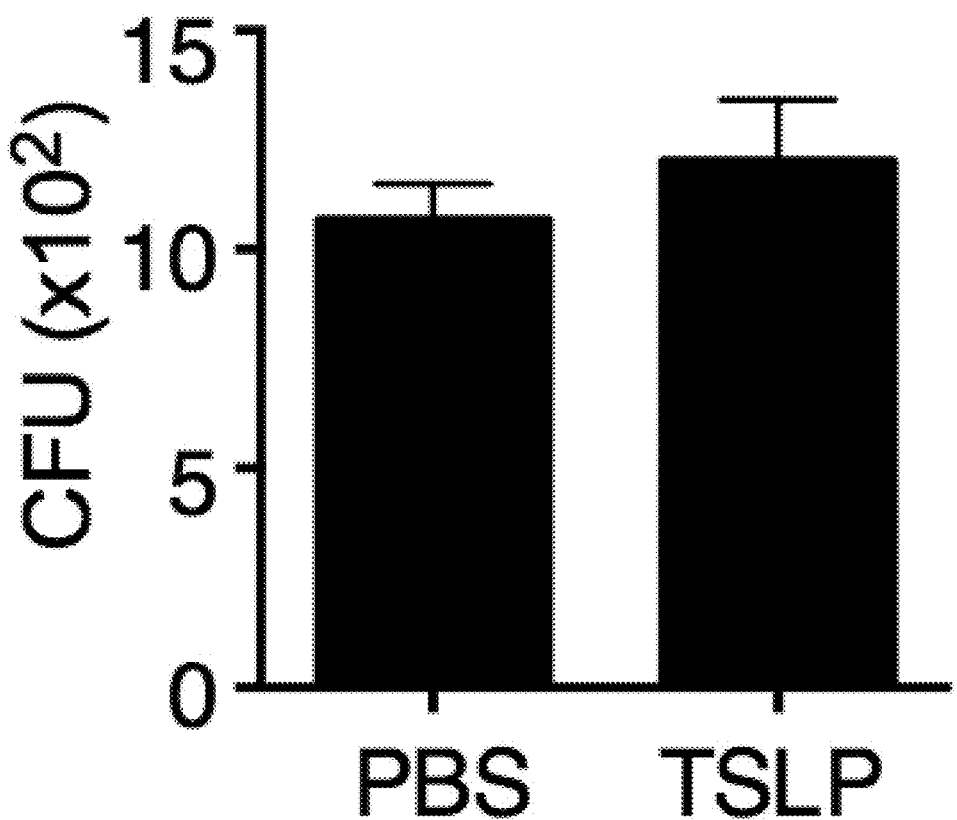
Figure 13B:
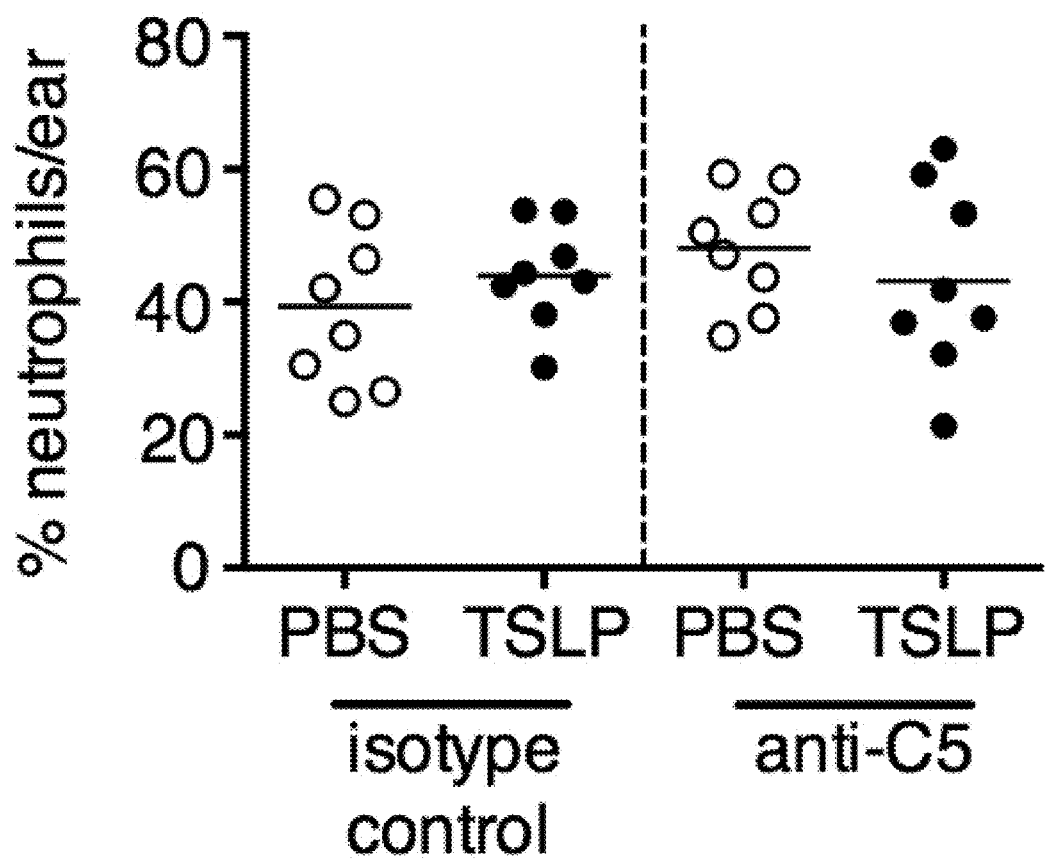
Figure 13C:
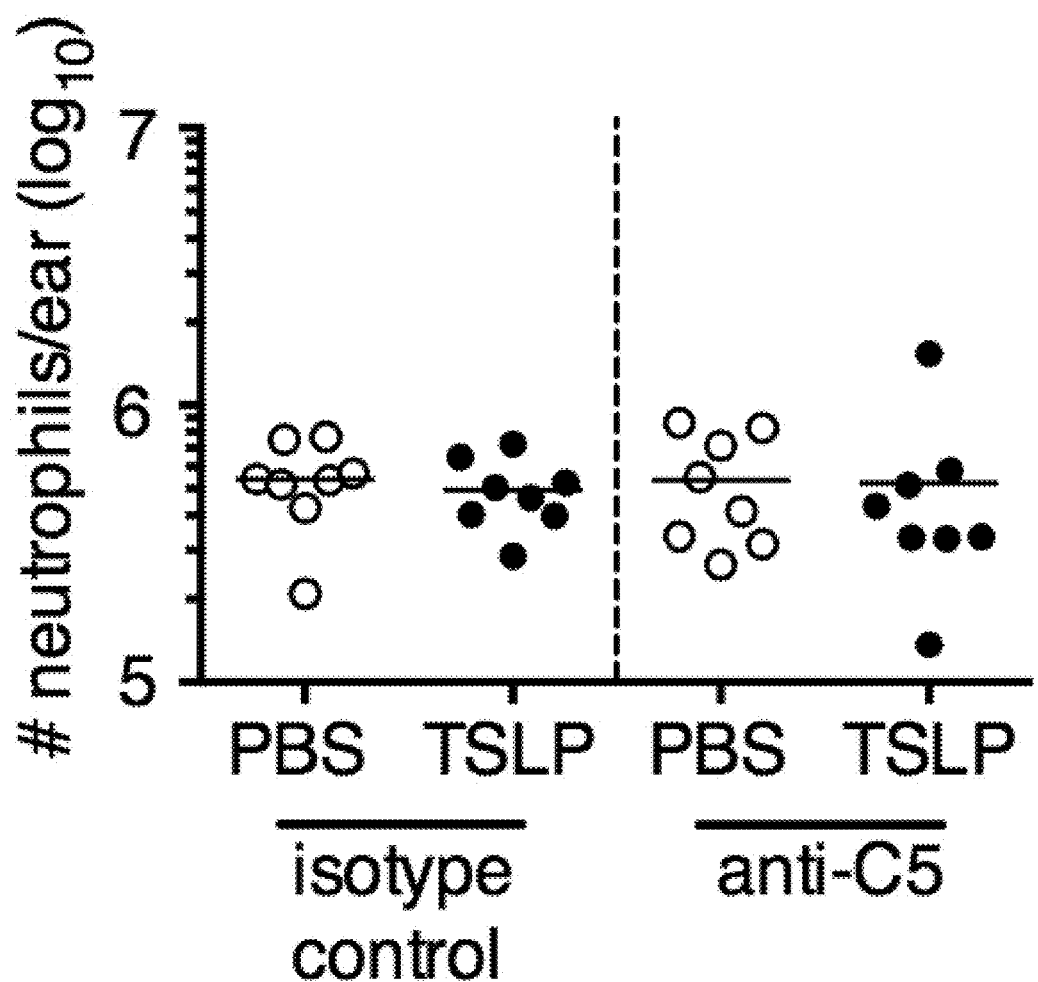
Figure 13E:
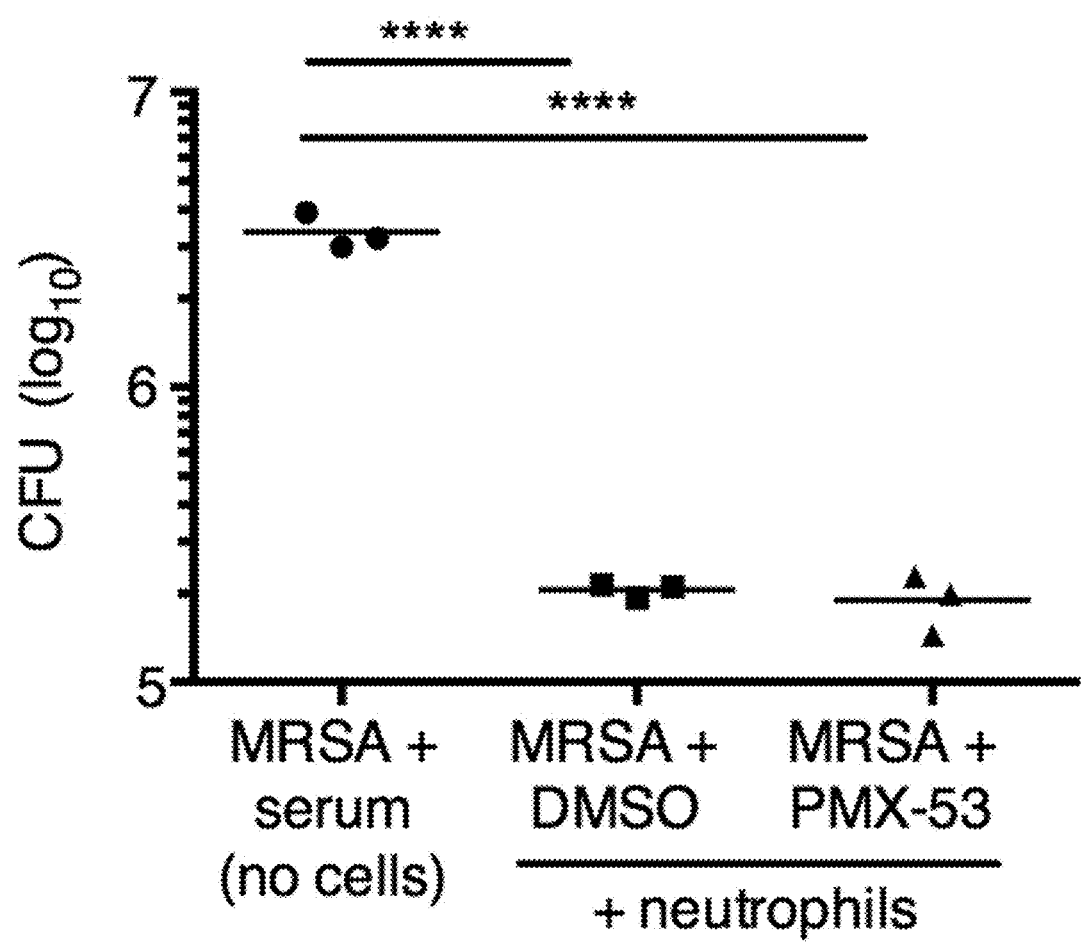

The complement system is a highly conserved innate defense system poised to rapidly respond to invading pathogens, and binding of the complement activation fragment C5a to the C5a receptor 1 (CD88, C5aR1) expressed on neutrophils drives ROS production in these cells. In the whole blood assays above where TSLP promotes the killing of MRSA, blood had been collected with sodium citrate; however, it was observed that treatment of mouse blood with EDTA, which prevents complement activation and C5a generation, eliminated TSLP-mediated MRSA killing in neutrophils (FIG. 13A). Therefore, whether a complement-dependent mechanism was involved in this process was investigated.

Importantly, local injection of WT mice with a C5-blocking antibody (anti-05) during i.d. MRSA ear infection decreased ROS production by neutrophils as compared to ROS production by neutrophils from isotype control treated animals (FIG. 7A), showing that C5 can drive neutrophil ROS production in this model. To elucidate the potential role of C5 in TSLP-mediated MRSA killing in vivo, WT mice were treated with an isotype control or anti-05 antibody along with TSLP or PBS during i.d. MRSA infection. Strikingly, whereas TSLP enhanced MRSA killing in isotype control antibody-treated animals, it had no effect in animals treated with anti-05 (FIG. 7B), demonstrating that C5 is necessary for TSLP-induced neutrophil killing of MRSA in vivo. Although the C5a fragment of C5 is an anaphylotoxin that can act as a chemotactic factor for neutrophils, local blockade of C5 did not affect neutrophil recruitment to the site of infection, as animals treated i.d. with either anti-05 or control antibodies had similar numbers of neutrophils in the ear after MRSA infection (FIGS. 13, B and C). Additionally, TSLP treatment of WT mice increased C5aR1 expression on neutrophils during MRSA skin infection (FIGS. 7, C and D). Expression of C5aR1 indeed appeared critical, as TSLP treatment did not increase MRSA killing in C5ar1$^{-/-}$ mice (FIG. 7E). Thus, TSLP induces in vivo killing of MRSA by neutrophils in a C5- and C5aR1-dependent fashion, via induction of anti-bacterial ROS generation in neutrophils.

Figure 7F:
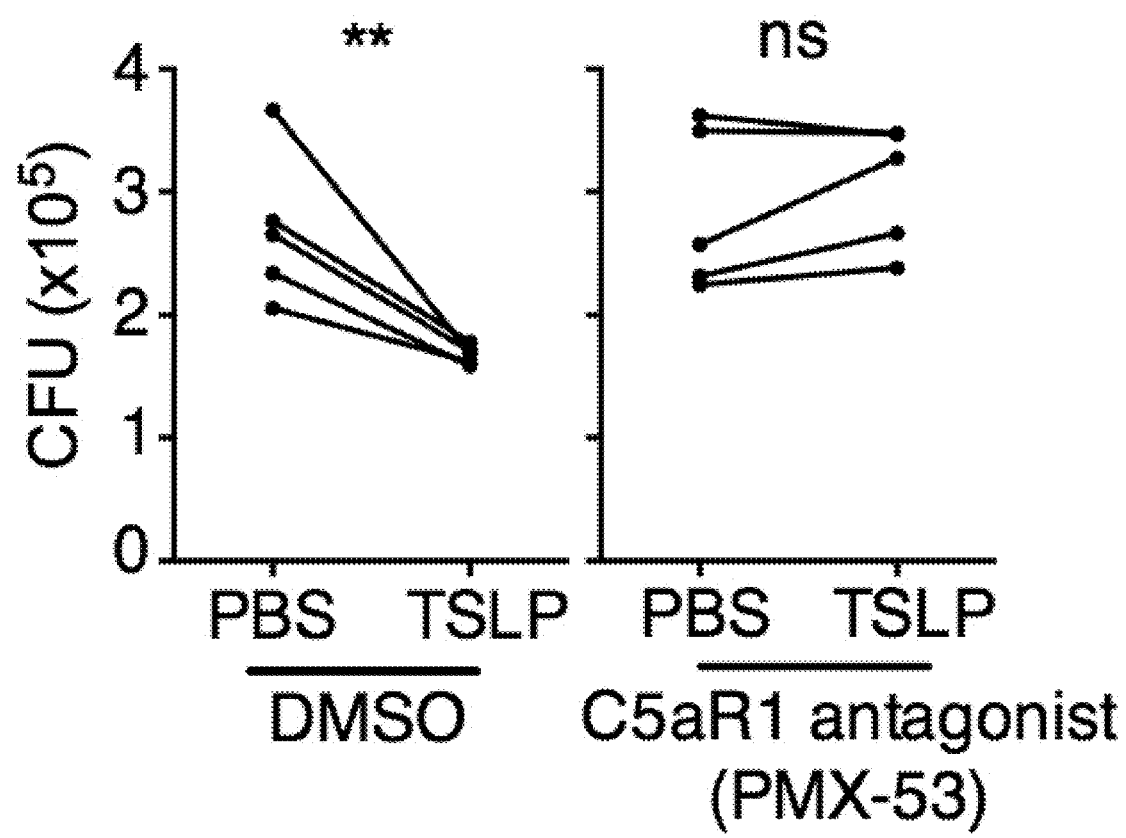
Figure 7G:
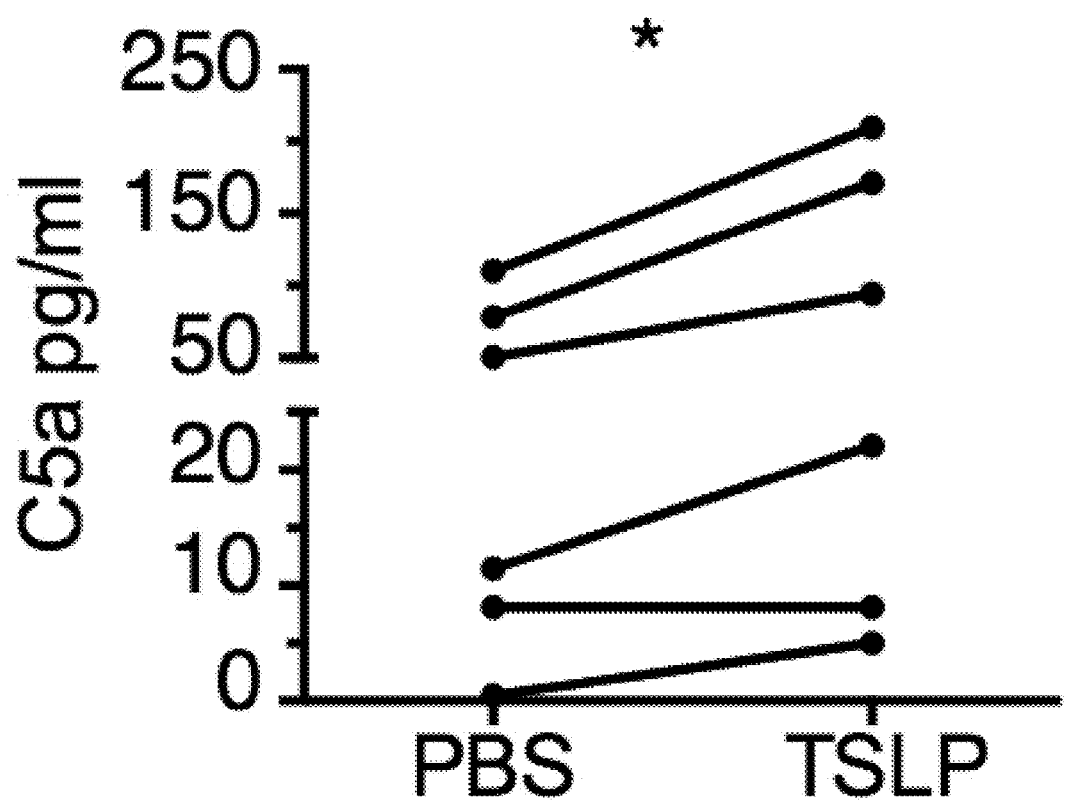

Whether complement C5 was also necessary for the TSLP-enhanced neutrophil killing of MRSA by human neutrophils was also investigated. Importantly, the C5-axis was also required for TSLP-enhanced killing by human neutrophils, as incubating purified human neutrophils with PMX-53, a peptide antagonist of C5aR1 that has been used in clinical trials (37, 38), prevented the TSLP-induced MRSA killing (FIG. 7F). Thus, TSLP enhanced MRSA killing by human neutrophils is both ROS- and complement C5-dependent, in agreement with the in vivo mouse data. Of note, neither the ROS inhibitor (DPI) nor C5aR1 antagonist (PMX-53) abolished the overall killing of MRSA by human neutrophils (FIGS. 13, D and E) but only eliminated the ability of TSLP to enhance neutrophil-killing of MRSA (FIGS. 6E and 7F), indicating the critical engagement of this "C5-ROS axis" by TSLP. Moreover, incubation of purified human neutrophils with TSLP increased their secretion of C5a (FIG. 7G), indicating that TSLP may increase conversion of C5 to C5a or cycling of C5a, thereby creating more ligand for C5aR1. These data demonstrate that TSLP engages the C5 system for MRSA killing in both mouse neutrophils in an in vivo skin infection and in human neutrophils in vitro.

Example 9

This Example demonstrates a neutrophil killing assay that can assess the activity of a TSLP protein, including the relative activity of a variant vs. wild-type TSLP.

Purification of Fc Tagged Chimeric Proteins from Culture Conditioned Media.

Human 293T cells can be transfected with cDNA that encode full length WT human TSLP and mutant human TSLP with a C-terminal Fc fusion in the pFuse-hIgG1-Fc2 vector (InvivoGen). Stable clones of WT TSLP and mutant TSLP can be selected with Zeocin and grown up in large-scale cultures in DMEM supplemented with 2% FBS. The conditioned medium can be collected and filtered through a 0.22 μm PES sterile filter. EDTA (1 mM) and Complete protease inhibitor (Roche) can be added to the medium. The medium can be then concentrated 5 fold using an ultrafiltration device (Millipore) with Biomax 10 kDa Ultrafiltration Discs.

Small Scale Purification.

The concentrated medium can be incubated with Protein A Dynabeads™ (Invitrogen) overnight at 4° C. by head-over-head rotation. The beads can be then separated with an EasyEights™ EasySep™ magnet (STEMCELL Technologies) and washed three times with ice cold PBS. The fusion proteins can be eluted (3×2 column volumes) by incubating the beads with 0.1 M acetic acid (pH 2.8) for 15 min. at 4° C. The eluent fractions can be immediately neutralized with 1 M Tris-HCl (pH 9.5). Buffer exchange to PBS can be then performed on the fractions using Slide-A-Lyzer® Dialysis Cassettes (Thermo Scientific).

Large Scale Purification.

The concentrated medium can be pumped through a HighTrap rProtein A column at a rate of 0.4 mL/min at 4° C. The column can be then washed with PBS for 20 column volumes. The recombinant proteins can be eluted (3×1 column volume) with 0.1 M citric acid (pH 2.5) and the fractions can be immediately neutralized with 1 M Tris-HCl (pH 9.5). Buffer exchange to PBS can be then performed on the fractions using Slide-A-Lyzer® Dialysis Cassettes (Thermo Scientific).

Final products of WT TSLP and, if desired, mutant TSLP, can be analyzed by western blotting and Coomasie stain on an SDS gel, and quantified with human TSLP and Fc ELISA. Their biological activity can be assayed with a MRSA killing assay using human neutrophils isolated from whole blood, such as described as follows.

MRSA/Neutrophil Killing Assay.

An overnight culture of MRSA (2 mL in TSB, 37° C.) can be washed twice with PBS and then diluted to O.D. 0.25 in PBS. 80 µL of this bacterial suspension can be added to 3.5 mL of RPMI with 400 µL of human serum and then incubated for 15 min. at 37° C. with head-over-head rotation. Human neutrophils can be isolated from the whole blood of healthy donors using an EasySep Direct Human Neutrophil Isolation kit (STEMCELL Technologies). For each tube, 50 µL of MRSA mixture can be added to 20 µL of TSLP or mutant TSLP, if desired (1 µg/mL), and 130 µL human neutrophils in RPMI ($4 \times 10^5$ count) and rotated at 37° C. for 3 hours. A tube without the addition of TSLP or a mutant TSP can serve as a control. The mixtures can be then serially diluted ($10^{-1}$, $10^{-2}$, $10^{-3}$, $10^{-4}$) in PBS, and 50 µL of the $10^{-2}$, $10^{-3}$, and $10^{-4}$ dilutions can be each plated on sheep's blood agar plates (Remel). After 16 hours, the plates can be removed from the incubator and the colony-forming units (CFU) can be counted. It will be observed that a lower CFU count relative to a control indicates that a TSLP protein exhibits activity against MRSA. Similarly, a lower CFU count of a mutant (variant) relative to wild-type TSLP indicates that the mutant is more active against MRSA than the wild-type TSLP protein.

Given the variability in neutrophils between human donors, it is desirable to perform such an assay using neutrophils from multiple donors (e.g., at least two, or at least 5, or at least 10 donors or at least 20 donors) so that the relative activity of a wild-type or mutant TSLP protein can be assessed using statistical methods.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of promoting the host defense of a human patient to a bacterial infection comprising administering to a human patient suffering from or at risk of a bacterial infection, a pharmaceutical composition of matter comprising an effective amount of a thymic stromal lymphopoeitin (TSLP) protein or polypeptide in an amount sufficient to promote the host defense of the patient to the bacterial infection, wherein the bacterial infection is the infection of the patient with *Staphylococcus aureus* or *Streptococcus pyogenes*, and wherein the TSLP protein or polypeptide within the pharmaceutical composition of matter (a) comprises, (b) consists essentially of, or (c) consists of an amino acid sequence selected from the group consisting of SEQ ID NOs:1-3 or 7-11 and a combination thereof.

2. The method of claim 1, wherein the patient is suffering from the bacterial infection.

3. The method of claim 1, wherein the patient is at risk of contracting the bacterial infection.

4. The method of claim 1, wherein the bacterial infection is the infection of the patient with Methicillin-resistant *Staphylococcus aureus* (MRSA).

5. The method of claim 1, wherein the pharmaceutical composition is formulated for topical application to a barrier tissue of the patient.

6. The method of claim 5, wherein the barrier tissue comprises conjunctiva, nasal epithelium, oral epithelium, rectal epithelium, skin, or vaginal epithelium.

7. The method of claim 5, wherein the barrier tissue is broken.

8. The method of claim 1, wherein the pharmaceutical composition is formulated for topical application to an abscess.

9. The method of claim 1, wherein the pharmaceutical composition is formulated for parenteral, subcutaneous, intradermal, intramuscular, intraperitoneal or intravenous administration.

10. The method of claim 1, wherein the TSLP protein or polypeptide comprises an amino acid sequence selected from the group consisting of SEQ ID NOs: 1-3 or 7-11.

11. The method of claim 1, wherein the TSLP protein or polypeptide comprises an amino acid sequence selected from the group consisting of SEQ ID NOs: 1-3 or 7-11 and a combination thereof.

12. The method of claim 1, wherein the TSLP protein or polypeptide consists essentially of an amino acid sequence selected from the group consisting of SEQ ID NOs: 1-3 or 7-11.

13. The method of claim 1, wherein the TSLP protein or polypeptide consists essentially of an amino acid sequence selected from the group consisting of SEQ ID NOs:1-3 or 7-11 and a combination thereof.

14. The method of claim 1, wherein the TSLP protein or polypeptide consists of an amino acid sequence selected from the group consisting of SEQ ID NOs:1-3 or 7-11.

15. The method of claim 1, wherein the TSLP protein or polypeptide consists of an amino acid sequence selected from the group consisting of SEQ ID NOs: 1-3 or 7-11 and a combination thereof.

* * * * *

SEQUENCE LISTING

```
<160> NUMBER OF SEQ ID NOS: 11

<210> SEQ ID NO 1
<211> LENGTH: 159
<212> TYPE: PRT
<213> ORGANISM: Homo sapiens

<400> SEQUENCE: 1

Met Phe Pro Phe Ala Leu Leu Tyr Val Leu Ser Val Ser Phe Arg Lys
1               5                   10                  15

Ile Phe Ile Leu Gln Leu Val Gly Leu Val Leu Thr Tyr Asp Phe Thr
            20                  25                  30

Asn Cys Asp Phe Glu Lys Ile Lys Ala Ala Tyr Leu Ser Thr Ile Ser
        35                  40                  45

Lys Asp Leu Ile Thr Tyr Met Ser Gly Thr Lys Ser Thr Glu Phe Asn
    50                  55                  60

Asn Thr Val Ser Cys Ser Asn Arg Pro His Cys Leu Thr Glu Ile Gln
65                  70                  75                  80
```

Ser Leu Thr Phe Asn Pro Thr Ala Gly Cys Ala Ser Leu Ala Lys Glu
            85                  90                  95

Met Phe Ala Met Lys Thr Lys Ala Ala Leu Ala Ile Trp Cys Pro Gly
        100                 105                 110

Tyr Ser Glu Thr Gln Ile Asn Ala Thr Gln Ala Met Lys Lys Arg Arg
            115                 120                 125

Lys Arg Lys Val Thr Thr Asn Lys Cys Leu Glu Gln Val Ser Gln Leu
130                 135                 140

Gln Gly Leu Trp Arg Arg Phe Asn Arg Pro Leu Leu Lys Gln Gln
145                 150                 155

<210> SEQ ID NO 2
<211> LENGTH: 131
<212> TYPE: PRT
<213> ORGANISM: Homo sapiens

<400> SEQUENCE: 2

Tyr Asp Phe Thr Asn Cys Asp Phe Glu Lys Ile Lys Ala Ala Tyr Leu
1               5                   10                  15

Ser Thr Ile Ser Lys Asp Leu Ile Thr Tyr Met Ser Gly Thr Lys Ser
            20                  25                  30

Thr Glu Phe Asn Asn Thr Val Ser Cys Ser Asn Arg Pro His Cys Leu
        35                  40                  45

Thr Glu Ile Gln Ser Leu Thr Phe Asn Pro Thr Ala Gly Cys Ala Ser
    50                  55                  60

Leu Ala Lys Glu Met Phe Ala Met Lys Thr Lys Ala Ala Leu Ala Ile
65                  70                  75                  80

Trp Cys Pro Gly Tyr Ser Glu Thr Gln Ile Asn Ala Thr Gln Ala Met
                85                  90                  95

Lys Lys Arg Arg Lys Arg Lys Val Thr Thr Asn Lys Cys Leu Glu Gln
            100                 105                 110

Val Ser Gln Leu Gln Gly Leu Trp Arg Arg Phe Asn Arg Pro Leu Leu
        115                 120                 125

Lys Gln Gln
    130

<210> SEQ ID NO 3
<211> LENGTH: 132
<212> TYPE: PRT
<213> ORGANISM: Artificial sequence
<220> FEATURE:
<223> OTHER INFORMATION: synthetic

<400> SEQUENCE: 3

Met Tyr Asp Phe Thr Asn Cys Asp Phe Glu Lys Ile Lys Ala Ala Tyr
1               5                   10                  15

Leu Ser Thr Ile Ser Lys Asp Leu Ile Thr Tyr Met Ser Gly Thr Lys
            20                  25                  30

Ser Thr Glu Phe Asn Asn Thr Val Ser Cys Ser Asn Arg Pro His Cys
        35                  40                  45

Leu Thr Glu Ile Gln Ser Leu Thr Phe Asn Pro Thr Ala Gly Cys Ala
    50                  55                  60

Ser Leu Ala Lys Glu Met Phe Ala Met Lys Thr Lys Ala Ala Leu Ala
65                  70                  75                  80

Ile Trp Cys Pro Gly Tyr Ser Glu Thr Gln Ile Asn Ala Thr Gln Ala
                85                  90                  95

```
Met Lys Lys Arg Arg Lys Arg Lys Val Thr Thr Asn Lys Cys Leu Glu
            100                 105                 110

Gln Val Ser Gln Leu Gln Gly Leu Trp Arg Arg Phe Asn Arg Pro Leu
            115                 120                 125

Leu Lys Gln Gln
        130

<210> SEQ ID NO 4
<211> LENGTH: 140
<212> TYPE: PRT
<213> ORGANISM: Mus musculus

<400> SEQUENCE: 4

Met Val Leu Leu Arg Ser Leu Phe Ile Leu Gln Val Leu Val Arg Met
 1               5                  10                  15

Gly Leu Thr Tyr Asn Phe Ser Asn Cys Asn Phe Thr Ser Ile Thr Lys
            20                  25                  30

Ile Tyr Cys Asn Ile Ile Phe His Asp Leu Thr Gly Asp Leu Lys Gly
        35                  40                  45

Ala Lys Phe Glu Gln Ile Glu Asp Cys Glu Ser Lys Pro Ala Cys Leu
    50                  55                  60

Leu Lys Ile Glu Tyr Tyr Thr Leu Asn Pro Ile Pro Gly Cys Pro Ser
65                  70                  75                  80

Leu Pro Asp Lys Thr Phe Ala Arg Arg Thr Arg Glu Ala Leu Asn Asp
                85                  90                  95

His Cys Pro Gly Tyr Pro Glu Thr Glu Arg Asn Asp Gly Thr Gln Glu
            100                 105                 110

Met Ala Gln Glu Val Gln Asn Ile Cys Leu Asn Gln Thr Ser Gln Ile
            115                 120                 125

Leu Arg Leu Trp Tyr Ser Phe Met Gln Ser Pro Glu
        130                 135                 140

<210> SEQ ID NO 5
<211> LENGTH: 121
<212> TYPE: PRT
<213> ORGANISM: Mus musculus

<400> SEQUENCE: 5

Tyr Asn Phe Ser Asn Cys Asn Phe Thr Ser Ile Thr Lys Ile Tyr Cys
 1               5                  10                  15

Asn Ile Ile Phe His Asp Leu Thr Gly Asp Leu Lys Gly Ala Lys Phe
            20                  25                  30

Glu Gln Ile Glu Asp Cys Glu Ser Lys Pro Ala Cys Leu Leu Lys Ile
        35                  40                  45

Glu Tyr Tyr Thr Leu Asn Pro Ile Pro Gly Cys Pro Ser Leu Pro Asp
    50                  55                  60

Lys Thr Phe Ala Arg Arg Thr Arg Glu Ala Leu Asn Asp His Cys Pro
65                  70                  75                  80

Gly Tyr Pro Glu Thr Glu Arg Asn Asp Gly Thr Gln Glu Met Ala Gln
                85                  90                  95

Glu Val Gln Asn Ile Cys Leu Asn Gln Thr Ser Gln Ile Leu Arg Leu
            100                 105                 110

Trp Tyr Ser Phe Met Gln Ser Pro Glu
            115                 120
```

<210> SEQ ID NO 6
<211> LENGTH: 122
<212> TYPE: PRT
<213> ORGANISM: Artificial sequence
<220> FEATURE:
<223> OTHER INFORMATION: synthetic

<400> SEQUENCE: 6

```
Met Tyr Asn Phe Ser Asn Cys Asn Phe Thr Ser Ile Thr Lys Ile Tyr
1               5                   10                  15

Cys Asn Ile Ile Phe His Asp Leu Thr Gly Asp Leu Lys Gly Ala Lys
            20                  25                  30

Phe Glu Gln Ile Glu Asp Cys Glu Ser Lys Pro Ala Cys Leu Leu Lys
        35                  40                  45

Ile Glu Tyr Tyr Thr Leu Asn Pro Ile Pro Gly Cys Pro Ser Leu Pro
    50                  55                  60

Asp Lys Thr Phe Ala Arg Arg Thr Arg Glu Ala Leu Asn Asp His Cys
65                  70                  75                  80

Pro Gly Tyr Pro Glu Thr Glu Arg Asn Asp Gly Thr Gln Glu Met Ala
                85                  90                  95

Gln Glu Val Gln Asn Ile Cys Leu Asn Gln Thr Ser Gln Ile Leu Arg
            100                 105                 110

Leu Trp Tyr Ser Phe Met Gln Ser Pro Glu
        115                 120
```

<210> SEQ ID NO 7
<211> LENGTH: 34
<212> TYPE: PRT
<213> ORGANISM: Artificial sequence
<220> FEATURE:
<223> OTHER INFORMATION: synthetic

<400> SEQUENCE: 7

```
Met Lys Lys Arg Arg Lys Arg Lys Val Thr Thr Asn Lys Cys Leu Glu
1               5                   10                  15

Gln Val Ser Gln Leu Gln Gly Leu Trp Arg Arg Phe Asn Arg Pro Leu
            20                  25                  30

Leu Lys
```

<210> SEQ ID NO 8
<211> LENGTH: 63
<212> TYPE: PRT
<213> ORGANISM: Artificial sequence
<220> FEATURE:
<223> OTHER INFORMATION: synthetic

<400> SEQUENCE: 8

```
Met Phe Ala Met Lys Thr Lys Ala Ala Leu Ala Ile Trp Cys Pro Gly
1               5                   10                  15

Tyr Ser Glu Thr Gln Ile Asn Ala Thr Gln Ala Met Lys Lys Arg Arg
            20                  25                  30

Lys Arg Lys Val Thr Thr Asn Lys Cys Leu Glu Gln Val Ser Gln Leu
        35                  40                  45

Gln Gly Leu Trp Arg Arg Phe Asn Arg Pro Leu Leu Lys Gln Gln
    50                  55                  60
```

<210> SEQ ID NO 9
<211> LENGTH: 60
<212> TYPE: PRT
<213> ORGANISM: Artificial sequence
<220> FEATURE:
<223> OTHER INFORMATION: synthetic

<400> SEQUENCE: 9

Met Lys Thr Lys Ala Ala Leu Ala Ile Trp Cys Pro Gly Tyr Ser Glu
1               5                   10                  15

Thr Gln Ile Asn Ala Thr Gln Ala Met Lys Lys Arg Arg Lys Arg Lys
            20                  25                  30

Val Thr Thr Asn Lys Cys Leu Glu Gln Val Ser Gln Leu Gln Gly Leu
        35                  40                  45

Trp Arg Arg Phe Asn Arg Pro Leu Leu Lys Gln Gln
    50                  55                  60

<210> SEQ ID NO 10
<211> LENGTH: 131
<212> TYPE: PRT
<213> ORGANISM: Artificial Sequence
<220> FEATURE:
<223> OTHER INFORMATION: synthetic

<400> SEQUENCE: 10

Tyr Asp Phe Thr Asn Cys Asp Phe Glu Lys Ile Lys Ala Ala Tyr Leu
1               5                   10                  15

Ser Thr Ile Ser Glu Asp Leu Ile Tyr Tyr Met Ser Gly Thr Lys Ser
            20                  25                  30

Thr Glu Phe Asn Asn Thr Val Ser Cys Ser Asn Arg Pro His Cys Leu
        35                  40                  45

Thr Glu Ile Leu Ser Leu Thr Phe Asn Pro Thr Ala Gly Cys Ala Ser
    50                  55                  60

Leu Ala Lys Glu Lys Phe Ala Met Arg Thr Lys Ala Ala Leu Ala Ile
65                  70                  75                  80

Trp Cys Pro Gly Tyr Ser Glu Thr Gln Ile Asn Ala Thr Gln Ala Met
                85                  90                  95

Lys Lys Arg Arg Lys Arg Lys Val Thr Thr Asn Lys Cys Leu Glu Gln
            100                 105                 110

Val Ser Gln Leu Gln Gly Leu Trp Arg Arg Phe Ser Arg Pro Leu Leu
        115                 120                 125

Lys Gln Gln
    130

<210> SEQ ID NO 11
<211> LENGTH: 132
<212> TYPE: PRT
<213> ORGANISM: Artificial Sequence
<220> FEATURE:
<223> OTHER INFORMATION: synthetic

<400> SEQUENCE: 11

Met Tyr Asp Phe Thr Asn Cys Asp Phe Glu Lys Ile Lys Ala Ala Tyr
1               5                   10                  15

Leu Ser Thr Ile Ser Glu Asp Leu Ile Tyr Tyr Met Ser Gly Thr Lys
            20                  25                  30

Ser Thr Glu Phe Asn Asn Thr Val Ser Cys Ser Asn Arg Pro His Cys
        35                  40                  45

Leu Thr Glu Ile Leu Ser Leu Thr Phe Asn Pro Thr Ala Gly Cys Ala
    50                  55                  60

Ser Leu Ala Lys Glu Lys Phe Ala Met Arg Thr Lys Ala Ala Leu Ala
65                  70                  75                  80

```
-continued

Ile Trp Cys Pro Gly Tyr Ser Glu Thr Gln Ile Asn Ala Thr Gln Ala
                85                  90                  95

Met Lys Lys Arg Arg Lys Arg Lys Val Thr Thr Asn Lys Cys Leu Glu
            100                 105                 110

Gln Val Ser Gln Leu Gln Gly Leu Trp Arg Arg Phe Ser Arg Pro Leu
            115                 120                 125

Leu Lys Gln Gln
    130
```